US011332757B2

(12) United States Patent
Maguire et al.

(10) Patent No.: US 11,332,757 B2
(45) Date of Patent: *May 17, 2022

(54) DELIVERY ACROSS CELL PLASMA MEMBRANES

(71) Applicant: Avectas Limited, Kildare (IE)

(72) Inventors: Michael Maguire, Dublin (IE); Shirley O'Dea, Maynooth (IE)

(73) Assignee: Avectas Limited, County Kildare (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/092,161

(22) Filed: Nov. 6, 2020

(65) Prior Publication Data

US 2021/0071200 A1    Mar. 11, 2021

Related U.S. Application Data

(63) Continuation of application No. 16/841,236, filed on Apr. 6, 2020, which is a continuation of application No. 15/521,192, filed as application No. PCT/US2015/057247 on Oct. 23, 2015, now Pat. No. 10,612,042.

(30) Foreign Application Priority Data

Oct. 24, 2014  (GB) ..................... 1419011
Oct. 24, 2014  (GB) ..................... 1419012
Oct. 24, 2014  (GB) ..................... 1419013

(51) Int. Cl.
| | | |
|---|---|---|
| C12N 15/89 | (2006.01) | |
| A61K 31/7115 | (2006.01) | |
| B05B 7/24 | (2006.01) | |
| C12M 1/42 | (2006.01) | |
| C12N 15/113 | (2010.01) | |
| C12N 15/87 | (2006.01) | |
| C12N 5/00 | (2006.01) | |
| C12N 5/077 | (2010.01) | |
| C12N 5/0775 | (2010.01) | |
| C12N 5/0783 | (2010.01) | |
| B05B 1/02 | (2006.01) | |

(52) U.S. Cl.
CPC ........ *C12N 15/895* (2013.01); *A61K 31/7115* (2013.01); *B05B 1/02* (2013.01); *B05B 7/2491* (2013.01); *C12M 35/04* (2013.01); *C12N 5/00* (2013.01); *C12N 5/0018* (2013.01); *C12N 5/0636* (2013.01); *C12N 5/0656* (2013.01); *C12N 5/0662* (2013.01); *C12N 15/113* (2013.01); *C12N 15/87* (2013.01); *C12N 2310/14* (2013.01); *C12N 2500/12* (2013.01); *C12N 2500/30* (2013.01); *C12N 2500/34* (2013.01); *C12N 2500/60* (2013.01)

(58) Field of Classification Search
None
See application file for complete search history.

(56) References Cited

U.S. PATENT DOCUMENTS

| | | | |
|---|---|---|---|
| 5,814,331 A | 9/1998 | Holen | |
| 6,764,720 B2 | 7/2004 | Pui et al. | |
| 7,293,559 B2 | 11/2007 | Ganan-Calvo | |
| 7,667,004 B2 | 2/2010 | Zhong et al. | |
| 7,927,874 B2 | 4/2011 | Ikemoto et al. | |
| 8,101,200 B2 | 1/2012 | Whitbourne et al. | |
| 8,697,359 B1 | 4/2014 | Zhang | |
| 8,932,814 B2 | 1/2015 | Cong et al. | |
| 9,023,649 B2 | 5/2015 | Mali et al. | |
| 9,074,199 B1 | 7/2015 | Chavez et al. | |
| 9,079,878 B2 | 7/2015 | Bagal et al. | |
| 10,612,042 B2 * | 4/2020 | Maguire ............. | C12N 15/113 |
| 2001/0006643 A1 | 7/2001 | Hope | |
| 2002/0018795 A1 | 2/2002 | Whitbourne et al. | |
| 2004/0213744 A1 | 10/2004 | Lulla et al. | |
| 2009/0178934 A1 | 7/2009 | Jarvius et al. | |
| 2013/0053794 A1 | 2/2013 | Cadden et al. | |
| 2014/0349402 A1 | 11/2014 | Cooper et al. | |
| 2015/0071903 A1 | 3/2015 | Liu et al. | |
| 2016/0102322 A1 | 4/2016 | Ravinder et al. | |
| 2017/0356011 A1 | 12/2017 | Maguire et al. | |
| 2019/0194691 A1 | 6/2019 | Maguire et al. | |

FOREIGN PATENT DOCUMENTS

| | | |
|---|---|---|
| JP | H03-251187 A | 11/1991 |
| JP | H06-62871 A | 3/1994 |
| JP | 2004-536089 A | 12/2004 |
| WO | 92/18164 A1 | 10/1992 |
| WO | 03/000174 A2 | 1/2003 |
| WO | 2009130187 A1 | 10/2009 |
| WO | 2013/058812 A1 | 4/2013 |
| WO | 2013/061205 A2 | 5/2013 |
| WO | 2013142578 A1 | 9/2013 |
| WO | 2014/033186 A1 | 3/2014 |
| WO | 2015088643 A1 | 6/2015 |
| WO | 2015/071474 | 8/2015 |
| WO | 2016/065341 A1 | 4/2016 |
| WO | 2017/115128 A2 | 7/2017 |

OTHER PUBLICATIONS

Papapetrou, et al. (2005) "Genetic modification of hematopoietic stem cells with nonviral systems: past progress and future prospects", 12: S118-S130. (Year: 2005).*

Elhissi et al. (2011) "Vibrating-Mesh Nebulization of Liposomes Generated Using an Ethanol-Based Proliposome Technology", Journal of Liposome Research, 21(2):173-180.

(Continued)

*Primary Examiner* — Robert M Kelly
(74) *Attorney, Agent, or Firm* — Mintz Levin Cohn Ferris Glovsky and Popeo, P.C.; Ingrid A. Beattie

(57) ABSTRACT

Delivering a payload across a plasma membrane of a cell includes providing a population of cells and contacting the population of cells with a volume of an aqueous solution. The aqueous solution includes the payload and alcohol content greater than 5 percent concentration. The volume of the aqueous solution may be a function of exposed surface area of the population of cells, or may be a function of a number of cells in the population of cells. Related compositions, apparatus, systems, techniques, and articles are also described.

28 Claims, 56 Drawing Sheets

(56) References Cited

OTHER PUBLICATIONS

Gurtovenko et al. (Oct. 2010) "Defect-Mediated Trafficking across Cell Membranes: Insights from in Silico Modeling", Chemical Reviews, 110(10):6077-6103.
Gurtovenko et al. (2009) "Interaction of Ethanol with Biological Membranes: The Formation of Non-bilayer Structures within the Membrane Interior and their Significance", The Journal of Physical Chemistry, Part B, 113(7):1983-1992.
Hapala (1997) "Breaking the Barrier: Methods for Reversible Permeabilization of Cellular Membranes", Critical Reviews in Biotechnology, 17(2):105-122.
Lemoine et al. (May 12, 2005) "Mechanism of Efficient Transfection of the Nasal Airway Epithelium by Hypotonic Shock", Gene Therapy, 12(16):1275-1282.
Medepalli et al. (Apr. 19, 2013) "A New Technique for Reversible Permeabilization of Live Cells for Intracellular Delivery of Quantum Dots", Nanotechnology, 205101, 24(20):13 Pages.
O'Dea et al. (Mar. 30, 2017) "Vector-Free Intracellular Delivery by Reversible Permeabilization", PLOS One, e0174779, 12(3):23 Pages.
Van De Ven et al. (2009) "Delivery of Optical Contrast Agents Using Triton-X100, Part 1: Reversible Permeabilization of Live Cells for Intracellular Labeling", Journal of Biomedical Optics, 14(2):17 Pages.
Van De Ven et al. (2009) "Delivery of Optical Contrast Agents Using Triton-X100, Part 2: Enhanced Mucosal Permeation for the Detection of Cancer Biomarkers", Journal of Biomedical Optics, 14(2):22 Pages.
Beerli et al. (Dec. 8, 1998) "Toward Controlling Gene Expression at Willi Specific Regulation of the erbB-2/HER-2 Promoter by Using Polydactyl Zinc Finger Proteins Constructed from Modular Building Blocks", Proceedings of the National Academy of Sciences, 95(25)114628-14633.
Besser et al. (2009) "Modifying Interleukin-2 Concentalions During Culture Improves Function of T Cells for Adoptive Immunotherapy", Cytotherapy, vol. 11, No. 2, 206-217.
Bhakta et al. (2013) "Highly Active Zinc-finger Nucleases by Extended Modular Assembly", Genome Research, 23:530-538.
Boch et al. (2009) "Breaking the Code of DNA Binding Specificity of TAL-Type III Effectors", Science, 326(5959):1509-1512.
Branzei et al. (Apr. 2008) "Regulation of DNA Repair Throughout the Cell Cycle", Nature Reviews Molecular Cell Biology, 9(4):297-308.
Brocard et al. (Dec. 2006) "Peroxisome Targeting Signal 1: Is it Really a Simple Tripeptide?", Biochimica et Biophysica Acta (BBA)—Molecular Cell Research, 1763(12):1565-1573.
Burger et al. (2016) "Maximizing Mutagenesis with Solubilized CRISPR-Cas9 Ribonucleoprotein Complexes", Development, 143(11):2025-2037.
Carr et al. (Dec. 2009) "Genome Engineering", Nature Biotechnology, 27(12):1151-1162.
Cermak et al. (Apr. 14, 2011) "Efficient design and assembly of custom TALEN and other TAL effector-based constructs for DNA targeting", Nucleic Acids Research, 39(12):11 pages.
Chen et al. (Dec. 2003) "Influence of Histidine on the Stability and Physical Properties of a Fully Human Antibody in Aqueous and Solid Forms", Pharmaceutical Research, 20(12):1952-1960.
Chevalier et al. (2001) "Homing Endonucleases: Structural and Functional Insight into the Catalysts of Intron/intein Mobility", Nucleic Acids Research, 29(18):3757-3774.
Cho et al. (Nov. 2013) "Heritable Gene Knockout in Caenorhabditis Elegans by Direct Injection of Cas9-sgRNA Ribonucleoproteins", Genetics, 195(3):1177-1180.
Cho et al. (Mar. 2013) "Targeted Genome Engineering in Human Cells with the Cas9 RNA-Guided Endonuclease", Nature Biotechnology, 31(3):230-232.
Christian et al. (Oct. 1, 2010) "Targeting DNA Double-Strand Breaks with TAL Effector Nucleases", Genetics, 186(2):757-761.

D'Amico et al. (Feb. 15, 2009) "A Nondetergent Sulfobetaine Improves Protein Unfolding Reversibility in Microcalorimetric Studies", Analytical Biochemistry, 385(2):389-391.
D'Astolfo et al. (Apr. 23, 2015) "Efficient Intracellular Delivery of Native Proteins", Cell, 161(3):674-690.
Deng et al. (2012) "Structural Basis for Sequence-specific Recognition of DNA by TAL Effectors", Science, 335(6069):720-723.
Dingwall et al. (Dec. 1991) "Nuclear Targeting Sequences—A Consensus?", Trends in Biochemical Sciences, 16(12):478-481.
Dwyer et al. (1999) "Molecular Simulation of the Effects of Alcohols on Peptide Structure", Biopolymers, 49(7):635-645.
Eyles et al. (Feb. 16, 2010) "Nature's Molecular Sponges: Small Heat Shock Proteins Grow into their Chaperone Roles", Proceedings of the National Academy of Sciences, 107(7):2727-2728.
Ferns et al. (Oct. 2011) "Protection Against Protein Aggregation by Alpha-crystalline as a Mechanism of Preconditioning", Neurochemical Research, 37:244-252.
Fineran et al. (Dec. 2012) "Memory of Viral Infections by CRISPR-Cas Adaptive Immune Systems: Acquisition of New Information", Virology, 434(2):202-209.
Han et al. (Aug. 14, 2015) "CRISPR-cas9 Delivery to Hard-to-transfect Cells via Membrane Deformation", Science Advances, Article No. e1500454, 1(7):9 pages.
Han et al. (Oct. 2007) "Effects of Sugar Additives on Protein Stability of Recombinant Human Serum Albumin During Lyophilization and Storage", Archives of Pharmacal Research, 30(9):1124-1131.
Hsu et al. (Jun. 5, 2014) "Development and Applications of CRISPR-Cas9 for Genome Engineering", Cell, 157(6):1262-1278.
Ibarra et al. (Aug. 23, 2016) "Efficient Modification of the CCR5 Locus in Primary Human T Cells With megaTAL Nuclease Establishes HIV-1 Resistance", Molecular Therapy—Nucleic Acids, Article No. e352, 5:10 pages.
Jinek et al. (Aug. 17, 2012) "A Programmable Dual-RNA—Guided DNA Endonuclease in Adaptive Bacterial Immunity", Science, 337(6069):816-821.
Kalderon et al. (Dec. 1984) "A Short Amino Acid Sequence Able to Specify Nuclear Location", Biochemistry Division, National Institute for Medical Research, Cell, 39(3 Pt 2):499-509.
Kerwin Bruce A. (Aug. 2008) "Polysorbates 20 and 80 used in the Formulation of Protein Biotherapeutics: Structure and Degradation Pathways", 97(8):2924-2935.
Kim et al. (2014) "Highly Efficient RNA-Guided Genome Editing in Human Cells via Delivery of Purified Cas9 Ribonucleoproteins", Genome Research, 24(6):1012-1019.
Li et al. (2015) "Challenges in CRISPR/CAS9 Delivery: Potential Roles of Nonviral Vectors", Human Gene Therapy, 26(7):452-462.
Liang et al. (Aug. 20, 2015) "Rapid and Highly Efficient Mammalian Cell Engineering via Cas9 Protein Transfection", Journal of Biotechnology, 208:44-53.
Lin et al. (Dec. 15, 2014) "Enhanced Homology-directed Human Genome Engineering by Controlled Timing of CRISPR/Cas9 Delivery", eLife, 3:e04766:13 pages.
Liu et al. (Oct. 2005) "Trehalose Differentially Inhibits Aggregation and Neurotoxicity of Beta-amyloid 40 and 42", Neurobiology of Disease, 20(1):74-81.
Makkerh et al. (Aug. 1996) "Comparative Mutagenesis of Nuclear Localization Signals Reveals the Importance of Neutral and Acidic Amino Acids", Current Biology, 6(8):1025-1027.
Martin et al. (May 1, 2017) "Efficient Vector-free Engineering of MSC with Retention of Cell Viability and Differentiation Potential", Cytotherapy, 19(5):e23.
Meaking et al. (Dec. 27, 1995) "Electroporation-induced Damage in Mammalian Cell DNA", Biochimica et Biophysica Acta (BBA)—Gene Structure and Expression, 1264(3):357-362.
Miller et al. (Feb. 2011) "A TALE Nuclease Architecture for Efficient Genome Editing", Nature Biotechnology, 29(2): 143-148.
Morimoto et al. (2008) "Proteotoxic Stress and Inducible Chaperone Networks in Neurodegenerative Disease and Aging", Genes & Development, 22(11):1427-1438.
Nakamura et al. (2000) "Codon Usage Tabulated from International DNA Sequence Database: Status for the Year 2000", Nucleic Acid Research, 28(1):292 (1 page).

(56) References Cited

OTHER PUBLICATIONS

O'Dea et al. (May 1, 2012) "Transfection of 'Hard to Transfect' Cells Using Electrospray: 'Sprayfection'", Physical Methods of Gene Delivery, 20(Suppl 1):S241 (1 page).
Ohta et al., "Metabolomic Approach for Improving Ethanol Stress Tolerance in *Saccharomyces cerevisiae*", Journal of Bioscience and Bioengineering, Apr. 2016, 121(4):399-405.
Omura Tsuneo (1998) "Mitochondria-Targeting Sequence, a Multi-Role Sorting Sequence Recognized at All Steps of Protein Import into Mitochondria", The Journal of Biochemistry, 123(6):1010-1016.
Osborn et al. (Mar. 2016) "Evaluation of TCR Gene Editing Achieved by TALENs, CRISPR/Cas9, and megaTAL Nucleases", Molecular Therapy, 24(3):570-581.
Park et al. (Aug. 2015) "Engineering Mesenchymal Stem Cells for Regenerative Medicine and Drug Delivery", Methods, 84:3-16.
Platts et al. (2015) "Controlling Protein Stability: Mechanisms Revealed using Formulations of Arginine, Glycine and Guanidinium HCL with Three Globular Proteins", International Journal of Pharmaceutics, 486(1-2):131-135.
Rapaport Doron (Nov. 2003) "Finding the Right Organelle. Targeting Signals in Mitochondrial Outer-Membrane Proteins", EMBO Reports, 4(10):948-952.
Reddy et al. (Nov. 2006) "Chaperone-like Activity and Hydrophobicity of a-Crystallin", IUBMB Life, 58(11):632-641.
Richter et al. (Oct. 20, 2010) "The Heat Shock Response: Life on the Verge of Death", Molecular Cell, 40(2):253-266.
Zuris et al. (Jan. 2015) "Efficient Delivery of Genome-Editing Proteins In Vitro and In Vivo", Nature Biotechnology, 33(1):73-80.
Samuel et al. (2000) "Proline Inhibits Aggregation During Protein Refolding", Protein Science, 9(2):344-352.
Sather et al. (Sep. 30, 2015) "Efficient Modification of CCR5 in Primary Human Hematopoietic Cells Using a megaTAL Nuclease and AAV Donor Template", Science Translational Medicine, 7(307):307ra156 (29 pages).
Schumann et al. (Aug. 18, 2015) "Generation of Knock-in Primary Human T Cells using Cas9 Ribonucleoproteins", Proceedings of the National Academy of Sciences, 112(33):10437-10442.
Scott et al. (Aug. 3, 2011) "NoD: A Nucleolar Localization Sequence Detector for Eukaryotic and Viral Proteins", BMC Bioinformatics, 12:317 (7 pages).
Stengel et al. (Feb. 2, 2010) "Quaternary Dynamics and Plasticity Underlie Small Heat Shock Protein Chaperone Function", Proceedings of the National Academy of Sciences, 107(5):2007-2012.
Sung et al. (Nov. 2013) "Highly Efficient Gene Knockout in Mice and Zebrafish with RNA-guided Endonucleases", Genome Research, 24(1):125-131.
Wang et al. (Mar. 25, 2014) "Progressive Engineering of a Homing Endonuclease Genome Editing Reagent for the Murine X-linked Immunodeficiency Locus", Nucleic Acids Research, 42(10):6463-6475.
Whitley et al. (Apr. 1999) "Heat Shock Proteins: A Review of the Molecular Chaperones", Journal of Vascular Surgery, 29(4):748-751.
Wiedenheft et al. (Feb. 15, 2012) "RNA-Guided Genetic Silencing Systems in Bacteria and Archaea", Nature, 482(7385):331-338.
Xie et al. (1997) "Mechanism of the Stabilization of Ribonuclease A by Sorbitol: Preferential Hydration is Greater for the Denatured then for the Native Protein", Protein Science, 6(1):211-221.
Young et al. (Dec. 5, 2005) "Gelatin as a Delivery Vehicle for the Controlled Release of Bioactive Molecules", Journal of Conlrolled Release, 109(1-3):256-274.
Gaj et al. (Dec. 2016) "Genome-Editing Technologies: Principles and Applications", Cold Spring Harbor Perspectives in Biology, 8(12):a023754.
Gruber et al. (Jul. 1, 2008) "The Vienna RNA Websuite", Nucleic Acids Research, 36:W70-W74.

* cited by examiner

300

810 — GENERATING, BY A PNEUMATIC GENERATOR, GAS UNDER PRESSURE

820 — SWITCHING A VALVE FROM A CLOSED POSITION FOR PREVENTING THE GAS UNDER THE PRESSURE FROM ACTIVATING AN ATOMIZER AND AN OPEN POSITION FOR ALLOWING GAS UNDER PRESSURE TO ACTIVATE THE ATOMIZER TO PRODUCE COLLOIDAL DROPLETS

*FIG. 3*

20 µl micropipette delivery Propidium iodide

| Centre of Well | Edge of Well |
|---|---|
|  |  |
|  |  |

FITC Fluorescence  Bright field image 10-kDa Dextran-Alexa488 and DAPI

Approximate Volume Delivered per cell (μL/cell)

| | | Cells/Well 48 | | |
|---|---|---|---|---|
| | | Large (MSC) | Medium (A549) | Small (U266) |
| | cells/well | 134423 | 537691 | 840143 |
| Vol Delivered per well (μL/well) | 0.5 | 3.72E-06 | 9.30E-07 | 5.95E-07 |
| | 5 | 3.72E-05 | 9.30E-06 | 5.95E-06 |
| | 10 | 7.44E-05 | 1.86E-05 | 1.19E-05 |
| | 15 | 1.12E-04 | 2.79E-05 | 1.79E-05 |
| | 100 | 7.44E-04 | 1.86E-04 | 1.19E-04 |

*FIG. 52*

Approximate Volume Delivered per square micrometer (µL/µm²)

| | | Surface area of one well in 24 well plate (µm²) | Surface area of one well in 48 well plate (µm²) |
|---|---|---|---|
| Vol Delivered per well (µL/well) | | 190,000,000 | 95,000,000 |
| | 0.5 | 2.63E-09 | 5.26E-09 |
| | 5 | 2.63E-08 | 5.26E-08 |
| | 10 | 5.26E-08 | 1.05E-07 |
| | 15 | 7.89E-08 | 1.58E-07 |
| | 100 | 5.26E-07 | 1.05E-06 |

*FIG. 53*

| Cell Type | Morphology | Diameter (μm) | Diameter (cm) | Radius (cm) | Area of cell (cm²) | Cells/well 24 | Cells/well 48 |
|---|---|---|---|---|---|---|---|
| *A549 | Epithelial | 15 | 0.0015 | 0.00075 | 1.77E-06 | 1,075,383 | 537,691 |
| *CHO | Epithelial | 15 | 0.0015 | 0.00075 | 1.77E-06 | 1,075,383 | 537,691 |
| *COS-7 | Fibroblast | 20 | 0.002 | 0.001 | 3.14E-06 | 604,903 | 302,451 |
| *MSC | Stem | 30 | 0.003 | 0.0015 | 7.07E-06 | 268,846 | 134,423 |
| *HeLa | Epithelial | 20 | 0.002 | 0.001 | 3.14E-06 | 604,903 | 302,451 |
| **K562 | lymphoblast | 22 | 0.0022 | 0.0011 | 3.80E-06 | 499,920 | 249,960 |
| *MCF7 | Epithelial | 16 | 0.0016 | 0.0008 | 2.01E-06 | 945,161 | 472,580 |
| **U266 | lymphoblast | 12 | 0.0012 | 0.0006 | 1.13E-06 | 1,680,286 | 840,143 |
| *Splenocyte | | 8 | 0.0008 | 0.0004 | 5.03E-07 | 3,780,643 | 1,890,322 |
| Mature DC | | 13 | 0.0013 | 0.00065 | 1.33E-06 | 1,431,723 | 715,861 |
| Small neurons | Brain | 4 | 0.0004 | 0.0002 | 1.26E-07 | 15,122,572 | 7,561,286 |
| Large neurons | Brain | 100 | 0.01 | 0.005 | 7.85E-05 | 24,196 | 12,098 |
| Ovum | | 120 | 0.012 | 0.006 | 1.13E-04 | 16,803 | 8,401 |
| RBC | Blood | 7 | 0.0007 | 0.00035 | 3.85E-07 | 4,937,983 | 2,468,991 |
| **CD34+ | Spherical | 10 | 0.001 | 0.0005 | 7.85E-07 | 2,419,612 | 1,209,806 |
| *HepG2 | Epithelial | 18 | 0.0018 | 0.0009 | 2.54E-06 | 746,794 | 373,397 |
| *Adherent | | | | | | | |
| **Suspension | | | | | | | |

FIG. 54

Measured Volume Delivered per cell (µL/cell)

|  |  | Cells/Well 48 well plate -Measured | | |
|---|---|---|---|---|
|  |  | MSC | CHO | A549 |
|  | cells/well | 46200 | 255000 | 102000 |
| Vol Delivered per well (µL/well) | 0.5 | 1.08E-05 | 1.96E-06 | 4.90E-06 |
| | 5 | 1.08E-04 | 1.96E-05 | 4.90E-05 |
| | 10 | 2.16E-04 | 3.92E-05 | 9.80E-05 |
| | 15 | 3.25E-04 | 5.88E-05 | 1.47E-04 |
| | 100 | 2.16E-03 | 3.92E-04 | 9.80E-04 |

*FIG. 55*

DELIVERY ACROSS CELL PLASMA MEMBRANES

RELATED APPLICATION

This application is a continuation of and claims the benefit under 35 U.S.C. § 120 of U.S. patent application Ser. No. 16/841,236, filed on Apr. 6, 2020, presently pending, which is a continuation of U.S. patent application Ser. No. 15/521, 192, filed on Apr. 21, 2017, issued as U.S. Pat. No. 10,612, 042, which is a national stage application filed under 35 U.S.C. § 371, of International Patent Application No. PCT/US2015/057247 filed Oct. 23, 2015, which claims the benefit of and priority to British application no. 1419013.6 filed Oct. 24, 2014, to British application no. 1419012.8 filed Oct. 24, 2014, and to British application no. 1419011.0 filed Oct. 24, 2014, the entire contents of each of which are hereby expressly incorporated by reference herein.

TECHNICAL FIELD

The present subject matter relates to delivering agents cell plasma membranes. The present subject matter may include, for example, delivering molecular, biological and pharmacological therapeutic agents to a target site, such as a cell, tissue, or organ.

BACKGROUND

Despite technical advances in some areas, delivery of certain molecules into cells remains a challenge because of factors such as size or charge of the molecule. A plasma or cell membrane is a semi-permeable biological membrane, which acts as a selective barrier, regulating the chemical composition of a cell. Therefore, only certain molecules can translocate across the plasma membrane by passive diffusion into a cell. Small, hydrophobic molecules (such as $O_2$, $CO_2$ and $N_2$) and small, uncharged polar molecules (such as $H_2O$ and glycerol) can passively diffuse across a plasma membrane. Larger, uncharged polar molecules (such as amino acids, glucose, and nucleotides) and ions (such as $H^+$, $Na^+$, $K^+$ and $Cl^-$) cannot passively diffuse into a cell.

SUMMARY

The invention is based on the surprising discovery that compounds or mixtures of compounds (compositions) are delivered into the cytoplasm of eukaryotic cells by contacting the cells with a solution containing a compound(s) to be delivered (e.g., payload) and an agent that reversibly permeates or dissolves a cell membrane. Preferably, the solution is delivered to the cells in the form of a spray, e.g., of five aqueous particles. For example, the cells are coated with the spray but not soaked or submersed in the delivery compound-containing solution. Exemplary agents that permeate or dissolve a eukaryotic cell membrane include alcohols and detergents such as ethanol and Triton X-100, respectively. Other exemplary detergents, e.g., surfactants include polysorbate 20 (e.g., Tween 20), 3-[(3-cholamidopropyl)dimethylammonio]-1-propanesulfonate (CHAPS), 3-[(3-cholamidopropyl)dimethylammonio]-2-hydroxy-1-propanesulfonate (CHAPSO), sodium dodecyl sulfate (SDS), and octyl glucoside.

An example of conditions to achieve a coating of a population of coated cells include delivery of a fine particle spray, e.g., the conditions exclude dropping or pipetting a bolus volume of solution on the cells such that a substantial population of the cells are soaked or submerged by the volume of fluid. Thus, the mist or spray comprises a ratio of volume of fluid to cell volume. Alternatively, the conditions comprise a ratio of volume of mist or spray to exposed cell area, e.g., area of cell membrane that is exposed when the cells exist as a confluent or substantially confluent layer on a substantially flat surface such as the bottom of a tissue culture vessel, e.g., a well of a tissue culture plate, e.g., a microtiter tissue culture plate.

Accordingly, there is a need to provide a vector-free e.g., viral vector-free, approach for delivering biologically relevant payloads, e.g., compounds or compositions, across a plasma membrane and into cells. "Cargo" or "payload" are terms used to describe a compound, or composition that is delivered via an aqueous solution across a cell plasma membrane and into the interior of a cell.

In an aspect, delivering a payload across a plasma membrane of a cell includes providing a population of cells and contacting the population of cells with a volume of an aqueous solution. The aqueous solution includes the payload and an alcohol content greater than 5 percent concentration. The volume of the aqueous solution may be a function of exposed surface area of the population of cells, or may be a function of a number of cells in the population of cells.

In another aspect, a composition for delivering a payload across a plasma membrane of a cell includes an aqueous solution including the payload, an alcohol at greater than 5 percent concentration, less than 46 mM salt, less than 121 mM sugar, and less than 19 mM buffering agent. For example, the alcohol, e.g., ethanol, concentration does not exceed 50%.

One or more of the following features can be included in any feasible combination. The volume of solution to be delivered to the cells is a plurality of units, e.g., a spray, e.g., a plurality of droplets on aqueous particles. The volume is described relative to an individual cell or relative to the exposed surface area of a confluent or substantially confluent (e.g., at least 75%, at least 80% confluent, e.g., 85%, 90%, 95%, 97%, 98%, 100%) cell population. For example, the volume can be between $6.0 \times 10^{-7}$ microliter per cell and $7.4 \times 10^{-4}$ microliter per cell. The volume is between $4.9 \times 10^{-6}$ microliter per cell and $2.2 \times 10^{-3}$ microliter per cell. The volume can be between $9.3 \times 10^{-6}$ microliter per cell and $2.8 \times 10^{-5}$ microliter per cell. The volume can be about $1.9 \times 10^{-5}$ microliters per cell, and about is within 10 percent. The volume is between $6.0 \times 10^{-7}$ microliter per cell and $2.2 \times 10^{-3}$ microliter per cell. The volume can be between $2.6 \times 10^{-9}$ microliter per square micrometer of exposed surface area and $1.1 \times 10^{-6}$ microliter per square micrometer of exposed surface area. The volume can be between $5.3 \times 10^{-8}$ microliter per square micrometer of exposed surface area and $1.6 \times 10^{-7}$ microliter per square micrometer of exposed surface area. The volume can be about $1.1 \times 10^{-7}$ microliter per square micrometer of exposed surface area. About can be within 10 percent.

Confluency of cells refers to cells in contact with one another on a surface. For example, it can be expressed as an estimated (or counted) percentage, e.g., 10% confluency means that 10% of the surface, e.g., of a tissue culture vessel, is covered with cells, 100% means that it is entirely covered. For example, adherent cells grow two dimensionally on the surface of a tissue culture well, plate or flask. Non-adherent cells can be spun down, pulled down by a vacuum, or tissue culture medium aspiration off the top of the cell population, or removed by aspiration or vacuum removal from the bottom of the vessel.

Contacting the population of cells with the volume of aqueous solution can be performed by gas propelling the aqueous solution to form a spray. The gas can include nitrogen, ambient air, or an inert gas. The spray can include discrete units of volume ranging in size from, 1 nm to 100 µm, e.g., 30-100 µm in diameter. The spray includes discrete units of volume with a diameter of about 30-50 µm. A total volume of aqueous solution of 20 µl can be delivered in a spray to a cell-occupied area of about 1.9 cm$^2$, e.g., one well of a 24-well culture plate. A total volume of aqueous solution of 10 µl is delivered to a cell-occupied area of about 0.95 cm$^2$, e.g., one well of a 48-well culture plate. Typically, the aqueous solution includes a payload to be delivered across a cell membrane and into cell, and the second volume is a buffer or culture medium that does not contain the payload. Alternatively, the second volume (buffer or media) can also contain payload. In some embodiments, the aqueous solution includes a payload and an alcohol, and the second volume does not contain alcohol (and optionally does not contain payload). The population of cells can be in contact with said aqueous solution for 0.1-10 minutes prior to adding a second volume of buffer or culture medium to submerse or suspend said population of cells. The buffer or culture medium can be phosphate buffered saline (PBS). The population of cells can be in contact with the aqueous solution for 2 seconds to 5 minutes prior to adding a second volume of buffer or culture medium to submerse or suspend the population of cells. The population of cells can be in contact with the aqueous solution, e.g., containing the payload, for 30 seconds to 2 minutes prior to adding a second volume of buffer or culture medium, e.g., without the payload, to submerse or suspend the population of cells. The population of cells can be in contact with a spray for about 1-2 minutes prior to adding the second volume of buffer or culture medium to submerse or suspend the population of cells. During the time between spraying of cells and addition of buffer or culture medium, the cells remain hydrated by the layer of moisture from the spray volume.

The aqueous solution can include an ethanol concentration of 5 to 30%. The aqueous solution can include one or more of 75 to 98% H$_2$O, 2 to 45% ethanol, 6 to 91 mM sucrose, 2 to 35 mM KCl, 2 to 35 mM ammonium acetate, and 1 to 14 mM (4-(2-hydroxyethyl)-1-piperazineethanesulfonic acid) (HEPES).

The population of cells can include adherent cells or non-adherent cells. The adherent cells can include at least one of primary mesenchymal stem cells, fibroblasts, monocytes, macrophages, lung cells, neuronal cells, fibroblasts, human umbilical vein (HUVEC) cells, Chinese hamster ovary (CHO) cells, and human embryonic kidney (HEK) cells or immortalized cells, such as cell lines. The population of cells can include non-adherent cells. The non-adherent cells can include at least one of primary hematopoietic stem cell (HSC), T cells, natural killer (NK) cells, cytokine-induced killer (CIK) cells, human cord blood CD34+ cells, B cells, or cell lines such as JurkatT cell line.

The payload can include a small chemical molecule, a peptide or protein, or a nucleic acid. The small chemical molecule can be less than 1,000 Da. The chemical molecule can include MitoTracker® Red CMXRos, propidium iodide, methotrexate, and/or DAPI (4',6-diamidino-2-phenylindole). The peptide can be about 5,000 Da. The peptide can include ecallantide under trade name Kalbitor, is a 60 amino acid polypeptide for the treatment of hereditary angioedema and in prevention of blood loss in cardiothoracic surgery), Liraglutide (marketed as the brand name Victoza, is used for the treatment of type II diabetes, and Saxenda for the treatment of obesity), and Icatibant (trade name Firazyer, a peptidomimetic for the treatment of acute attacks of hereditary angioedema). The small-interfering ribonucleic acid (siRNA) molecule can be about 20-25 base pairs in length, or can be about 10,000-15,000 Da. The siRNA molecule can reduces the expression of any gene product, e.g., knockdown of gene expression of clinically relevant target genes or of model genes, e.g., glyceraldehyde-3phosphate dehydrogenase (GAPDH) siRNA, GAPDH siRNA-FITC, cyclophilin B siRNA, and/or lamin siRNA. Protein therapeutics can include peptides, enzymes, structural proteins, receptors, cellular proteins, or circulating proteins, or fragments thereof. The protein or polypeptide be about 100-500,000 Da, e.g., 1,000-150,000 Da. The protein can include any therapeutic, diagnostic, or research protein or peptide, e.g., beta-lactoglobulin, ovalbumin, bovine serum albumin (BSA), and/or horseradish peroxidase. In other examples, the protein can include a cancer-specific apoptotic protein, e.g., Tumor necrosis factor-related apoptosis inducing protein (TRAIL).

An antibody is generally be about 150,000 Da in molecular mass. The antibody can include an anti-actin antibody, an anti-GAPDH antibody, an anti-Src antibody, an anti-Myc ab, and/or an anti-Raf antibody. The antibody can include a green fluorescent protein (GFP) plasmid, a GLuc plasmid and, and a BATEM plasmid. The DNA molecule can be greater than 5,000,000 Da. In some examples, the antibody can be a murine-derived monoclonal antibody, e.g., ibritumomab tiuxetin, muromomab-CD3, tositumomab, a human antibody, or a humanized mouse (or other species of origin) antibody. In other examples, the antibody can be a chimeric monoclonal antibody, e.g., abciximab, basiliximab, cetuximab, infliximab, or rituximab. In still other examples, the antibody can be a humanized monoclonal antibody, e.g., alemtuzamab, bevacizumab, certolizumab pegol, daclizumab, gentuzumab ozogamicin, trastuzumab, tocilizumab, ipilimumamb, or panitumumab. The antibody can comprise an antibody fragment, e.g., abatecept, aflibercept, alefacept, or etanercept. The invention encompasses not only an intact monoclonal antibody, but also an immunologically-active antibody fragment, e.g., a Fab or (Fab)2 fragment; an engineered single chain Fv molecule; or a chimeric molecule, e.g., an antibody which contains the binding specificity of one antibody, e.g., of murine origin, and the remaining portions of another antibody, e.g., of human origin.

The payload can include a therapeutic agent. A therapeutic agent, e.g., a drug, or an active agent", can mean any compound useful for therapeutic or diagnostic purposes, the term can be understood to mean any compound that is administered to a patient for the treatment of a condition. Accordingly, a therapeutic agent can include, proteins, peptides, antibodies, antibody fragments, and small molecules. Therapeutic agents described in U.S. Pat. No. 7,667,004 (incorporated herein by reference) can be used in the methods described herein. The therapeutic agent can include at least one of cisplatin, aspirin, statins (e.g., pitavastatin, atorvastatin, lovastatin, pravastatin, rosuvastatin, simvastatin, promazine HCl, chloropromazine HCl, thioridazine HCl, Polymyxin B sulfate, chloroxine, benfluorex HCl and phenazopyridine HCl), and fluoxetine. The payload can include a diagnostic agent. The diagnostic agent can include a detectable label or marker such as at least one of methylene blue, patent blue V, and indocyanine green. The payload can include a fluorescent molecule. The payload can include a detectable nanoparticle. The nanoparticle can include a quantum dot.

The population of cells can be substantially confluent, such as greater than 75 percent confluent. Confluency of cells refers to cells in contact with one another on a surface. For example, it can be expressed as an estimated (or counted) percentage, e.g., 10% confluency means that 10% of the surface, e.g., of a tissue culture vessel, is covered with cells, 100% means that it is entirely covered. For example, adherent cells grow two dimensionally on the surface of a tissue culture well, plate or flask. Non-adherent cells can be spun down, pulled down by a vacuum, or tissue culture medium aspiration off the top of the cell population, or removed by aspiration or vacuum removal from the bottom of the vessel. The population of cells can form a monolayer of cells.

The alcohol can be selected from methanol, ethanol, isopropyl alcohol, butanol and benzyl alcohol. The salt can be selected from NaCl, KCl, $Na_2HPO_4$, $KH_2PO_4$, and $C_2H_3O_2NH$. The sugar can include sucrose. The buffering agent can include 4-2-(hydroxyethyl)-1-piperazineethanesulfonic acid.

The present subject matter relates to a method for delivering molecules across a plasma membrane. The present subject matter finds utility in the field of intra-cellular delivery, and has application in, for example, delivery of molecular biological and pharmacological therapeutic agents to a target site, such as a cell, tissue, or organ. The method of the present subject matter comprises introducing the molecule to an aqueous composition to form a matrix; atomizing the matrix into a spray; and contacting the matrix with a plasma membrane.

This present subject matter relates to a composition for use in delivering molecules across a plasma membrane. The present subject matter finds utility in the field of intra-cellular delivery, and has application in, for example, delivery of molecular biological and pharmacological therapeutic agents to a target site, such as a cell, tissue, or organ. The composition of the present subject matter comprises an alcohol; a salt; a sugar; a buffering agent; and ammonium acetate.

In some implementations, demonstrated is a permeabilisation technique that facilitates intracellular delivery of molecules independent of the molecule and cell type. Nanoparticles, small molecules, nucleic acids, proteins and other molecules can be efficiently delivered into suspension cells or adherent cells in situ, including primary cells and stem cells, with low cell toxicity and the technique is compatible with high throughput and automated cell-based assays.

The example methods described herein include a payload, wherein the payload includes an alcohol. By the term "an alcohol" is meant a polyatomic organic compound including a hydroxyl (—OH) functional group attached to at least one carbon atom. The alcohol may be a monohydric alcohol and may include at least one carbon atom, for example methanol. The alcohol may include at least two carbon atoms (e.g. ethanol). In other aspects, the alcohol comprises at least three carbons (e.g. isopropyl alcohol). The alcohol may include at least four carbon atoms (e.g., butanol), or at least seven carbon atoms (e.g., benzyl alcohol). The example payload may include no more than 50% (v/v) of the alcohol, more preferably, the payload comprises 2-45% (v/v) of the alcohol, 5-40% of the alcohol, and 10-40% of the alcohol. The payload may include 20-30% (v/v) of the alcohol.

Most preferably, the payload includes 25% (v/v) of the alcohol. Alternatively, the payload can include 2-8% (v/v) of the alcohol, or 2% of the alcohol. The alcohol may include ethanol and the payload comprises 5, 10, 20, 25, 30 or 40% (v/v) of the ethanol. Example methods may include methanol as the alcohol, and the payload may include 5, 10, 20, 25, 30, or 40% (v/v) of the methanol. The payload may include 2-45% (v/v) of methanol, 20-30% (v/v), or 25% (v/v) methanol. Preferably, the payload includes 20-30% (v/v) of methanol. Further alternatively, the alcohol is butanol and the payload comprises 2, 4, or 8% (v/v) of the butanol.

In some aspects of the present subject matter, the payload is in a hypotonic solution or buffer. The payload solution may have an osmotic concentration of 171 mOsm/L. According to example methods, the payload solution has an osmotic concentration of 171 mOsm/L at room temperature.

According to the present subject matter, the payload may include at least one salt. The salt may be selected from NaCl, KCl, $Na_2HPO_4$, $C_2H_3O_2NH_4$ and $KH_2PO_4$. According to example methods, the payload includes each of NaCl, KCl, $Na_2HPO_4$, and $KH_2PO_4$. The payload may include less than 46 mM salt. Further, the payload includes 2-35 mM salt, or 10-15 mM salt (e.g., 12 mM salt). According to example methods, the salt is KCl and the payload includes 2.4, 4.8, 7.2, 9.6, 12, 24, 28.8, or 33.6 mM KCl, and more preferably 12 mM KCl.

According to example methods of the present subject matter, the payload may include a sugar (e.g., a sucrose, or a disaccharide). According to example methods, the payload comprises less than 121 mM sugar, 6-91 mM, or 26-39 mM sugar. Still further, the payload includes 32 mM sugar (e.g., sucrose). Optionally, the sugar is sucrose and the payload comprises 6.4, 12.8, 19.2, 25.6, 32, 64, 76.8, or 89.6 mM sucrose.

According to example methods of the present subject matter, the payload may include a buffering agent (e.g. a weak acid or a weak base). The buffering agent may include a zwitterion. According to example methods, the buffering agent is 4-(2-hydroxyethyl)-1-piperazineethanesulfonic acid. The payload may comprise less than 19 mM buffering agent (e.g., 1-15 mM, or 4-6 mM or 5 mM buffering agent). According to example methods, the buffering agent is 4-(2-hydroxyethyl)-1-piperazineethanesulfonic acid and the payload comprises 1, 2, 3, 4, 5, 10, 12, 14 mM 4-(2-hydroxyethyl)-1-piperazineethanesulfonic acid. Further preferably, the payload comprises 5 mM 4-(2-hydroxyethyl)-1-piperazineethanesulfonic acid.

According to example methods of the present subject matter, the payload includes ammonium acetate. The payload may include less than 46 mM ammonium acetate (e.g., between 2-35 mM, 10-15 mM, ore 12 mM ammonium acetate). The payload may include 2.4, 4.8, 7.2, 9.6, 12, 24, 28.8, or 33.6 mM ammonium acetate.

The methods described herein include a second aspect of the present subject matter, where a second payload (e.g. an aqueous solution) including 68 mM NaCl, 1.4 mM KCl, 5 mM $Na_2HPO_4$, and 0.9 mM $KH_2PO_4$ is provided. The pH of the second payload may be pH 7.4.

The volume of aqueous solution performed by gas propelling the aqueous solution may include compressed air (e.g. ambient air), other implementations may include inert gases, for example, helium, neon, and argon.

In certain aspects of the present subject matter, the population of cells may include adherent cells (e.g., lung, kidney, immune cells such as macrophages) or non-adherent cells (e.g., suspension cells).

In certain aspects of the present subject matter, the population of cells may be substantially confluent, and substantially may include greater than 75 percent confluent. In preferred implementations, the population of cells may form a single monolayer.

According to example methods, the payload to be delivered has an average molecular weight of up to 20,000,000 Da. In some examples, the payload to be delivered can have an average molecular weight of up to 2,000,000 Da. In some implementations, the payload to be delivered may have an average molecular weight of up to 150,000 Da. In further implementations, the payload to be delivered has an average molecular weight of up to 15,000 Da, 5,000 Da or 1,000 Da.

The payload to be delivered across the plasma membrane of a cell may include a small chemical molecule, a peptide or protein, a polysaccharide or a nucleic acid or a nanoparticle. A small chemical molecule may be less than 1,000 Da, peptides may have molecular weights about 5,000 Da, siRNA may have molecular weights around 15,000 Da, antibodies may have molecular weights of about 150,000 Da and DNA may have molecular weights of greater than or equal to 5,000,000 Da.

According to example methods, the payload includes 3.0-150.0 µM of a molecule to be delivered, more preferably, 6.6-150.0 µM molecule to be delivered (e.g. 3.0, 3.3, 6.6, or 150.0 µM molecule to be delivered). In some implementations, the payload to be delivered has an average molecular weight of up to 15,000 Da, and the payload includes 3.3 µM molecules to be delivered.

According to example methods, the payload to be delivered has an average molecular weight of up to 15,000 Da, and the payload includes 6.6 µM to be delivered. In some implementations, the payload to be delivered has an average molecular weight of up to 1,000 Da, and the payload includes 150.0 µM to be delivered.

Aspects of the present subject matter provide for the payload to be delivered to have an average molecular weight of up to 15,000 Da. The payload may include an aqueous solution having an osmotic concentration of 171 mOsm/L at room temperature and a pH of about 7.4; and including 25% (v/v) of ethanol; 12 mM KCl; 32 mM sucrose; 5 mM 4-(2-hydroxyethyl)-1-piperazineethanesulfonic acid; 12 mM ammonium acetate; and 6.6 µM molecules to be delivered.

According to example methods, the payload to be delivered has an average molecular weight of up to 15,000 Da. The payload may include an aqueous solution having an osmotic concentration of 171 mOsm/L at room temperature and a pH of about 7.4; and includes 20% (v/v) of methanol; 12 mM KCl; 32 mM sucrose; 5 mM 4-(2-hydroxyethyl)-1-piperazineethanesulfonic acid; 12 mM ammonium acetate; and 6.6 µM molecules to be delivered.

In some implementations, the molecule to be delivered has an average molecular weight of up to 15,000 Da. The payload may include an aqueous solution having an osmotic concentration of 171 mOsm/L at room temperature and a pH of about 7.4; and includes 25% (v/v) of methanol; 12 mM KCl; 32 mM sucrose; 5 mM 4-(2-hydroxyethyl)-1-piperazineethanesulfonic acid; 12 mM ammonium acetate; and 6.6 µM molecules to be delivered.

According to example methods, the payload to be delivered has an average molecular weight of up to 1,000 Da, the payload includes an aqueous solution having an osmotic concentration of 171 mOsm/L at room temperature and a pH of about 7.4; and includes 25% (v/v) of ethanol; 12 mM KCl; 32 mM sucrose; 5 mM 4-(2-hydroxyethyl)-1-piperazineethanesulfonic acid; 12 mM ammonium acetate; and 150 µM molecules to be delivered.

In some implementations, the molecule to be delivered has an average molecular weight of up to 1,000 Da. According to example methods, the payload may include an aqueous solution having an osmotic concentration of 171 mOsm/L at room temperature and a pH of about 7.4; and includes 25% (v/v) of ethanol; 34 mM NaCl. 0.7 mM KCl, 2.5 mM $Na_2HPO_4$, and 0.5 mM $KH_2PO_4$; and 150.0 µM molecules to be delivered.

The payload to be delivered can have an average molecular weight of up to 1,000 Da. According to example methods, the payload can include an aqueous solution having an osmotic concentration of 171 mOsm/L at room temperature and a pH of about 7.4; and can include 2% (v/v) of butanol; 12 mM KCl; 32 mM sucrose; 5 mM 4-(2-hydroxyethyl)-1-piperazineethanesulfonic acid; 12 mM ammonium acetate; and 150 µM molecules to be delivered.

According to further aspects of the present subject matter, a method for delivering molecules of more than one molecular weight across a plasma membrane is provided; the method including the steps of: introducing the molecules of more than one molecular weight to an aqueous solution; and contacting the aqueous solution with a plasma membrane.

In some implementations, the method includes introducing a first molecule having a first molecular weight and a second molecule having a second molecular weight to the payload, wherein the first and second molecules may have different molecular weights, or wherein the first and second molecules may have the same molecular weights. According to example methods, the first and second molecules may be different molecules.

In some implementations, the payload to be delivered may include a therapeutic agent, or a diagnostic agent, including, for example, cisplatin, aspirin, various statins (e.g., pitavastatin, atorvastatin, lovastatin, pravastatin, rosuvastatin, simvastatin, promazine HCl, chloropromazine HCl, thioridazine HCl, Polymyxin B sulfate, chloroxine, benfluorex HCl and phenazopyridine HCl), and fluoxetine. Other therapeutic agents include antimicrobials (aminoclyclosides (e.g. gentamicin, neomycin, streptomycin), penicillins (e.g., amoxicillin, ampicillin), glycopeptides (e.g., avoparcin, vancomycin), macrolides (e.g., erythromycin, tilmicosin, tylosin), quinolones (e.g., sarafloxacin, enrofloxin), streptogramins (e.g., viginiamycin, quinupristin-dalfoprisitin), carbapenems, lipopeptides, oxazolidinones, cycloserine, ethambutol, ethionamide, isoniazrid, para-aminosalicyclic acid, and pyrazinamide). In some examples, an anti-viral (e.g., Abacavir, Aciclovir, Enfuvirtide, Entecavir, Nelfinavir, Nevirapine, Nexavir, Oseltamivir Raltegravir, Ritonavir, Stavudine, and Valaciclovir). The therapeutic may include a protein-based therapy for the treatment of various diseases, e.g., cancer, infectious diseases, hemophilia, anemia, multiple sclerosis, and hepatitis B or C.

Additional exemplary payloads can also include detectable markers or labels such as methylene blue, Patent blue V, and Indocyanine green.

The methods described herein may also include the payload including of a detectable moiety, or a detectable nanoparticle (e.g., a quantum dot). The detectable moiety may include a fluorescent molecule or a radioactive agent (e.g., $^{125}I$) When the fluorescent molecule is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, p-phthaldehyde and fluorescamine. The molecule can also be detectably labeled using fluorescence emitting metals such as $^{152}Eu$, or others of the lanthanide series. These metals can be attached to the molecule using such metal chelating groups as diethylenetriaminepentacetic acid (DTPA) or ethylenediaminetetraacetic acid (EDTA). The molecule also can be detectably labeled by coupling it to a chemiluminescent compound. The presence of the chemiluminescent-tagged molecule is then determined by detecting the presence of luminescence that arises during the course of chemical reaction. Examples of particularly useful chemiluminescent labeling compounds are luminol, isoluminol, theromatic acridinium ester, imidazole, acridinium salt and oxalate ester.

In one aspect, the present subject matter describes cells attached to a solid support, (e.g., a strip, a polymer, a bead, or a nanoparticle). The support or scaffold may be a porous or non-porous solid support. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present subject matter. The support material may have virtually any possible structural configuration. Thus, the support configuration may be spherical, as in a bead, or cylindrical, as in the inside surface of a test tube, or the external surface of a rod. Alternatively, the surface may be flat such as a sheet, or test strip, etc. Preferred supports include polystyrene beads.

In other aspects, the solid support comprises a polymer, to which cells are chemically bound, immobilized, dispersed, or associated. A polymer support may be a network of polymers, and may be prepared in bead form (e.g., by suspension polymerization). The cells on such a scaffold can be sprayed with payload containing aqueous solution according to the invention to deliver desired compounds to the cytoplasm of the scaffold. Exemplary scaffolds include stents and other implantable medical devices or structures.

The present subject matter further relates to apparatus, systems, techniques and articles for delivery of payloads across a plasma membrane. The present subject matter also relates to an apparatus for delivering payloads such as proteins or protein complexes across a plasma membrane. The current subject matter may find utility in the field of intra-cellular delivery, and has application in, for example, delivery of molecular biological and pharmacological therapeutic agents to a target site, such as a cell, tissue, or organ.

In some implementations, an apparatus for delivering a payload across a plasma membrane can include an atomizer having at least one atomizer emitter and a support oriented relative to the atomizer. The method further comprises the step of atomizing the payload prior to contacting the plasma membrane with the payload.

The atomizer can be selected from a mechanical atomizer, an ultrasonic atomizer, an electrospray, a nebuliser, and a Venturi tube. The atomizer can be a commercially available atomizer. The atomizer can be an intranasal mucosal atomization device. The atomizer can be an intranasal mucosal atomization device commercially available from LMA Teleflex of NC, USA. The atomizer can be an intranasal mucosal atomization device commercially available from LMA Teleflex of NC, USA under catalogue number MAD300.

The atomizer can be adapted to provide a colloid suspension of particles having a diameter of 30-100 μm prior to contacting the plasma membrane with the payload. The atomizer can be adapted to provide a colloid suspension of particles having a diameter of 30-80 μm. The atomizer can be adapted to provide a colloid suspension of particles having a diameter of 50-80 μm.

The atomizer can include a gas reservoir. The atomizer can include a gas reservoir with the gas maintained under pressure. The gas can be selected from air, carbon dioxide, and helium. The gas reservoir can include a fixed pressure head generator. The gas reservoir can be in fluid communication with the atomizer emitter. The gas reservoir can include a gas guide, which can be in fluid communication with the atomizer emitter. The gas guide can be adapted to allow the passage of gas therethrough. The gas guide can include a hollow body. The gas guide can be a hollow body having open ends. The gas guide can include a hollow body having first and second open ends. The gas guide can be a hollow body having first and second opposing open ends. The diameter of the first open end can be different to the diameter of the second open end. The diameter of the first open end can be different to the diameter of the second open end. The diameter of the first open end can be greater than the diameter of the second open end. The first open end can be in fluid communication with the gas reservoir. The second open end can be in fluid communication with the atomizer emitter.

The apparatus can include a sample reservoir. The sample reservoir can be in fluid communication with the atomizer. The sample reservoir can be in fluid communication with the atomizer emitter. The gas reservoir and the sample reservoir can both be in fluid communication with the atomizer emitter.

The apparatus can include a sample valve located between the sample reservoir and the gas reservoir. The apparatus can include a sample valve located between the sample reservoir and the gas guide. The sample valve can be adapted to adjust the sample flow from the sample reservoir. The sample valve can be adapted to allow continuous or semi-continuous sample flow. The sample valve can be adapted to allow semi-continuous sample flow. The sample valve can be adapted to allow semi-continuous sample flow of a defined amount. The sample valve is adapted to allow semi-continuous sample flow of 0.5-100 μL. The sample valve can be adapted to allow semi-continuous sample flow of 10 μL. The sample valve can be adapted to allow semi-continuous sample flow of 1 μL to an area of 0.065-0.085 $cm^2$.

The atomizer and the support can be spaced apart. The support can include a solid support. The support can include a plate including sample wells. The support can include a plate including sample wells selected from 1, 6, 9, 12, 24, 48, 384, and 1536 wells. The solid support can be formed from an inert material. The solid support can be formed from a plastic material, or a metal or metal alloy, or a combination thereof. The support can include a heating element. The support can include a resistive element. The support can be reciprocally mountable to the apparatus. The support can be reciprocally movable relative to the apparatus. The support can be reciprocally movable relative to the atomizer. The support can be reciprocally movable relative to the atomizer emitter. The support can include a support actuator to reciprocally move the support relative to the atomizer. The support can include a support actuator to reciprocally move the support relative to the atomizer emitter. The support can include a support actuator to reciprocally move the support relative to the longitudinal axis of the atomizer emitter. The support can include a support actuator to reciprocally move the support transverse to the longitudinal axis of the atomizer emitter.

The longitudinal axis of the spray zone can be coaxial with the longitudinal axis or center point of the support and/or the circular well of the support, to which the payload is to be delivered. The longitudinal axis of the atomizer emitter can be coaxial with the longitudinal axis or center point of the support and/or the circular well of the support. The longitudinal axis of the atomizer emitter, the longitudinal axis of the support, and the longitudinal axis of the spray zone can be each coaxial. The longitudinal length of the spray zone may be greater than the diameter (may be greater than double) of the circular base of the spray zone (e.g., the area of cells to which the payload is to be delivered).

The apparatus can include a valve located between the gas reservoir and the atomizer. The valve can be an electromagnetically operated valve. The valve can be a solenoid valve. The valve can be a pneumatic valve. The valve can be located at the gas guide. The valve can be adapted to adjust the gas flow within the gas guide. The valve can be adapted to allow continuous or semi-continuous gas flow. The valve can be adapted to allow semi-continuous gas flow. The valve can be adapted to allow semi-continuous gas flow of a defined time interval. The valve can be adapted to allow semi-continuous gas flow of a one second time interval. The apparatus can include at least one filter. The filter can include a pore size of less than 10 µm. The filter can have a pore size of 10 µm. The filter can be located at the gas guide. The filter can be in fluid communication with the gas guide.

The apparatus can include at least one regulator. The regulator can be an electrical regulator. The regulator can be a mechanical regulator. The regulator can be located at the gas guide. The regulator can be in fluid communication with the gas guide. The regulator can be a regulating valve. The pressure within the gas guide can be 1.0-2.0 bar. The pressure within the gas guide can be 1.5 bar. The pressure within the gas guide can be 1.0-2.0 bar, and the distance between the atomizer and the support can be less than or equal to 31 mm. The pressure within the gas guide can be 1.5 bar, and the distance between the atomizer and the support can be 31 mm. The pressure within the gas guide can be 0.05 bar per millimeter distance between the atomizer and the support. The regulating valve can be adapted to adjust the pressure within the gas guide to 1.0-2.0 bar. The regulating valve cam be adapted to adjust the pressure within the gas guide to 1.5 bar. The or each regulating valve can be adapted to maintain the pressure within the gas guide at 1.0-2.0 bar. The or each regulating valve can be adapted to maintain the pressure within the gas guide at 1.5 bar.

The apparatus can include two regulators. The apparatus can include first and second regulators. The first and second regulator can be located at the gas guide. The first and second regulator can be in fluid communication with the gas guide. The first regulator can be located between the gas reservoir and the filter. The first regulator can be adapted to adjust the pressure from the gas reservoir within the gas guide to 2.0 bar. The first regulator can be adapted to maintain the pressure within the gas guide at 2.0 bar. The second regulator can be located between the filter and the valve.

The atomizer emitter can be adapted to provide a conical spray zone (e.g., a generally circular conical spray zone). The atomizer emitter can be adapted to provide a 30° conical spray zone. The apparatus further can include a microprocessor to control any or all parts of the apparatus. The microprocessor can be arranged to control any or all of the sample valve, the support actuator, the valve, and the regulator. The apparatus can include an atomizer having at least one atomizer emitter; and a support oriented relative to the atomizer; the atomizer can be selected from a mechanical atomizer, an ultrasonic atomizer, an electrospray, a nebuliser, and a Venturi tube. The atomizer can be adapted to provide a colloid suspension of particles having a diameter of 30-100 µm. The apparatus can include a sample reservoir and a gas guide, and a sample valve located between the sample reservoir and the gas guide. The sample valve can be adapted to allow semi-continuous sample flow of 10-100 µL.

The atomizer and the support can be spaced apart and define a generally conical spray zone there between; and the distance between the atomizer and the support can be approximately double the diameter of the circular base of the area of cells to which molecules are to be delivered; the distance between the atomizer and the support can be 31 mm and the diameter of the circular base of the area of cells to which molecules are to be delivered can be 15.5 mm. The apparatus can include a gas guide and the pressure within the gas guide is 1.0-2.0 bar. The apparatus can include at least one filter having a pore size of less than 10 µm.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Non-limiting embodiments of the present subject matter will now be described with reference to the accompanying drawings.

FIG. 3 is a process flow diagram illustrating a process of producing colloidal droplets for delivering a sample to the cytoplasm of one or more target cells.

FIG. 52 is a table illustrating approximate volume delivered per cell according to an example implementation of the currents subject matter.

FIG. 53 is a table illustrating approximate volume delivered per square micrometer of exposed cell surface area.

FIG. 54 is a table illustrating approximate average properties of some cell types.

FIG. 55 is a table showing experimentally calculated and measured areas of three different cell lines (A549, CHO, and MCSs).

Like reference symbols in the various drawings indicate like elements

DETAILED DESCRIPTION

The present subject matter provides for vector-free (e.g., viral vector-free) delivery of a payload across a plasma membrane. In particular, it has been discovered that intracellular delivery of materials can be achieved by contacting a cell (and/or population of cells) with an aqueous solution that includes an alcohol and the delivery materials (e.g., the payload). The alcohol acts to permeabilise the membrane to allow the payload to translocate across the membrane. But permanent or severe (e.g., irreversible) damage to the cell may occur (adversely affecting cell viability) when the volume of aqueous solution that contacts the cell is too large and/or exposure occurs for too long a time. Conversely, intracellular delivery of materials is not achieved when the volume of aqueous solution that contacts the cell is too small and/or exposure occurs for too short a time. Thus, to achieve delivery of a payload across a plasma membrane while maintaining cell viability, an appropriate volume of aqueous solution can be applied and/or the length of exposure can be controlled.

The appropriate volume of aqueous solution that is contacted to a population of cells can vary based on the intended application, for example, based on (e.g., be a function of) number of cells in the population, exposed cell surface area, cell size, makeup of the aqueous solution, payload, technique of contacting the aqueous solution to the population of cells, and the like. In some implementations, the volume of aqueous solution can be between $6.0 \times 10^{-7}$ and $7.4 \times 10^{-4}$ microliters per cell (additional ranges are described elsewhere herein). These ranges correspond to delivering between 0.5 microliters and 100 microliters of aqueous solution to a well in a 48 well plate having a population of cells arranged substantially in a monolayer (the cells having an average diameter of 30 micrometers and 15 micrometers, respectfully). The volume of aqueous solution can be between $2.6 \times 10^{-9}$ and $1.1 \times 10^{-6}$ microliter per square micrometer of exposed surface area of the population of cells (additional ranges are described elsewhere herein). These ranges correspond to delivering between 0.5 microliters and 100 microliters of aqueous solution to a well in a 24 well plate and a 48 well plate, respectfully, and having a population of cells arranged substantially in a monolayer.

Figure 56A:
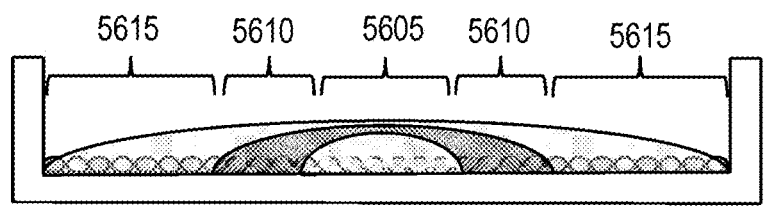
FIG. 56A is a cross-sectional view of an illustration of a well having a volume of aqueous solution applied using a pipette.

The technique for contacting the population of cells with the aqueous solution can vary. For example, the aqueous solution can be pipetted onto the population of cells (for example, when the cells are arranged in a well). For example, FIG. 56A is a cross-sectional view illustrating a well with a monolayer of cells having a volume of aqueous solution applied using a micropipette. When the aqueous solution is applied in this manner, it may be unevenly distributed over the area of the well and, as a result, cells located near the center of the well (the region indicated at 5605) are killed, while cells located near the outer edges of the well (the region indicated at 5615) remain viable but exhibit no update of the payload. Cells in a region 5610 between the inner and outer regions (5605 and 5615, respectively) remain viable while efficiently and reliably exhibiting uptake of the payload.

Figure 56B:
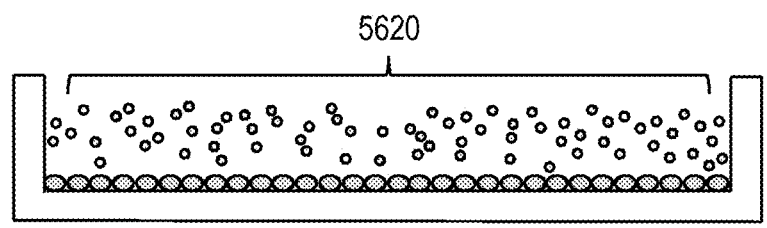
FIG. 56B is a cross-sectional view of an illustrations of a well having a volume of aqueous solution applied via a spray technique.

In some implementations, aqueous solution is sprayed onto the population of cells. For example, FIG. 56B is a cross-sectional view illustrating a well having a volume of aqueous solution applied via a spray technique. The spray can evenly distribute the aqueous solution over the area of the well (region indicated at 5620). Cells treated in this manner (and as further described in detail herein) remain viable while efficiently and reliably exhibiting uptake of payload across the cell membrane and into the cytoplasm of the cell. Spraying can provide a means for contacting a population of cells with the aqueous solution in a controlled manner and has been shown to improve efficiency of delivery of the payload and improve cell viability. The spray can be controlled to create discrete units (e.g., droplets) of volume that vary in size. For example, in an implementation, the discrete units of volume range from 30-100 µm in diameter. Other sizes are possible and some variations are described elsewhere herein.

Contacting of the population of cells with the aqueous solution (payload-containing) can be transient. In other words, the length of time that the aqueous solution contacts the population of cells can vary. For example, the length of time of exposure can be at least 6 seconds, 12 seconds, 30 seconds, and the like. Other lengths of time are possible and some variations are described elsewhere herein. Because over exposure of cells to the aqueous solution can lead to lower cell viability, the population of cells can be washed with a buffer or culture medium after being exposed to the aqueous solution. The buffer can include or not include the payload. The buffer may be alcohol free. The cells can be washed with the buffer or culture medium to submerse or suspend the population of cells. In some implementations, a gas may be blown across the cells to push the aqueous solution out of contact with the cells, although over exposure of cells to gas may dehydrate the cells and lead to lower cell viability.

The aqueous solution can include $H_2O$, an alcohol, and the payload. The alcohol can include methanol, ethanol, isopropyl alcohol, butanol or benzyl alcohol. The aqueous solution can also include one or more of a sugar, a salt and a buffering agent. The salt can be selected from NaCl, KCl, $Na_2HPO_4$ and $KH_2PO_4$. The sugar may include a disaccharide, (e.g., sucrose). The buffering agent may include a weak acid or a weak base and be a zwitterion (e.g., (4-(2-hydroxyethyl) piperazineethanesulfonic acid (hepes)). The aqueous solution also can include ammonium acetate. For example, the aqueous solution is a hypotonic buffer, e.g., as described by Medepalli et al., (Medepalli, K., et al., *Nanotechnology* 2013; 24:20, incorporated herein by reference in its entirety), 130 mM sucrose, 50 mM potassium chloride, 50 mM potassium acetate, 20 mM 4-(2-hydroxyethyl)-1-piperazineethanesulfonic acid (hepes), pH 7.4. In some examples, the buffer is modified to replace the potassium acetate with ammonium acetate. In some examples, the buffer used for payload delivery does not include saponin.

Components of the aqueous solution can serve to disrupt the plasma membrane of cells and allow for introduction of larger biological molecules across the plasma membrane. For example, alcohols dissolve lipids within the plasma membrane, detergents create pores within the plasma membrane, and enzymes digest proteins to create pores within the plasma membrane.

Payload can be delivered into the cytoplasm of the cell, as well as to specific cellular organelles (e.g., the nucleus and mitochondria). The payload can include any molecule suitable for and/or intended for delivery. Molecules targeting the mitochondria are beneficial in a number of diseases such as cancer and delivery of such molecules can be related to functions of mitochondria including energy production and apoptosis. For example, fluorescently labeled (e.g., tagged) molecules can be used to visualize the presence and location of mitochondrial components, molecules that target mitochondrial permeability transition (MPT) (e.g., chemical inhibitors or peptides that deplete endogenous inhibitors of permeability transition pore complex (PTPC) opening), small chemical molecules that trigger mitochondrial permeability transition (MPT), ligands that modulate the adenine nucleotide translocase (ANT), compounds that induce the overproduction of reactive oxygen species (ROS), molecules that reverse the hyperglycolytic state of cancer cells, molecules that prime cancer cells to the induction of cell death, and the like.

The payload can include but is not limited to small chemical molecules, peptides, polypeptides, nucleic acid molecules antibodies, and DNA (e.g. plasmid DNA). Exemplary small chemical molecules include dextrans of increasing sizes up to 2,000,000 Da, including 3 kDa dextran, 40 kDa dextran, 70 kDa dextran, or 500 kDa dextran, propidium iodide, 4',6-diamidino-2-phenylindole (DAPI), phallotoxin, MitoTracker Red or any combination thereof (for example, MitoTracker Red can be co-delivered with phallotoxin, as can 10 kDa dextran-Alexa488 and DAPI), methotrexate. Exemplary peptides, polypeptides, and proteins or fragments thereof include proteins of increasing size up to 500 kDa, including β-lactoglobulin, horseradish peroxidase, ovalbumin, bovine serum albumin, catalase and apoferritin). Exemplary peptides can include ecallantide, liraglutide and icatibant. Exemplary nucleic acids may refer to polynucleotides such as deoxyribonucleic acid (DNA), and where appropriate ribonucleic acid (RNA). The term also includes equivalents, analogs of either DNA or RNA made from nucleotide analogs, and as applicable to the present subject matter, may be single (sense or antisense) and double-stranded polynucleotides. Further nucleic acid examples can include, an siRNA molecule (e.g., a GAPDH siRNA-FITC), a cyclophilin B siRNA, or a lamin siRNA molecule), a double stranded nucleic acid molecule, for example a double stranded RNA molecule, a single stranded nucleic acid molecule, or an isolated nucleic acid molecule). Example DNA payloads of the current subject matter include DNA samples greater than or equal to 5,000,000 Da (e.g., pGFP, pGLuc, and p BATEM). Exemplary antibodies of the present subject matter can include an anti-actin antibody, an anti-GAPDH (Glyceraldehyde 3-phosphate dehydrogenase) antibody, an anti-Src (proto-oncogene tyrosine-protein kinase Src) antibody, an anti-Myc antibody or an anti-Raf antibody. The antibodies of the present invention can be polyclonal antisera or monoclonal antibodies. The present subject matter can encompass not only an intact monoclonal antibody, but also an antibody fragment, e. g., a Fab or (Fab)2 fragment; an engineered single chain FV molecule; or a chimeric molecule, e.g., an antibody which contains the binding specificity of one antibody, e.g., of murine origin, and the remaining portions of another antibody, e.g., of human origin. The antibody may be a humanized antibody, wherein the antibody is from a non-human species, whose protein sequence has been modified to increase their similarity to antibody variants produced naturally in humans. Generally, a humanized antibody has one or more amino acid residues introduced into it from a source which is non-human. These non-human amino acid residues are referred to herein as "import" residues, which are typically taken from an "import" antibody domain, particularly a variable domain.

The population of cells may include adherent cells that grow to form a confluent (e.g., 75% confluent) monolayer on the growth surface area of the culture plate. Adherent cells can refer to cells, cell lines, and cell systems, whether prokaryotic or eukaryotic. Examples of cells that can be grown as adherent cells are liver or liver-derived (e.g., primary hepatocytes and liver epithelial cells), epithelial cells, endothelial cells, neuronal cells, mesenchymal cells, pancreatic cells, skeletal muscle cells, cardiomyocytes, carcinoma-derived cells, bone marrow cells, islets of Langerhans, adrenal medulla cells, osteoblasts, osteoclasts, T-lymphocytes, neurons, glial cells, ganglion cells, retinal cells, lung cells (e.g., A549 cells), fibroblasts, human umbilical vein cells (HUVEC), fibroblasts, ovary cells (e.g., Chinese hamster ovary cells), embryonic kidney cells (e.g., human embryonic kidney cells), and myoblast cells. Stem cells can also be used (e.g., primary mesenchymal stem cells, neuronal stem cells, induced pluripotent stem cells, hematopoietic stem cells, mouse embryonic stem cells, and human embryonic stem cells).

The population of cells can also include non-adherent (e.g., suspension) cells. Exemplary non-adherent cells include stem cells (for example, hematopoietic stem cells), progenitor cells (for example hematopoietic progenitor cells), T cells, natural killer (NK) cells, cytokine-induced killer (CIK) cells, human cord blood CD34+ cells, B cells and Jurkat cells.

The population of cells, as described herein, have been described according to size (e.g., small, medium, and large), based on their calculated diameter, as determined by the American Type Culture Collection (ATCC), Celeromics Technologies and other molecular biology references. As referred to herein and in a non-limiting manner, in some examples, a small cell has a diameter up to 10 μm (e.g., splenocytes or small neurons), a medium cell has a diameter between 10 μm and 20 μm (e.g., A549 cells, CHO cells or MCF7 cells), and a large cell has a dimeter greater than 20 μm (e.g., K562 cells, and MSCs). Generally, the categories (ranges) are not meant to be limiting, and experimental conditions can affect the measured diameter of the cell.

In some implementations, the population of cells can be located on a three dimensional scaffold, which can be sprayed (or payload can be delivered to the cells using another technique). The three dimensional scaffold may be for use in ex vivo or in vivo use. It also contemplated that other aspects of the current subject matter can apply ex vivo or in vivo.

Determining Volume as Function of Exposed Surface Area and Number of Cells

As described more fully herein, efficient delivery of payloads to A549 cells in a well of a 48 well plate was achieved by contacting 10 μL of aqueous solution to the population of cells via a spray technique and incubating the cells after approximately 2 minutes with a buffer solution. However, delivery can be achieved by contacting between 0.5 μL and 100 μL aqueous solution to cells of varying types in a well of a 48 well plate, for example, contacting 0.5 μL, 5 μL, 10 μL, 15 μL, or 100 μL of aqueous solution to a population of cells. But delivery is not limited to using a well in a 48 (or 24) well plate and instead the volume of aqueous solution to be contacted with a population of cells can be a function of exposed cell surface area and/or number of cells in the population. For example, to determine the volume of aqueous solution to deliver per cell, the following describes a non-limiting example method of computing the volume delivered per cell and per micrometer of exposed cell surface area.

Exemplary adherent cells have an average diameter of about 10-30 μm. For example, A549 cells have an average diameter of 15 μm (corresponding to 0.015 cm). Thus the average area of A549 cells is about $1.8 \times 10^{-6}$ cm$^2$. The area in a single well of a standard 48-well cell culture plate includes a growth area of 0.95 cm$^2$. Thus the number of cells (e.g., A549 cells with a diameter of 15 μM is approximately about 500,000-500,500 cells (e.g., 537, 691 cells), assuming 100% confluence. As an example, 10 μL of the aqueous solution is delivered per well, thus approximately $1.9 \times 10^{-5}$ μL of aqueous solution were delivered to each cell (e.g., A549 cells). Accordingly, about $1.9 \times 10^{-5}$ microliters per cell was contacted with the population of cells. Ranges of aqueous volume delivered per cell was determined using aqueous volumes (e.g., 0.5 μL, 5 μL, 10 μL, 15 μL and 100 μL) and various cell sizes (e.g., approximately 30 μm (MSCs), approximately 15 μm (A549 cells), and approximately 10 μm (U266 cells). These and additional example values are shown in FIG. 52 and FIG. 53.

As an exemplary calculation of the volume delivered as a function of exposed surface are of the population of cells, the growth area of the cell culture plate was utilized. The surface area of a single well within a 24 well plate is 19000 μm$^2$ (and 9500 μm$^2$ in a 48 well plate, and 3200 μm$^2$ in a 96 well plate). The range of aqueous volume delivered per well was determined using aqueous volumes including 0.5 μL, 5 μL, 10 μL, 15 μL and 100 μL. Thus the volume of aqueous solution delivered (e.g., 10 μL per well) per square micrometer includes $5.3 \times 10^{-1}$ μL per well in a 24 well plate, $1.1 \times 10^{-3}$ μL per well in a 48 well plate and $3.1 \times 10^{-3}$ μL per well in a 96 well plate. These and additional example values are shown in FIG. 52. Additional Tables illustrating properties of some example cells are shown in FIG. 53.

Aqueous Solution and Delivery

The aqueous solution (also referred to herein as the composition) includes an alcohol selected from methanol, ethanol, isopropyl alcohol, butanol, and benzyl alcohol. The composition can include no more than 50% (v/v) of the alcohol. In certain embodiments, the alcohol is ethanol and the composition includes 5, 10, 20, 25, 30, or 40% (v/v) of the ethanol. Alternatively, the alcohol is methanol and the composition includes 5, 10, 20, 25, 30, or 40% (v/v) of the methanol. Further, the alcohol can be butanol and the composition includes 2, 4, or 8% (v/v) of the butanol. In preferred embodiments, the composition is an aqueous solution including the alcohol. The composition is preferably hypotonic, having an osmotic concentration of 171 mOsm/L at room temperature and a pH of about 7.4, and including at least one salt is selected from NaCl, KCl, Na$_2$HPO$_4$, and KH$_2$PO$_4$. In preferred embodiments, the salt is KCl and the composition includes 2.4, 4.8, 7.2, 9.6, 12, 24, 28.8, or 33.6 mM KCl. The composition can include a sugar, which can be sucrose and the composition can include 6.4, 12.8, 19.2, 25.6, 32, 64, 76.8, or 89.6 mM sucrose. In such preferred embodiments, the composition additionally includes a buffering agent, which can be selected from a weak acid or a weak base. In a preferred embodiment, the buffering agent is 4-(2-hydroxyethyl)-1-piperazineethanesulfonic acid and the composition includes 1, 2, 3, 4, 5, 10, 12, 14 mM 4-(2-hydroxyethyl)-1-piperazineethanesulfonic acid. Additionally, the composition can include ammonium acetate, for example, 2.4, 4.8, 7.2, 9.6, 12, 24, 28.8, or 33.6 mM ammonium acetate.

The present method can be used to deliver molecules having an average molecular weight of up to 2,000,000 Da, such as an average molecular weight of up to 150,000 Da, an average molecular weight of up to 15,000 Da, an average molecular weight of up to 5,000 Da, and/or an average molecular weight of up to 1,000 Da.

The introducing step of the method can include introducing 3.0-150.0 µM molecules to be delivered, optionally 3.3-150.0 µM, further optionally 6.6-150.0 µM molecules to be delivered. Optionally, the introducing step of the method includes introducing 3.0, 3.3, 6.6, or 150.0 µM molecules to be delivered. When the molecule to be delivered has an average molecular weight of up to 15,000 Da, the introducing step can include introducing 3.3 µM molecules to be delivered, alternatively 6.6 µM molecules to be delivered. Alternatively, when the molecule to be delivered has an average molecular weight of up to 1,000 Da, the introducing step includes introducing 150 µM molecules to be delivered. The amount of molecule introduced in the introducing step can be selected.

In a certain embodiment, the molecule to be delivered has an average molecular weight of up to 15,000 Da; and the method includes introducing 6.6 µM molecules to be delivered to a composition including an aqueous solution having an osmotic concentration of 171 mOsm/L at room temperature and a pH of about 7.4; and including 25% (v/v) of ethanol; 12 mM KCl; 32 mM sucrose; 5 mM 4-(2-hydroxyethyl)-1-piperazineethanesulfonic acid; and 12 mM ammonium acetate.

In another embodiment, the molecule to be delivered has an average molecular weight of up to 15,000 Da, and the method includes introducing 6.6 µM molecules to be delivered to a composition including an aqueous solution having an osmotic concentration of 171 mOsm/L at room temperature and a pH of about 7.4; and includes 20% (v/v) of methanol; 12 mM KCl; 32 mM sucrose; 5 mM 4-(2-hydroxyethyl)-1-piperazineethanesulfonic acid; and 12 mM ammonium acetate.

When the molecule to be delivered has an average molecular weight of up to 1,000 Da, the method can include introducing 150 µM molecules to be delivered to a composition including an aqueous solution having an osmotic concentration of 171 mOsm/L at room temperature and a pH of about 7.4; and includes 25% (v/v) of ethanol; 12 mM KCl; 32 mM sucrose; 5 mM 4-(2-hydroxyethyl)-1-piperazineethanesulfonic acid; and 12 mM ammonium acetate.

In another embodiment, the method includes introducing 150 µM molecules to be delivered when the molecule to be delivered has an average molecular weight of up to 1,000 Da to a composition including an aqueous solution having an osmotic concentration of 171 mOsm/L at room temperature and a pH of about 7.4; and including 20% (v/v) of methanol; 12 mM KCl; 32 mM sucrose; 5 mM 4-(2-hydroxyethyl)-1-piperazineethanesulfonic acid; and 12 mM ammonium acetate.

When the molecule to be delivered has an average molecular weight of up to 1,000 Da, the method can include introducing 150 µM molecules to be delivered to a composition including an aqueous solution having an osmotic concentration of 171 mOsm/L at room temperature and a pH of about 7.4; and including 2% (v/v) of butanol; 12 mM KCl; 32 mM sucrose; 5 mM 4-(2-hydroxyethyl)-1-piperazineethanesulfonic acid; and 12 mM ammonium acetate.

In an embodiment, the molecule to be delivered has an average molecular weight of up to 1,000 Da and the method includes introducing 150 µM molecules to be delivered to a composition that includes an aqueous solution having an osmotic concentration of 171 mOsm/L at room temperature and a pH of about 7.4; and including 25% (v/v) of ethanol; 34 mM NaCl. 0.7 mM KCl, 2.5 mM $Na_2HPO_4$, and 0.5 mM $KH_2PO_4$.

According to example methods, the molecule to be delivered has an average molecular weight of up to 1,000 Da. In some implementations, the composition includes an alcohol, and may include at least two carbon atoms, (e.g., ethanol). The composition may include 2-45% (v/v) of the alcohol, optionally 20-30% (v/v) of the alcohol (e.g., 25% (v/v) of the alcohol). Still further optionally, the composition includes 2-45% (v/v) of ethanol, 20-30% (v/v) of ethanol, and 25% (v/v) ethanol. Preferably, the composition includes 20-30% (v/v) of ethanol. The composition can be a solution (e.g., an aqueous solution). In some implementations, the composition has an osmotic concentration of 171 mOsm/L, optionally at room temperature. Preferably, the composition has an osmotic concentration of 171 mOsm/L at room temperature. In some implementations, the composition includes at least one salt selected from NaCl, KCl, $Na_2HPO_4$, and $KH_2PO_4$. The composition can include less than 46 mM, (e.g., between 2-35 mM salt 10-15 mM salt, ore 12 mM salt). Preferably, the composition includes 12 mM KCl. Optionally, the composition has a pH of about 7.4. In some implementations, the composition includes a sugar, optionally a disaccharide (e.g., sucrose). The composition can include less than 121 mM sugar (e.g., 6-91 mM sugar, 26-39 mM sugar, or 32 mM sugar). Further preferably, the composition may include 32 mM sucrose. In some implementations, the composition can include a buffering agent selected from a weak acid and a weak base. Optionally, the buffering agent is 4-(2-hydroxyethyl)-1-piperazineethanesulfonic acid. Optionally, the composition includes less than 19 mM buffering agent, e.g., 1-14 mM buffering agent, 4-6 mM buffering agent, or 5 mM buffering agent. Further preferably, the composition can include 5 mM 4-(2-hydroxyethyl)-1-piperazineethanesulfonic acid. According to example methods, the composition includes less than 46 mM ammonium acetate, e.g., 2-35 mM ammonium acetate, 10-15 mM ammonium acetate, or 12 mM ammonium acetate. Preferably, the composition includes 150.0 µM molecules to be delivered.

In some implementations, the molecule to be delivered has an average molecular weight of up to 1,000 Da. In some examples, the composition includes an aqueous solution having an osmotic concentration of 171 mOsm/L at room temperature and a pH of about 7.4; and includes 25% (v/v) of ethanol; 12 mM KCl; 32 mM sucrose; 5 mM 4-(2-hydroxyethyl)-1-piperazineethanesulfonic acid; 12 mM ammonium acetate; and 150.0 µM molecules to be delivered.

According to example methods, the molecule to be delivered has an average molecular weight of up to 1,000 Da. In some implementations, the composition can include an alcohol including at least one carbon atoms, (e.g., methanol). Preferably, the composition includes ethanol. The composition can include 2-45% (v/v) of the alcohol, 20-30%

(v/v) of the alcohol, or 25% (v/v) of the alcohol. In some implementations, the composition includes 2-45% (v/v) of methanol, 20-30% (v/v) of methanol, or optionally 20% (v/v) methanol. Preferably, the composition includes 20-30% (v/v) of methanol. In some implementations, the composition is a solution (e.g., an aqueous solution). Optionally or additionally, the composition has an osmotic concentration of 171 mOsm/L, optionally at room temperature. Preferably, the composition has an osmotic concentration of 171 mOsm/L at room temperature. In some implementations, the composition includes at least one salt selected from NaCl, KCl, $Na_2HPO_4$, and $KH_2PO_4$. The composition can include less than 46 mM, 2-35 mM salt, 10-15 mM salt, or 12 mM salt (e.g., 12 mM KCl). The composition can have a pH of about 7.4. In some implementations, the composition includes a sugar, a disaccharide, or sucrose. The composition can include less than 121 mM sugar, 6-91 mM sugar, 26-39 mM sugar, or 32 mM sugar (e.g., 32 mM sucrose). In some implementations, the composition includes a buffering agent selected from a weak acid and a weak base. Optionally, the buffering agent is 4-(2-hydroxyethyl)-1-piperazineethanesulfonic acid. The composition can include less than 19 mM buffering agent, 1-14 mM buffering agent, 4-6 mM buffering agent, and 5 mM buffering agent. Further preferably, the composition includes 5 mM 4-(2-hydroxyethyl)-1-piperazineethanesulfonic acid. In some implementations, the composition includes less than 46 mM ammonium acetate, 2-35 mM ammonium acetate, 10-15 mM ammonium acetate, or 12 mM ammonium acetate. Preferably, the composition includes 150.0 µM molecules to be delivered.

The molecule to be delivered can have an average molecular weight of up to 1,000 Da. In some implementations, the composition includes an aqueous solution having an osmotic concentration of 171 mOsm/L at room temperature and a pH of about 7.4; and includes 20% (v/v) of methanol; 12 mM KCl; 32 mM sucrose; 5 mM 4-(2-hydroxyethyl)-1-piperazineethanesulfonic acid; 12 mM ammonium acetate; and 150.0 µM molecules to be delivered.

According to example methods, the molecule to be delivered has an average molecular weight of up to 1,000 Da. The composition includes an alcohol including at least four carbon atoms (e.g., butanol). Still further, the composition includes 2-8% (v/v) of the alcohol, or 2, 4, or 8% (v/v) of the alcohol (e.g. preferably, the composition includes 2% (v/v) of butanol). In some implementations, the composition is a solution (e.g., an aqueous solution). In some implementations, the composition has an osmotic concentration of 171 mOsm/L, optionally at room temperature. Preferably, the composition has an osmotic concentration of 171 mOsm/L at room temperature. In some implementations, the composition includes at least one salt selected from NaCl, KCl, Na2HPO4, and KH2PO4. The composition can include less than 46 mM, e.g., 2-35 mM salt, 10-15 mM salt, or 12 mM salt. Preferably, the composition includes 12 mM KCl. The composition can have a pH of about 7.4. In some implementations, the composition includes a sugar, optionally a disaccharide, optionally sucrose. Optionally, the composition includes less than 121 mM sugar, 6-91 mM sugar, 26-39 mM sugar, or 32 mM sugar (e.g., 32 mM sucrose). In some implementations, the composition includes a buffering agent selected from a weak acid and a weak base. The buffering agent may be 4-(2-hydroxyethyl)-1-piperazineethanesulfonic acid. The composition can include less than 19 mM buffering agent, 1-14 mM buffering agent, 4-6 mM, and 5 mM buffering agent. Further preferably, the composition includes 5 mM 4-(2-hydroxyethyl)-1-piperazineethanesulfonic acid. In some implementations, the composition includes less than 46 mM ammonium acetate, 2-35 mM ammonium acetate, 10-15 mM ammonium acetate, or 12 mM ammonium acetate. Preferably, the composition includes 150.0 µM molecules to be delivered.

The molecule to be delivered can have an average molecular weight of up to 1,000 Da. In some implementations, the composition includes an aqueous solution having an osmotic concentration of 171 mOsm/L at room temperature and a pH of about 7.4; and includes 2% (v/v) of butanol; 12 mM KCl; 32 mM sucrose; 5 mM 4-(2-hydroxyethyl)-1-piperazineethanesulfonic acid; 12 mM ammonium acetate; and 150.0 µM molecules to be delivered.

According to example methods, the molecule to be delivered has an average molecular weight of up to 1,000 Da. The composition may include an alcohol including at least two carbon atoms (e.g., ethanol). In some implementations, the composition includes 2-45% (v/v) of the alcohol, (e.g., 20-30% (v/v) or 25% (v/v) of the alcohol). Further, the composition can include 2-45% (v/v) of ethanol (e.g., 20-30% (v/v), or 25% (v/v) ethanol. In some implementations, the composition is a solution (e.g. an aqueous solution) According to example methods, the composition may have an osmotic concentration of 171 mOsm/L, (e.g., at room temperature). According to example methods, the composition includes at least one salt selected from NaCl, KCl, $Na_2HPO_4$, and $KH_2PO_4$. The composition can include 34 mM NaCl or 0.7 mM KCl. The composition can include 2.5 mM $Na_2HPO_4$. The composition includes 0.5 mM $KH_2PO_4$. Preferably, the composition includes at least one of 34 mM NaCl. 0.7 mM KCl, 2.5 mM $Na_2HPO_4$, and 0.5 mM $KH_2PO_4$. Preferably, the composition includes 34 mM NaCl. 0.7 mM KCl, 2.5 mM $Na_2HPO_4$, and 0.5 mM $KH_2PO_4$. Preferably, the composition includes 150.0 µM molecules to be delivered.

In preferred embodiments, the method includes the steps of introducing the molecule with a composition to form a matrix; atomizing the matrix; and contacting the matrix with a plasma membrane by delivering 1 µL of matrix in the form of an aerosol to an area of 0.065-0.085 $cm^2$.

The method can include contacting the matrix with a plasma membrane includes delivering 1 µL of matrix to an area of 0.065-0.085 $cm^2$, optionally to an area of 0.065-0.085 $cm^2$ of cells. In certain embodiments, contacting the matrix with a plasma membrane includes delivering 10-100 µL, of matrix, optionally delivering 20 µL of matrix. In a preferable embodiment, contacting the matrix with a plasma membrane includes delivering the matrix in the form of an aerosol, wherein the method further includes the step of atomizing the matrix prior to contacting the matrix with a plasma membrane. The atomizing step can be achieved using an atomizer as described herein. The method preferably includes atomizing the matrix to provide a colloid suspension of particles having a diameter of 30-100 µm prior to contacting the matrix with a plasma membrane.

Figure 1:
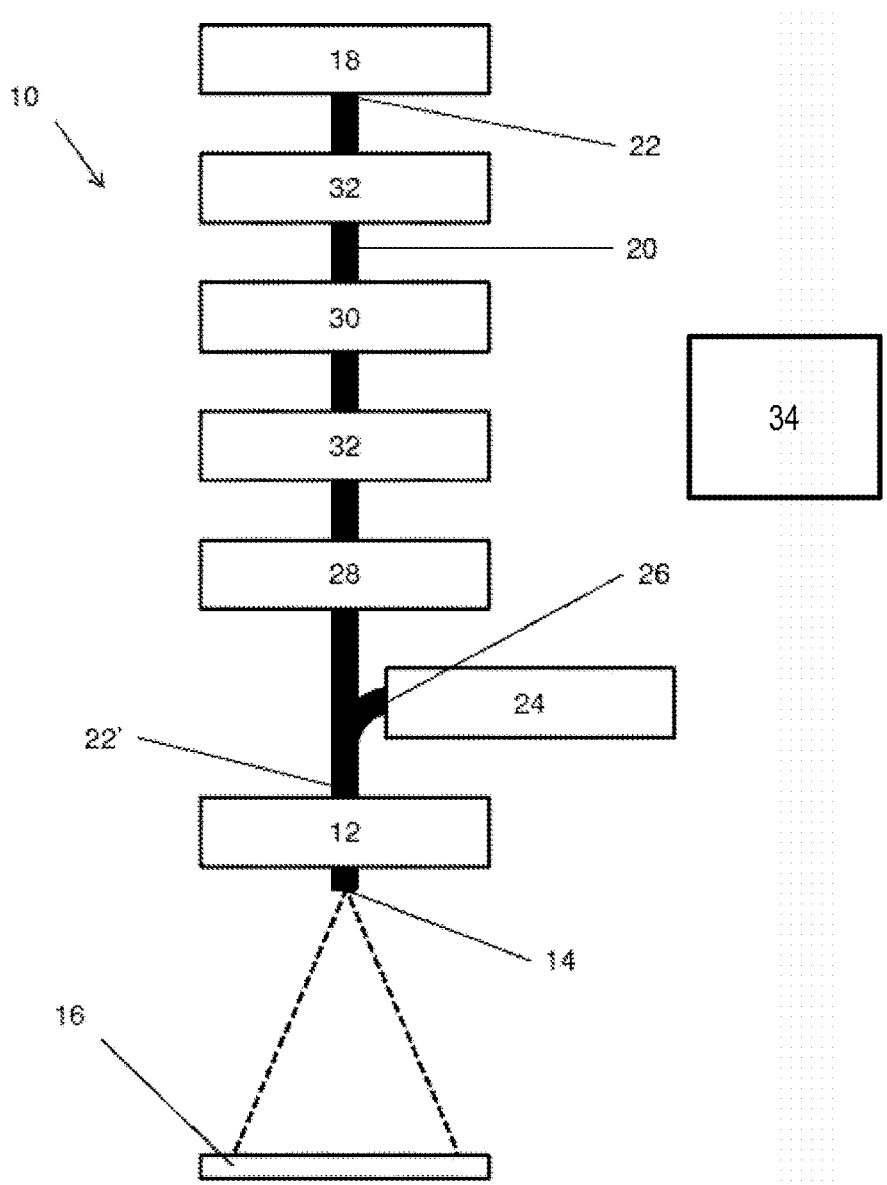
FIG. 1 is a schematic diagram of an apparatus for implementing a method according to the present subject matter.
Figure 2:
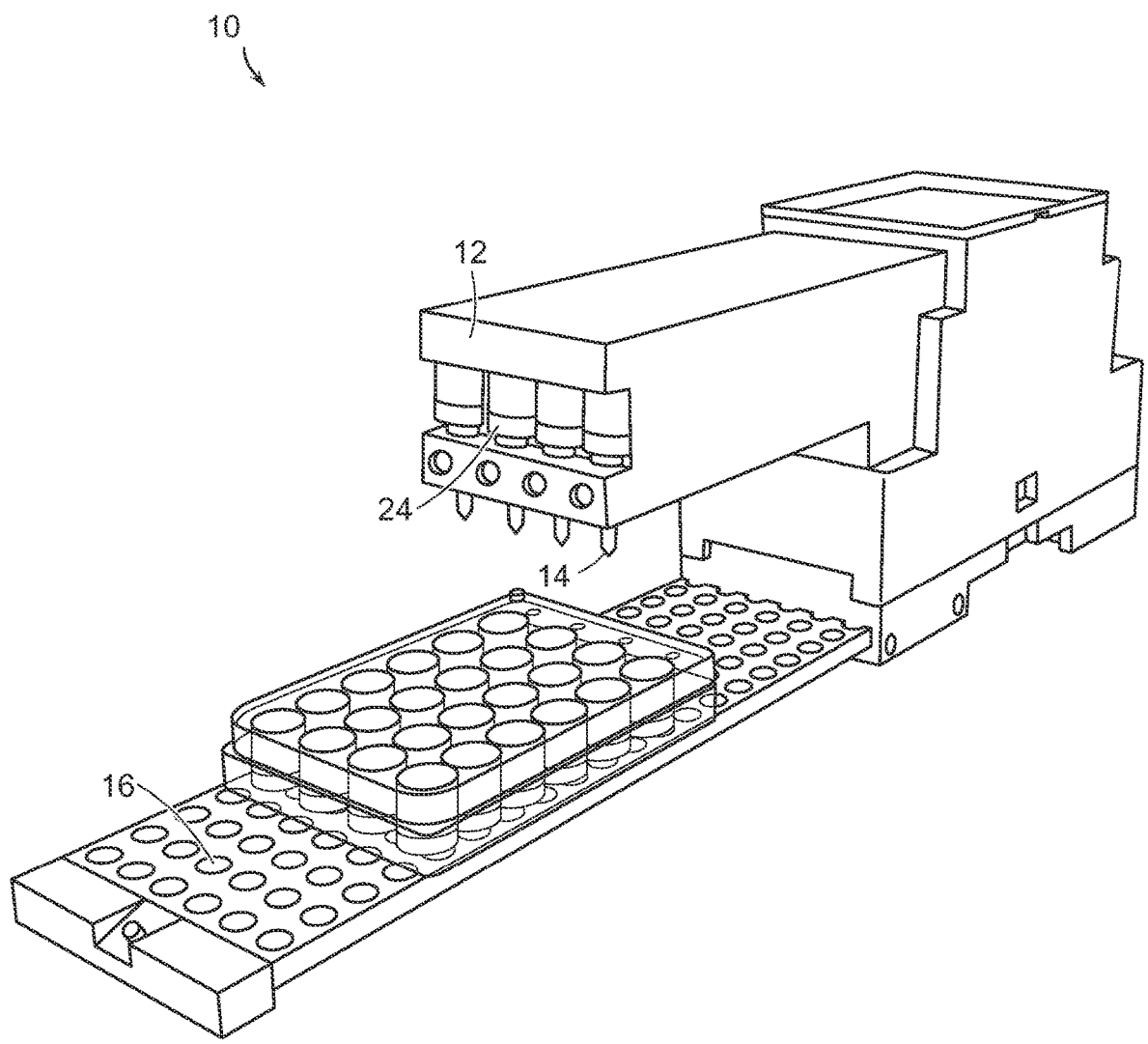
FIG. 2 is a perspective view of an apparatus for implementing a method according to the present subject matter.
Figure 4:
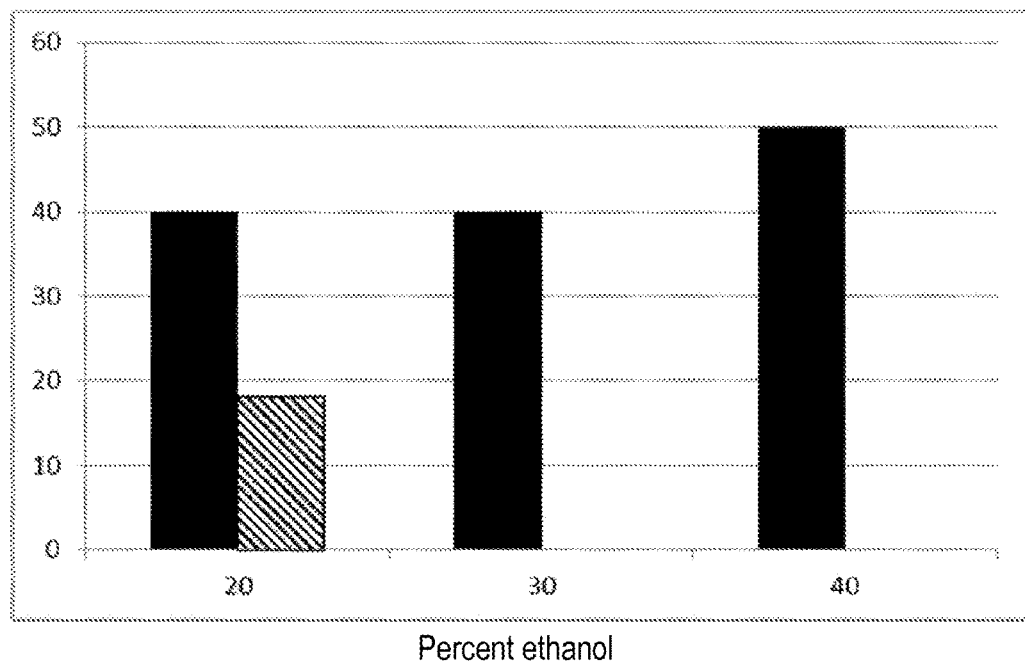
FIG. 4 is a graph illustrating the effect of delivering a molecule having an average molecular weight of up to 15,000 Da across a plasma membrane according to the present subject matter.
Figure 5:
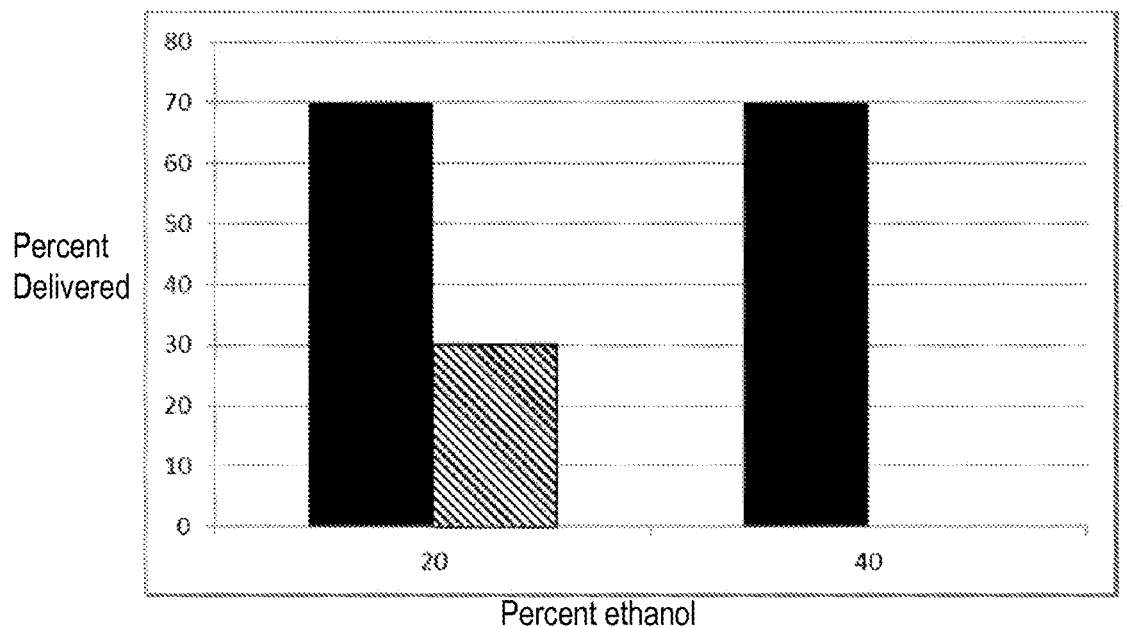
FIG. 5 is a graph illustrating the effect of delivering a molecule having an average molecular weight of up to 1,000 Da across a plasma membrane according to the present subject matter.
Figure 6A:
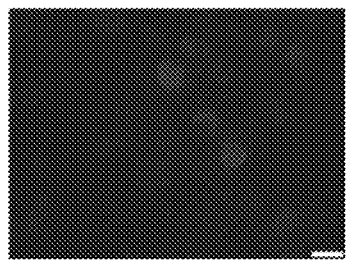
FIG. 6A is a photomicrograph illustrating delivery of a molecule having an average molecular weight of 668 Da.
Figure 6B:
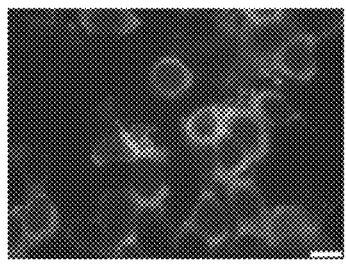
FIG. 6B is a photomicrograph illustrating delivery of a molecule having an average molecular weight of 40,000 Da.
Figure 6C:
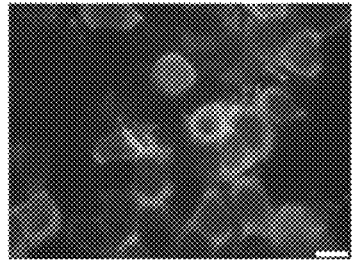
FIG. 6C is a photomicrograph illustrating an overlay of FIGS. 6A and 6B; illustrating the delivery of a molecule having an average molecular weight of 668 Da (FIG. 6A) and 40,000 Da (FIG. 6B).

In the method of the subject matter, the atomizing step includes providing a generally (circular) conical spray zone, as is schematically illustrated in FIG. 1. In preferred embodiments, the atomizing step provides a generally conical spray zone wherein the longitudinal length of the spray zone is greater than the diameter of the circular base of the sprayzone. In particularly preferred embodiments, the atomizing step includes providing a generally conical spray zone wherein the longitudinal length of the spray zone is approximately double the diameter of the circular base of the sprayzone. The circular base of the sprayzone generally equates to the circular base of the area of cells to which molecules are to be delivered. Accordingly, in a certain embodiment, the atomizing step includes providing a generally conical spray zone wherein the longitudinal length of the spray zone is less than or equal to 31 mm and the diameter of the circular base of the area of cells to which molecules are to be delivered is 15.5 mm. The contacting step is preferably conducted at a center point of the area to which the matrix is to be delivered, for example, wherein the longitudinal axis of the spray zone is coaxial with the longitudinal axis or center point of the circular base of the area of cells to which molecules are to be delivered.

The method can include the further step of exposing the cells to which the matrix is to be delivered prior to contacting the matrix with a plasma membrane. In certain embodiments, the exposing step includes removing a substantial amount of the liquid surrounding the cells, for example by aspiration. In additionally preferred embodiments, the method includes the steps of introducing the molecule with a composition to form a matrix; atomizing the matrix; exposing the cells to which the matrix is to be delivered; and contacting the matrix with a plasma membrane by delivering 1 μL of matrix in the form of an aerosol to an area of 0.065-0.085 cm$^2$.

The method can further include incubating the exposed cells, optionally with a buffer solution, such as phosphate buffered saline. Accordingly, an embodiment of the present subject matter defines a method including the steps of introducing the molecule with a composition to form a matrix; atomizing the matrix; removing the supernatant from the cells to which the matrix is to be delivered; washing the cells; and contacting the matrix with a plasma membrane by delivering 1 μL of matrix in the form of an aerosol to an area of 0.065-0.085 cm$^2$.

The method can include the further step of incubating the cells at room temperature for 0.1 seconds-2 minutes, optionally 2 minutes.

It has advantageously been found that the method can include the additional step of contacting the cells with a second composition including 68 mM NaCl, 1.4 mM KCl, 5 mM Na$_2$HPO$_4$, and 0.9 mM KH$_2$PO$_4$. The second composition is a solution, optionally an aqueous solution having a pH of 7.4. In a preferred embodiment, the additional contacting step includes delivering 1 μL of the second composition to an area of 0.0052-0.0068 cm$^2$ for a period of 30 seconds at room temperature.

Following the additional contacting step, the method can further include the step of exposing the cells to which the matrix is to be delivered, for example, by removing a substantial amount of the liquid surrounding the cells by aspiration.

The method further includes culturing the cells after the exposing step, for example, by introducing suitable culture medium to the cells and incubating the cells in a humidified atmosphere with 5% CO2 at 37° C.

Accordingly, in a preferred embodiment, the method includes the additional steps of contacting the cells with a second composition including 68 mM NaCl, 1.4 mM KCl, 5 mM Na$_2$HPO$_4$, and 0.9 mM KH$_2$PO$_4$; exposing the cells to which the matrix is to be delivered; and culturing the cells after the exposing step.

The present subject matter therefore also relates to a second aspect of the present subject matter, there is provided a second composition including 68 mM NaCl, 1.4 mM KCl, 5 mM Na$_2$HPO$_4$, and 0.9 mM KH$_2$PO$_4$, which composition can be an aqueous solution.

The present subject matter also relates to a method for delivering molecules of more than one molecular weight across a plasma membrane; the method including the steps of introducing the molecules of more than one molecular weight to a composition to form a matrix; and contacting the matrix with a plasma membrane.

Example Device for Delivery

The current subject matter further relates to delivering colloidal suspension particles across plasma membranes, for example, by controlling colloidal droplet size. In particular, it has been discovered that intracellular delivery of materials can be achieved when a volume of an aqueous solution is contacted to a population of cells. The volume of aqueous solution that contacts the population can be controlled, for example, by creating a controlled spray of the aqueous solution. A colloidal suspension of the materials can be applied to cell membranes using colloidal suspension droplets of a particular size (or range of sizes). But when colloidal droplets are applied to a cell membrane and colloidal droplet size is too large (and/or overall volume is too great), damage to the cell may occur and cell viability is adversely affected. Conversely, when colloidal droplets are applied to a cell membrane and the colloidal droplet size is too small (and/or overall volume is too small), intracellular delivery of materials is not achieved. Therefore, control of colloidal droplet size (or production of colloidal droplets of or within a range of sizes) can enable intracellular delivery of materials. In some implementations, the payload can be non-colloidal in size, e.g., less than 1 nanometer or greater than 1000 nanometers in diameter.

Referring now to FIG. 1, there is shown a schematic diagram of an apparatus 10 for delivering a molecule across a plasma membrane according to an example implementation of the current subject matter.

Atomizers generate droplets when a sample (e.g., colloidal suspension of delivery material) is input under pressure, for example, using a syringe. The size of droplets produced can correlate to the amount of pressure that is applied such that lower input pressure results in larger droplet sizes. Because input pressure cannot be instantaneously changed, that is, it ramps (e.g., transitions) from zero or low pressure to a higher pressure, and likewise ramps (e.g., transitions) from a higher pressure to a lower pressure, droplets produced have a wide range of sizes. A portion of the colloidal droplets produced can be too large for a given intracellular delivery application. Because a portion of the colloidal droplets produced are too large, cell death may occur notwithstanding the production of appropriately sized colloidal droplets. As described above, cell death is undesirable for some applications. In addition, a portion of the colloidal droplets produced by atomizers can be too small, which leads to inefficient or ineffective intracellular delivery of materials.

The current subject matter enables production of colloidal droplets of a particular size or range of sizes. In addition, the size of colloidal droplets produced can be consistent, that is, production of droplets outside of the desired size or range of sizes is reduced and/or substantially eliminated. Control of colloidal droplet size can be achieved using a high-switching-speed valve with a cavity and/or ensuring that there is sufficient headroom for an input air supply, which enables quick input pressure rise and falls times for an atomizer. The atomizer may be intended for use with a syringe.

What constitutes droplets that are too large and too small may vary based on application (e.g., materials to be delivered and type of target cell). Therefore, intracellular delivery of materials can be achieved by producing colloidal droplets and controlling the size of the colloidal droplets. In some implementations, the colloidal droplets are produced in a manner so that substantially all colloidal droplets applied to target cells have a size within a known/desired range that achieves intracellular delivery. In some implementations, formation of colloidal droplets outside the known/desired range is minimized.

The apparatus 10 includes an atomizer 12 having at least one atomizer emitter 14; and a support 16 for supporting cells.

Contacting the matrix with a plasma membrane can include delivering the matrix in the form of an aerosol, which can be achieved using an atomizer.

The atomizer 12 can be selected from a mechanical atomizer, an ultrasonic atomizer, an electrospray, a nebuliser, and a Venturi tube; and it is within the remit of the skilled person to select the atomizer based on the requirements of delivering a molecule across a plasma membrane. The atomizer 12 can be a commercially available atomizer, such as a commercially available atomizer from LMA Teleflex of NC, USA.

The atomizer 12 is adapted to provide a colloid suspension of particles, each particle having a diameter of 30-100 μm. In certain embodiments, the atomizer 12 is adapted to provide a colloid suspension of particles, wherein each of the particles has a diameter of 50-80 μm. The particles are liquid droplets including molecules to be delivered to the cells.

The atomizer 12 can include a gas reservoir 18. The apparatus 10 can include a pneumatic generator or gas reservoir 18 (also referred to as a pneumatic generator). The gas in the gas reservoir 18 is maintained under pressure. The gas can be selected from air, carbon dioxide, and helium; but it is understood that any suitable gas may be selected and used by the skilled person. The gas reservoir 18 can include a pressure head generator, optionally a fixed pressure head generator to compress the gas in the gas reservoir 18 and so maintain the gas under pressure. Examples of a gas reservoir 18 include bottled gases.

The gas reservoir 18 is in fluid communication with the atomizer emitter 14. The gas reservoir 18 can be in fluid communication with the atomizer emitter 14, such that gas can flow from the gas reservoir 18 to the atomizer emitter 14. In certain embodiments, the gas reservoir 18 includes a gas guide 20, which is in fluid communication with the atomizer emitter 14. Accordingly, the gas guide 20 is adapted to allow the passage of gas therethrough. The gas guide 20 can be a hollow body, such as a hollow body having open ends. In an implementation, the gas guide 20 is a hollow body having first 22 and second 22' open ends, optionally first 22 and second 22' opposing open ends.

In an implementation, the diameter of the first 22 open end is different to the diameter of the second 22' open end. Preferably, the diameter of the first 22 open end is greater than the diameter of the second 22' open end. The first 22 open end can be in fluid communication with the gas reservoir 18. The second 22' open end is preferably in fluid communication with the atomizer emitter 14. When a gas is injected under pressure from the gas reservoir 18 through the gas guide 20, the decreasing section of the gas guide 20 resulting from the diameter of the first 22 open end being greater than the diameter of the second 22' open end, causes the speed of the gas flow to increase, thereby generating a pressure drop at the second 22' open end.

The apparatus 10 can further include a sample reservoir 24. The sample reservoir 24 is in fluid communication with the atomizer 12. In an exemplary implementation, the sample reservoir 24 is in fluid communication with the atomizer emitter 14. In preferred embodiments, the gas reservoir 18 and the sample reservoir 24 are both in fluid communication with the atomizer emitter 14. In such an arrangement, sample can be drawn from the sample reservoir 24 by the pressure drop at the second 22' open end of the gas guide 20. The sample can then be introduced into the gas flow passing through the gas guide 20 from the gas reservoir 18 to the atomizer emitter 14.

In exemplary implementations, the apparatus 10 further includes a sample valve 26 located between the sample reservoir 24 and the gas reservoir 18. The sample valve 26 can be adapted to adjust the sample flow from the sample reservoir 24. The sample valve 26 can be used to allow continuous or semi-continuous sample flow. In an exemplary implementation, the sample valve 26 is adapted to allow semi-continuous sample flow of a defined amount of sample. For example, the sample valve can be adapted to allow semi-continuous sample flow of 0.5-100 μL of sample from the sample reservoir 24. In an exemplary implementation, the sample valve 26 is adapted to allow semi-continuous sample flow of 20 μL of sample from the sample reservoir 24. However, it is understood that sample flow can be selected by a person skilled in the art, whereby the sample valve can be adapted to allow semi-continuous sample flow of 1 μL to an area of 0.065-0.085 $cm^2$.

The atomizer 12 and the support 16 are spaced apart. The support 16 can be oriented toward the atomizer 12 such that the spray plume (spray zone) generated by the atomizer 12 is received at or on the support 16. The support 16 includes a solid support. In some implementations, the support 16 includes a plate including sample wells. In alternative embodiments, the support 16 includes a solid support for receiving and retaining a plate including sample wells. The support 16 or the plate can include sample wells selected from 1, 6, 9, 12, 24, 48, 96, 384, and 1536 wells, for example, the support 16 or the plate can be a 1-, 6-, 9-, 12-, 24-, 48-, 96-, 384-, or 1536-well plate. The support 16 can be, for example a biological membrane, such as a biological tissue, for example a skin tissue or a tracheal tissue; or in some embodiments, a biological organ. The solid support can be formed from an inert material.

In exemplary implementations, the solid support is formed from a plastic material or a metal or metal alloy; although it is understood that any suitable material may be selected and used by the skilled person. The support 16 may be, in some embodiments, a synthetic membrane, such as an aluminum membrane or a plastic membrane.

In exemplary implementations, the support 16 includes a heating element, which can be a resistive element, which can either increase or decrease the temperature on or at the support 16.

The support 16 can be reciprocally mountable to the apparatus 10 to allow the support 16 to be reciprocally movable relative to the apparatus 10. In some implementations, the support 16 is reciprocally movable relative to the atomizer 12 or the atomizer emitter 14. In such an arrangement, the support 16 can be moved relative to the atomizer emitter 14 to achieve the optimal spray plume (spray zone) for delivery of molecules across a plasma membrane. The support 16 can include a support actuator to reciprocally move the support 16 relative to the atomizer 12 or the atomizer emitter 14, optionally the longitudinal axis of the atomizer emitter 14, thereby adjusting the distance between the support 16 and the atomizer emitter 14. The support 16 can additionally include a support actuator to reciprocally move the support 16 transverse to the longitudinal axis of the atomizer emitter 14, thereby adjusting the relative position of the support 16 and the atomizer emitter 14.

In an exemplary implementation, the distance between the atomizer 12 or the atomizer emitter 14 and the support 16 is less than or equal to 31 mm. The spaced apart atomizer 12 and support 16 define a spray zone there between. In an implementation, the longitudinal length of the spray zone is 31 mm.

The longitudinal axis of the spray zone is preferably coaxial with the longitudinal axis of the support 16. Additionally, the longitudinal axis of the atomizer emitter 14 is preferably coaxial with the longitudinal axis of the support 16. In such an arrangement, the longitudinal axis of the atomizer emitter 14, the longitudinal axis of the support 16, and the longitudinal axis of the spray zone are each coaxial, thereby ensuring that the atomizer emitter 14, and the spray zone associated with the atomizer emitter 14, are centered over the support (for example, the circular well of a plate) 16 for delivery.

The apparatus 10 can further include a valve 28 located between the gas reservoir 18 and the atomizer 12. The valve 28 can be an electromagnetically operated valve, such as a solenoid valve. Alternatively, the valve 28 can be a pneumatic valve. The valve 28 is preferably located at the gas guide 20 and can be adapted to adjust the gas flow within the gas guide 20. For example, the vale 28 can be switchable between a closed position for preventing the gas from activating the atomizer 12 and an open position for allowing the gas under pressure to activate the atomizer 12 to produce colloidal droplets. The open position can be partially open so as to control the pressure that is received by the atomizer 12. The valve 28 can be adapted to allow continuous or semi-continuous gas flow. In an example implementation, the valve 28 is adapted to allow semi-continuous gas flow of a defined time interval, for example, semi-continuous gas flow of a one second time interval.

The valve 28 can be adapted to allow continuous or semi-continuous gas flow. In a preferred embodiment, the valve 28 is adapted to allow semi-continuous gas flow of a defined time interval, for example, semi-continuous gas flow of a one second time interval.

To ensure sterility and to remove foreign particles, the apparatus 10 can further include at least one filter 30. In some implementations, each filter 30 has a pore size of less than 10 μm, but the skilled person can readily determine the pore size to be used and selected. Each filter 30 is located at the gas guide 20, and each filter 30 is in fluid communication with the gas guide 20.

The apparatus 10 can include at least one regulator 32, which can be an electrical regulator or a mechanical regulator. Each regulator 32 is located at the gas guide 20 and is in fluid communication with the gas guide 20. Each regulator 32 can be a regulating valve and can be adapted to adjust the pressure within the gas guide 20 to 1.0-2.0 bar. Each regulating valve can also maintain the pressure within the gas guide 20 at 1.0-2.0 bar. In exemplary implementations, each regulating valve maintains the pressure within the gas guide 20 at 1.5 bar. Exemplary implementations of the current subject matter can include two regulators 32. For example, the apparatus 10 can include first 32 and second 32' regulators. The first 32 and second 32' regulators are located at the gas guide 20 and are each in fluid communication with the gas guide 20. In an exemplary implementation, the first regulator 32 is located between the gas reservoir 18 and the filter 30. The first regulator 32 is adapted to adjust the pressure from the gas reservoir 18 within the gas guide 20 to 2.0 bar, and to maintain the pressure within the gas guide 20 at 2.0 bar. The second regulator 32' is located between the filter 30 and the valve 28.

According to some implementations, the atomizer emitter 14 is adapted to provide a conical spray zone. The atomizer emitter 14 can be adapted to provide a 30° conical spray zone.

The apparatus 10 can further include a microprocessor to control any or all parts of the apparatus 10; for example, the microprocessor can be arranged to control any or all of the sample valve 26, the support actuator, the valve 28, and the regulator 32.

In some implementations, the apparatus 10 is arranged to deliver 1 μL of sample to an area of 0.065-0.085 $cm^2$, optionally to deliver 1 μL of matrix to an area of 0.065-0.085 $cm^2$ of cells. The sample is can be delivered in the form of an aerosol by atomizing the sample prior to contacting the sample with a plasma membrane. The atomizer 12 can form droplets of the sample, each droplet having a cross sectional dimension of 30-100 μm, or more preferably, 50-80 μm. Optionally or additionally, the atomizer forms droplets of the sample, each droplet having a cross sectional dimension of less than 10 μm. The apparatus 10 is preferably arranged such that delivery is conducted at a center point of the area to which the sample is to be delivered.

Materials and Methods.

All inorganic materials used were of 'Analar' grade, unless otherwise stated. All materials were of tissue culture grade and purchased from Sigma, unless otherwise stated.

100 ml of a first solution (Solution A) was prepared to a final concentration of 43 mM sucrose, 16 mM potassium chloride, 16 mM ammonium acetate and 7 mM Hepes in molecular grade water, adjusted to pH 7.4 by adding 1.15 ml 1 M NaOH and filter sterilised using a filter with pore size 0.2 μm, before combining with ethanol in a ratio of 3:1.

100 ml of a second solution (Solution B) was prepared to a final concentration of 68 mM NaCl, 1.4 mM KCl, 5 mM $Na_2HPO_4$, and 0.9 mM $KH_2PO_4$ in molecular grade water. The pH of the resultant solution was adjusted to pH 7.4 by adding 1.13 ml 1 M NaOH and was sterilised by autoclaving.

The molecules to be delivered to the cells included propidium iodide (668 Da), miRNA (15,000 Da) (Thermo Scientific), siRNA molecules (15,000 Da) (Life Technologies), dextran (3000-2,000,000 Da) (Life Technologies).

Propidium iodide solution (1.0 mg/ml in water) was obtained from Sigma Aldrich under Cat. No: P4864; non-targeting miRNA labelled with Dy547 was obtained from ThermoScientific under Cat. No: CP-004500-01-05; fluorescein-labelled double stranded RNA oligomer (siRNA) was obtained from Biosciences under Cat. No: 13750062; and fluorescein-labelled dextrans were obtained from Life Technologies Dextran 40,000 under Cat. No. D1845; Dextran 70,000 under Cat. No. D1823; Dextran 2,000,000 under Cat. No. D7137; and Dextran 500,000 under Cat. No. D7139.

Molecules to be delivered to the cells were added to Solution A to form a matrix. The amount of molecules to be delivered was independent of the amount of molecules added to Solution A. In the present experiments, the amount of molecules added to Solution A was such that the matrix included 150 μM propidium iodide (668 Da), 3.3 or 6.6 μM miRNA (15,000 Da), and 3.3 or 6.6 μM siRNA molecules (15,000 Da).

Cells and Cell Culture. T24 human bladder carcinoma, U373 glioblastoma, SKBR3 human hypertriploid, HeLa human epithelial adenocarcinoma, CHO-K1 Chinese hamster ovary, COS-7 SV40 transformed kidney fibroblast, C2C12 mouse myoblast; A549 adenocarcinomic human alveolar epithelial and Beas2B human bronchial epithelial cell lines were obtained from the American Type Culture Collection (ATCC). HEK-n Human Epidermal Keratinocytes-neonatal and HDF Normal Human Dermal Fibroblasts cell lines were obtained from Caltag MedSystems.

All cell lines were grown in a humidified atmosphere with 5% $CO_2$ at 37° C. Routine aseptic sub-culture of cells was carried out every 72 h or upon reaching 75-90% confluence, whichever occurred first.

For experiments, cells were seeded at a density of approximately $4 \times 10^3$ cells/well in 24-well plates and allowed to adhere for twenty four hours such that cells reached 75-90% confluence on the day of delivery.

Delivery of Molecules. An intranasal mucosal atomization device commercially available from LMA Teleflex of NC, USA under catalogue number MAD300 and including an atomizer emitter was set up as follows: the atomizer emitter was positioned 31 mm from the base of the 24-well plate and above the center point of each circular well of the plate. The atomizer emitter was adjusted to allow a pressure of 1.5 bar. A timer was utilized to dispense spray from the atomizer emitter for a period of 1 second. The atomizer emitter was primed by rinsing three times with Solution A containing molecules to be delivered.

Each well of the plate was treated as follows: cell culture medium was removed from the well using a micropipette. Optionally, the well was rinsed twice with 250 μL phosphate buffered saline (PBS) using a micropipette. 20 μL of Solution A containing molecules to be delivered was delivered to the cells using the atomizer. The plate was incubated at room temperature for a period of 30 seconds to 2 minutes depending on the size of the molecule to be delivered, following which 250 μL of Solution B was added to the well using a micropipette. The plate was then incubated at room temperature for 30 seconds, at which time Solution B was removed from the well using a micropipette. 500 μL of culture medium was added to the well using a micropipette. The cells were then returned to a humidified atmosphere with 5% $CO^2$ at 37° C.

Fluorescence Microscopy. Fluorescein isothiocyanate (FITC)—and DyLight Phosphoramidite (DY547)-labelled molecules were used in accordance with the manufacturer's instructions. Labelled molecules to be delivered to the cells were added to Solution A and delivered to cells as described above herein. Following delivery, the plate was placed onto the stage of a fluorescent microscope (Olympus CKX 41) and the cells were viewed using filters to visualize fluorescence. Photomicrographs were acquired.

Flow Cytometry. Following delivery, cells were removed from each well of the plate using 200 μL trypsin. 200 μL culture medium was used to inactivate the trypsin. Cells were pelleted by centrifugation for 5 minutes at 259 relative centrifugal force (RCF) and the pellet was re-suspended in 200 μL PBS using a micropipette tip. The cell suspension was loaded into a flow cytometer [Accuri Flow Cytometyer, BD Biosciences] and the fluorescence was analyzed according to manufacturer's instruction.

Cell Viability. Following delivery, cell viability was assessed using the CellTiter 96® AQueous One Solution Cell Proliferation Assay (MTS) (Promega) according to the manufacturer's instructions. In short, medium was removed from the well by aspiration and replaced with 200 μL fresh medium to which 40 μL MTS reagent was added. The plate was incubated at 37 degrees C. for 1 hour protected from light. 100 μL of solution was removed from the well and placed into a 96-well plate and absorbance was read at 450 nm using a GloMax 96 Microplate luminometer [Promega].

Co-localization visualization. Fluorescein isothiocyanate (FITC)—and DyLight Phosphoramidite (DY547)-labelled molecules were used in accordance with the manufacturer's instructions. Following delivery, the plate was placed onto the stage of a fluorescent microscope [Olympus CKX 41] and the cells were viewed using filters to visualize fluorescence. Photomicrographs were acquired.

The current subject matter further relates to delivering colloidal suspension particles across plasma membranes, for example, by controlling colloidal droplet size. In particular, it has been discovered that intracellular delivery of materials can be achieved when a colloidal suspension of the materials is applied to cell membranes using colloidal suspension droplets of a particular size (or range of sizes). But when colloidal droplets are applied to a cell membrane and colloidal droplet size is too large, damage to the cell may occur and cell viability is adversely affected. Conversely, when colloidal droplets are applied to a cell membrane and the colloidal droplet size is too small, intracellular delivery of materials is not achieved. Therefore, control of colloidal droplet size (or production of colloidal droplets of or within a range of sizes) can enable intracellular delivery of materials.

Atomizers generate droplets when a sample (e.g., colloidal suspension of delivery material) is input under pressure, for example, using a syringe. The size of droplets produced can correlate to the amount of pressure that is applied such that lower input pressure results in larger droplet sizes. Because input pressure cannot be instantaneously changed, that is, it ramps (e.g., transitions) from zero or low pressure to a higher pressure, and likewise ramps (e.g., transitions) from a higher pressure to a lower pressure, droplets produced have a wide range of sizes. A portion of the colloidal droplets produced can be too large for a given intracellular delivery application. Because a portion of the colloidal droplets produced are too large, cell death may occur notwithstanding the production of appropriately sized colloidal droplets. As described above, cell death is undesirable for some applications. In addition, a portion of the colloidal droplets produced by atomizers can be too small, which leads to inefficient or ineffective intracellular delivery of materials.

The current subject matter enables production of colloidal droplets of a particular size or range of sizes. In addition, the size of colloidal droplets produced can be consistent, that is, production of droplets outside of the desired size or range of sizes is reduced and/or substantially eliminated. Control of colloidal droplet size can be achieved using a high-switching-speed valve with a cavity and/or ensuring that there is sufficient headroom for an input air supply, which enables quick input pressure rise and falls times for an atomizer. The atomizer may be intended for use with a syringe.

What constitutes droplets that are too large and too small may vary based on application (e.g., materials to be delivered and type of target cell). Therefore, intracellular delivery of materials can be achieved by producing colloidal droplets and controlling the size of the colloidal droplets. In some implementations, the colloidal droplets are produced in a manner so that substantially all colloidal droplets applied to target cells have a size within a known/desired range that achieves intracellular delivery. In some implementations, formation of colloidal droplets outside the known/desired range is minimized.

The apparatus 10 can further include a valve 28 located between the gas reservoir 18 and the atomizer 12. The valve 28 can be an electromagnetically operated valve, such as a solenoid valve. The valve 28 can be a pneumatic valve. The valve 28 can be located at the gas guide 20 and can be adapted to adjust the gas flow within the gas guide 20. For example, the vale 28 can be switchable between a closed position for preventing the gas from activating the atomizer 12 and an open position for allowing the gas under pressure to activate the atomizer 12 to produce colloidal droplets. The open position can be partially open so as to control the pressure that is received by the atomizer 12. The valve 28 can be adapted to allow continuous or semi-continuous gas flow. In an example implementation, the valve 28 is adapted to allow semi-continuous gas flow of a defined time interval, for example, semi-continuous gas flow of a one second time interval.

In some implementations, the switching speed of the valve 28 can be less than 250 milliseconds. The switching speed can be the time required for the valve 28 to transition between the closed position and open position (and/or vice versa). In some implementations, the valve 28 has a switching speed that is less than 200 milliseconds. In some implementations, the valve 28 has a switching speed between 50 and 200 milliseconds. Other implementations are possible.

The valve 28 can include a cavity.

In some implementations, the atomizer 12 can produce colloidal droplets having a diameter between 30 and 100 micrometres. In some implementations, the atomizer 12 can produce colloidal droplets having a diameter between 30 and 50 micrometres. In some implementations, because of the characteristics of apparatus 10 (e.g., such as a fast valve 26 switching time), the pressure that inputs to the atomizer 12 results in greater than 80 percent of the colloidal droplets produced by the atomizer 12 as having a diameter between 30 and 100 micrometres (as measured over a 1 second period in which the valve transitions at least once from the closed position to the open position or from the open position to the closed position). In some implementations, the pressure that inputs to the atomizer 12 results in greater than 99 percent of the colloidal droplets produced by the atomizer 12 as having a diameter between 30 and 100 micrometres (as measured over a 1 second period in which the valve transitions at least once from the closed position to the open position or from the open position to the closed position).

In operation, the current subject matter can enable intracellular delivery of molecules. FIG. 3 is a process flow diagram illustrating a process 800 of producing colloidal droplets for delivering a sample to the cytoplasm of one or more target cells. At 810, a gas can be generated by a pneumatic generator or gas reservoir 18. The gas can be under pressure. At 820, a valve can be switched from a closed position for preventing the gas under pressure from activating an atomizer 12 and an open position for allowing the gas under pressure to activate the atomizer to produce colloidal droplets. The valve 28 can be between the pneumatic generator or gas reservoir 8 and the atomizer 12. A sample can be provided from a sample reservoir for the atomizer to produce colloidal droplets. Other implementations are possible.

Additional example implementations follow.

Example 1: Development of Technique

Delivery of molecules into living cells is highly desirable for a wide range of applications. Generally, the types of molecules involved can be categorised according to the mass of the molecule: (i) small chemical molecules generally have an average molecular weight of: <1,000 Da; (ii) peptides generally have an average molecular weight of: ~5,000 Da; (iii) siRNA molecules generally have an average molecular weight of: ~15,000 Da; (iv) antibodies generally have an average molecular weight of: ~150,000 Da; and (v) nucleic acids, such as DNA, generally have an average molecular weight of: ~5,000,000 Da.

A variety of approaches are taken to deliver molecules across a plasma membrane and into a cell, each approach depending on the size and chemistry of molecule to be delivered. Organic solvents, such as DMSO, have been used to deliver small chemical molecules. While the molecular basis of the action of DMSO on a plasma membrane is still obscure, DMSO is known to exhibit three distinct modes of action, each over a different concentration range. At low concentrations, DMSO induces plasma membrane thinning and increases fluidity of the hydrophobic core of the plasma membrane. At higher concentrations, DMSO induces transient water pores in the plasma membrane. At still higher concentrations, individual lipid molecules are irreversibly desorbed from the plasma membrane followed by a detrimental disintegration of the bilayer structure of the plasma membrane.

Introduction of larger, biological molecules such as oligopeptides, polypeptides or proteins, and nucleic acids (such as plasmid DNA, oligonucleotides, and siRNA) is referred to as 'transfection'. Use of traditional delivery compositions, such as DMSO, are not efficient for delivery of these larger molecules. siRNA molecules are usually delivered by liposome-mediated transfection (lipofection). Plasmid DNA is usually delivered using biological (viruses), chemical (lipid-based or chemical polymers), or physical (electroporation, magnetofection, injection) methods. However, these methods are not well-suited for proteins and peptides, and furthermore, many cell types, particularly primary cells and stem cells, remain 'hard to transfect' even with nucleic acid molecules where high toxicity levels are often a problem.

A wide range of methods are also used to chemically 'permeabilise' cells and tissues. However, the vast majority of these methods are not aimed at 'reversible permeabilisation' and delivery into a living cell. Instead, the methods are usually aimed at 'irreversible permeabilisation' to deliver a 'label' that will attach to a molecule or structure within a cell or tissue for purposes such as visualisation or quantification (for example, immunofluorescence). In these situations, the cells and tissues are non-viable following permeabilisation. Chemicals typically used in these methods include alcohols (which dissolve lipids in a plasma membrane), detergents (which create pores in a plasma membrane) and enzymes (which digest proteins and create pores in a plasma membrane).

A small number of studies have reported successful reversible permeabilisation using detergents. Detergents (e.g., surfactants) are widely used in biology for protein extraction from cell membranes and as membrane permeabilizing agents. Triton X-100 (TX100) is one of the most widely used non-ionic surfactants for lysing cells or to permeabilize the living cell membrane for transfection. Other exemplary surfactants include polysorbae 20 (e.g., Tween 20), 3-[(3-cholamidopropyl)dimethylammonio]-1-propanesulfonate (CHAPS), 3-[(3-cholamidopropyl)dimethylammonio]-2-hydroxy-1-propanesulfonate (CHAPSO), sodium dodecyl sulfate (SDS), and octyl glucoside. However, cell viability is extremely sensitive within a narrow range of surfactant concentrations and controlling the TX100 concentration for transfection is difficult. Van den Ven et al. report using TX100 to deliver molecules ranging from 1,000 MW to 150,000 MW to cultured cells (van de Ven K., et al., *J. Biomed Opt* 2009:14(2), incorporated herein by reference in its entirety). Medepalli et al. report using saponin in conjunction with a hypotonic buffer (sucrose, KCl, potassium acetate, Hepes) to deliver nanometer sized quantum dots to cultured cells (Medepalli, K., et al., *Nanotechnology* 2013; 24:20, incorporated herein by reference in its entirety). This hypotonic buffer is used to support cell viability by providing ions and pH buffering to the cells whilst also being hypotonic with the intention that water should flow into the permeabilised cells and bring the payload with it (note that water is itself toxic to cells). However, the experiments of the van de Ven and Medepalli reports have been unable to be repeated.

A vector-free delivery method was developed based on reversible permeabilisation that would facilitate delivery of payloads into cells in a manner that would retain cell viability and payload functionality. As other groups have done, the following hypothesis was utilized: firstly, permeabilisation could be induced by chemical modification of the cell membrane; secondly, delivery could be enhanced via osmotic pressure brought about by using a hypotonic delivery solution whereby influx of water into the permeabilised cells facilitated influx of a payload and thirdly, cell survival could be enhanced if the hypotonic delivery solution was also buffered and physiological. Based on initial observations, further hypotheses were developed and refined as described later here. For chemical permeabilisation, the most common permeabilising agents are detergents which interact with certain components in cell membranes to create holes (Hapala, I., *Crit Rev. Biotech.* 1997; 17(2): 105-22). Medepalli et al reported delivery of quantum dots into cultured cells by incubating cells in a specific hypotonic physiological buffered solution termed 'S Buffer' (78 mM sucrose, 30 mM KCl, 30 mM potassium acetate, 12 mM HEPES) for 5 min at 4° C. (Medepalli K. et al., *Nanotechnology* 2013; 24(20)). In some examples, potassium acetate is replaced with ammonium acetate in the "S" buffer. They also stated that delivery could be enhanced by adding saponin to the solution. However, high levels of cell damage and detachment of A549 cells were observed under these conditions and did not observe uptake of labelled siRNA and dextran molecules. Organic solvents such as alcohols can permeabilise cells by dissolving lipid from the cell membrane. A reversible permeabilising protocol using ethanol as the permeabilising agent was made.

Figure 17:
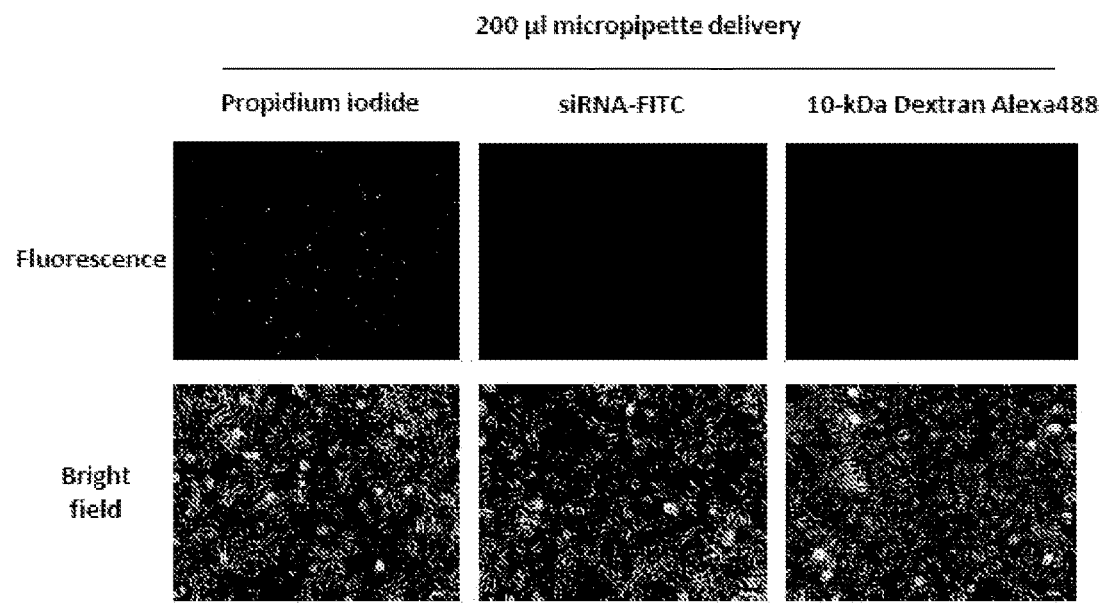
FIG. 17 is a photomicrograph illustrating the micropipette-mediated delivery of payloads in 200 μL of delivery solution to A549 cells in 24-well plates, and viewed by fluorescent microscopy. Propidium iodide (PI) uptake was visible throughout the cell population, but no uptake of siRNA-FITC or 10 kDa Dextran Alexa488 was apparent. All photomicrographs are shown at a 10× magnification.
Figure 19:
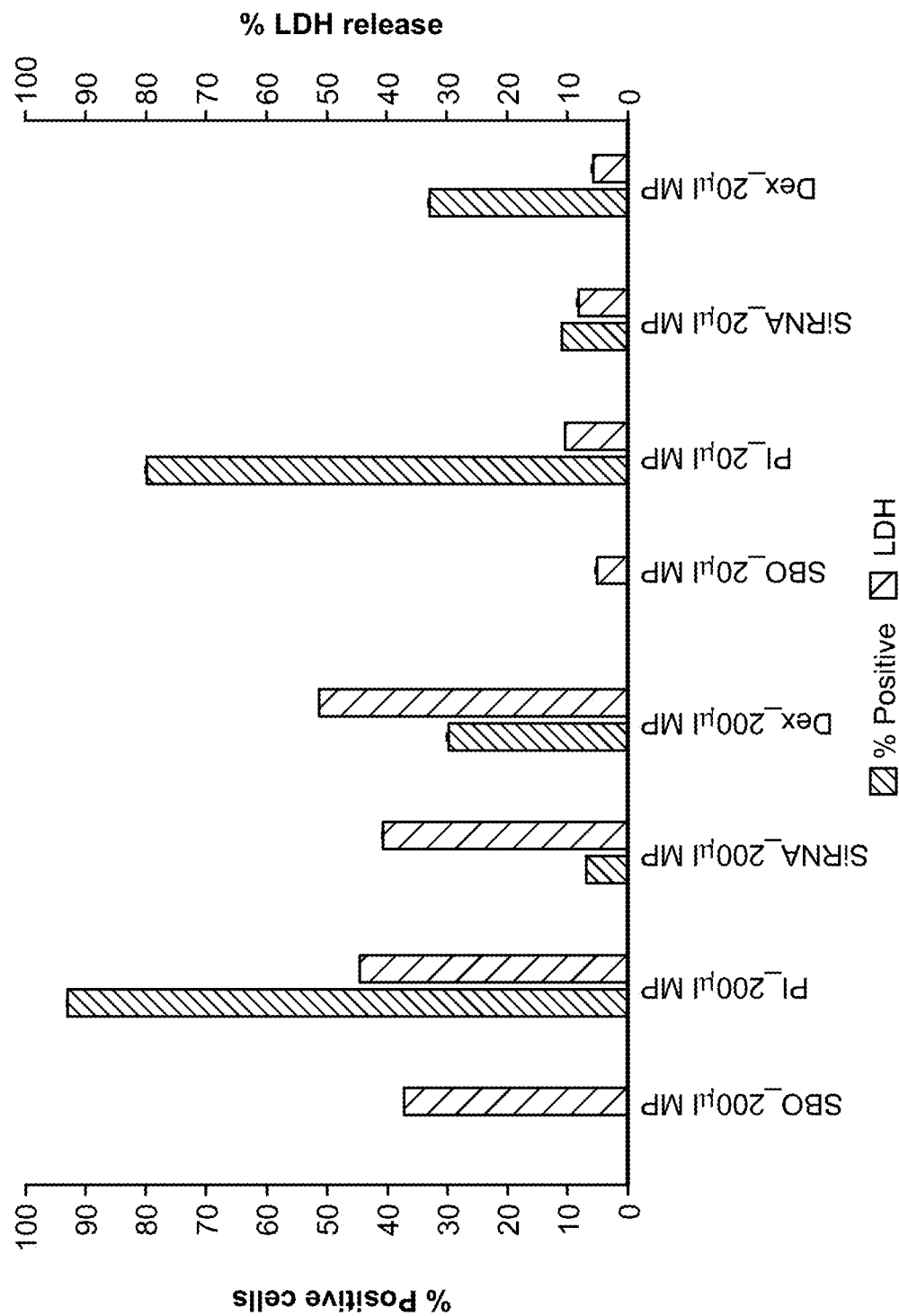
FIG. 19 is a graph illustrating Micropipette-mediated delivery of payloads in either 200 μl or 20 μl delivery solution to A549 cells in 24-well plates. Uptake efficiency was measured by flow cytometry (5% m bar) and toxicity was measured by lactate dehydrogenase (LDH) release compared to lysed cells positive control. When payloads were delivered in 200 μl, uptake was detected by flow cytometry but toxicity levels were high (40-50%). When payloads were delivered in 20 μl, toxicity was reduced but uptake was also reduced and was inconsistent; (n=3). MP=micropipette; PI=propidiumiodide; Dex=10 kDadextran-Alexa488; SBO=spray buffer only.

A range of ethanol concentrations in several diluents including water and PBS as well as various concentrations of S Buffer were examined. Replacing potassium acetate in the S buffer with ammonium acetate gave better delivery efficiencies, because of effects on the cell membrane. A preferred delivery solution composition which gave desirable initial results was 75% $H_2O$, 25% ethanol, 32 mM sucrose, 12 mM KCl, 12 mM ammonium acetate and 5 mM Hepes and was used from this point on unless otherwise stated. However, that this solution induced significant toxicity when pipetted directly onto cells in large volumes, thereby soaking or submerging the cells, FIG. 56A. When 200 µl delivery solution (per well of a 24-well plate) containing PI was pipetted directly onto exposed cells, most cells immediately stained positive for PI (FIG. 17). LDH release measured at 24 hr post-delivery indicated that approximately 50% cells were damaged (FIG. 19). In contrast, no delivery of larger molecules such as 10-kDa dextran-Alexa488 or siRNA-FITC was observed (FIG. 17). The cells were being over-permeabilised to the point of lethal damage where PI could enter and bind to nuclear DNA but osmotic pressure gradients could not be established to deliver the larger payloads.

Figure 18:
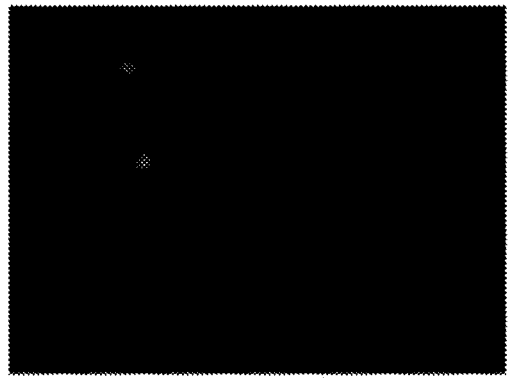
FIG. 18 is a photomicrograph illustrating the micropipette-mediated delivery of payloads in 20 μL, of delivery solution to A549 cells in 24-well plates, and viewed by fluorescent microscopy. Uptake of PI was apparent in some areas of the well but not in others. All photomicrographs are shown at a 10× magnification.
Figure 18:
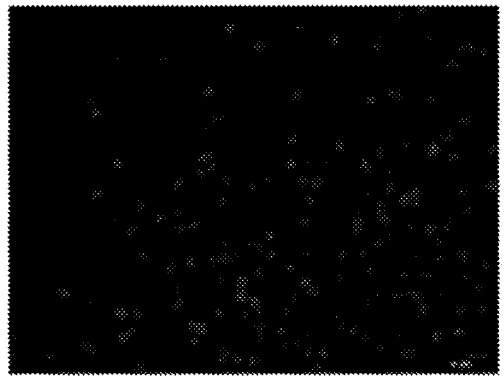
Figure 18:
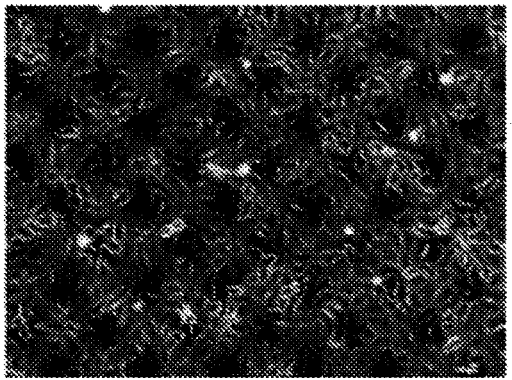
Figure 18:
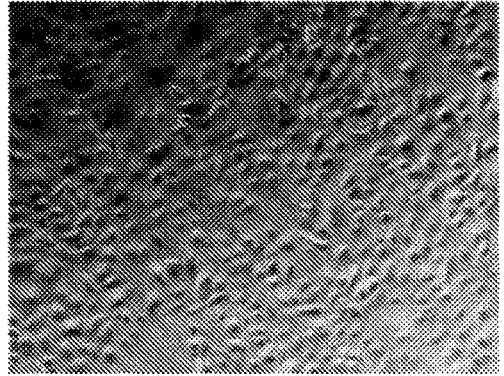

Therefore, to minimize damage, the delivery process can be as rapid as possible with the maximum volume of payload being delivered in the smallest volume and shortest time practicable. Cells were seeded into 24-well plates on Day 0 such that they were 80-90% confluent on Day 1 when delivery was carried out. Supernatant was removed from the target well and 20 µl delivery solution containing PI, 10-kDa dextran-Alexa488 or siRNA-FITC was pipetted into the well. Cells were incubated for 2 min at room temperature (RT) to facilitate uptake. To further facilitate uptake and prevent cell dehydration, 200 µl 0.5×-PBS was then added and cells were incubated for a further 30 sec. This solution was then removed and 400 µl culture medium was added. The cells were then analyzed by fluorescence microscopy. With this method, PI uptake was apparent at the edge of the well but not in the center (FIG. 18). Delivery results were also inconsistent with this method. No delivery of 10-kDa dextran-Alexa488 or siRNA-FITC was observed (FIG. 17 and FIG. 18). LDH levels were reduced however compared with the larger 200 µl volume (FIG. 19). Over-permeabilisation of some cells and under-permeabilisation of others was taking place. Simultaneous delivery of the permeabilising solution to all cells was preferable to 'dropping on' volumes using a micropipette where not all cells were targeted at the same time. Furthermore, the volume reaching a cell should be sufficient to permit influx of water into the cell but insufficient to bring the cell to bursting point. In other words, the volume should be titered to match the absorbance capacity of the cells. A spray-mediated delivery achieved these outcomes, whereby the spray maximized contact of the payload with the cell membrane of the target cells in a very short timeframe and in a uniform manner, resulting in preservation of cell viability and reliable and robust uptake of payload across the cell membrane and into the interior of the cells (FIG. 56B).

Figure 20:
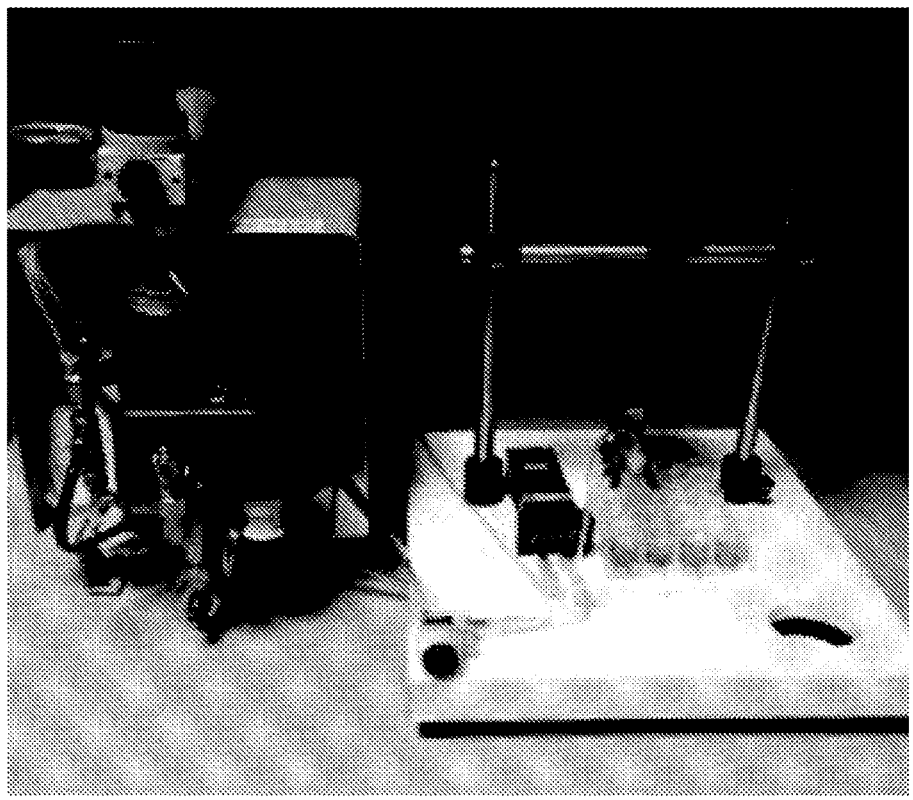
FIG. 20 is an image showing the instrument. An instrument was constructed that would enable spray mediated delivery of the delivery solution to cells. The instrument comprised an air compressor that delivered compressed air to a sprayhead which was held in position on a retort stand. The culture plate was positioned on a stage below the sprayhead.
Figure 21:
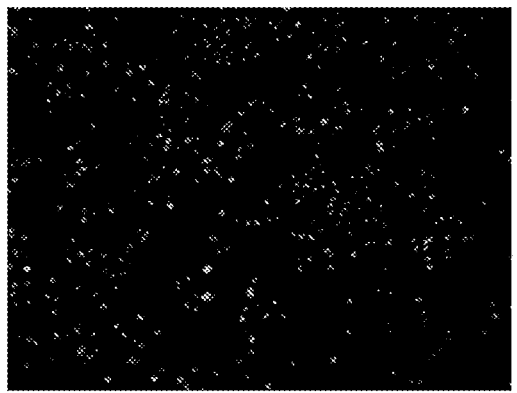
FIG. 21 is a photomicrograph illustrating delivery of 10 kDa dextran-Alexa488 to A549 cells via an example implementation of the present subject matter. 10 kDa dextran-Alexa488 was successfully delivered to A549 cells using the method of the current subject matter. Uptake was evident across the cell monolayer. A 10× magnification is shown in the photomicrograph.
Figure 21:
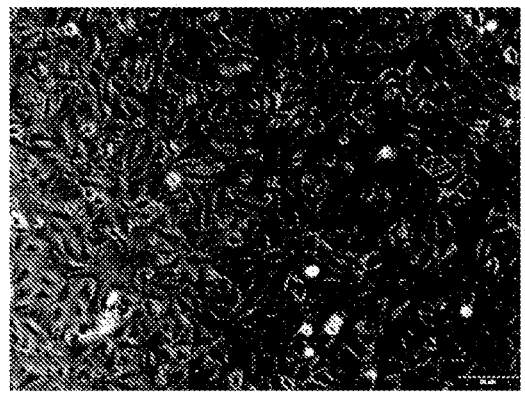
Figure 22:
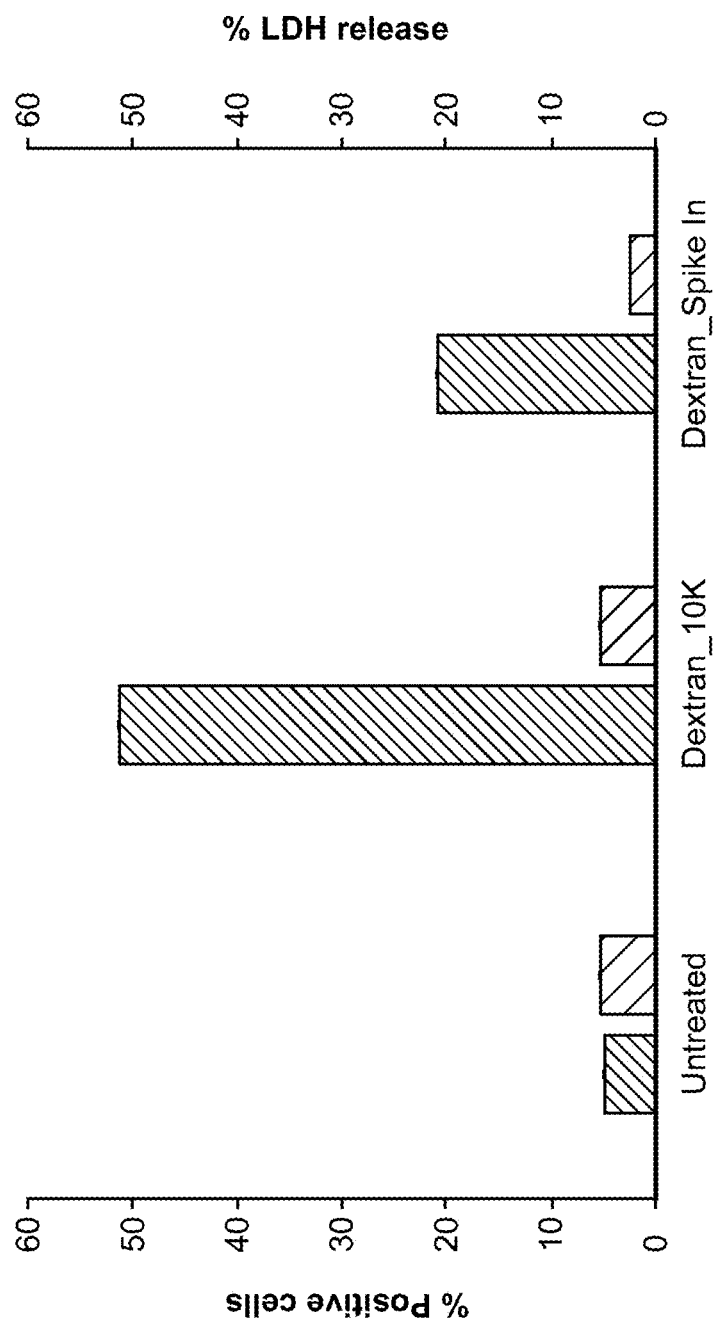
FIG. 22 is a graph showing the efficiency and toxicity of the delivery method of the current subject matter. Efficiency levels of greater than 50% delivery of 10-kDa dextran-Alexa488 were achieved in A549 cells. Toxicity levels were similar to untreated controls. When the delivery solution containing payload was spiked into the culture medium, some positive cells were also detected (n=3).

Instrument. To implement this approach, an instrument was configured including x, y and z (FIG. 20). The instrument was used to deliver 10-kDa dextran to A549 cells. Cells were seeded into 48-well plates in order to match the cell monolayer area to the spray diameter. Supernatant was removed from the target well and 10 µl delivery solution containing 10-kDa dextran was sprayed onto the cells. Following a 2 min incubation at RT, 200 µl 0.5×-PBS was added and cells were incubated for a further 30 sec. This solution was then removed and 400 µl culture medium was added. This method resulted in successful delivery of 10-kDa dextran into cells with efficiencies of greater than 50% and little to no toxicity compared with untreated cells (FIG. 21 and FIG. 22).

Figure 23:
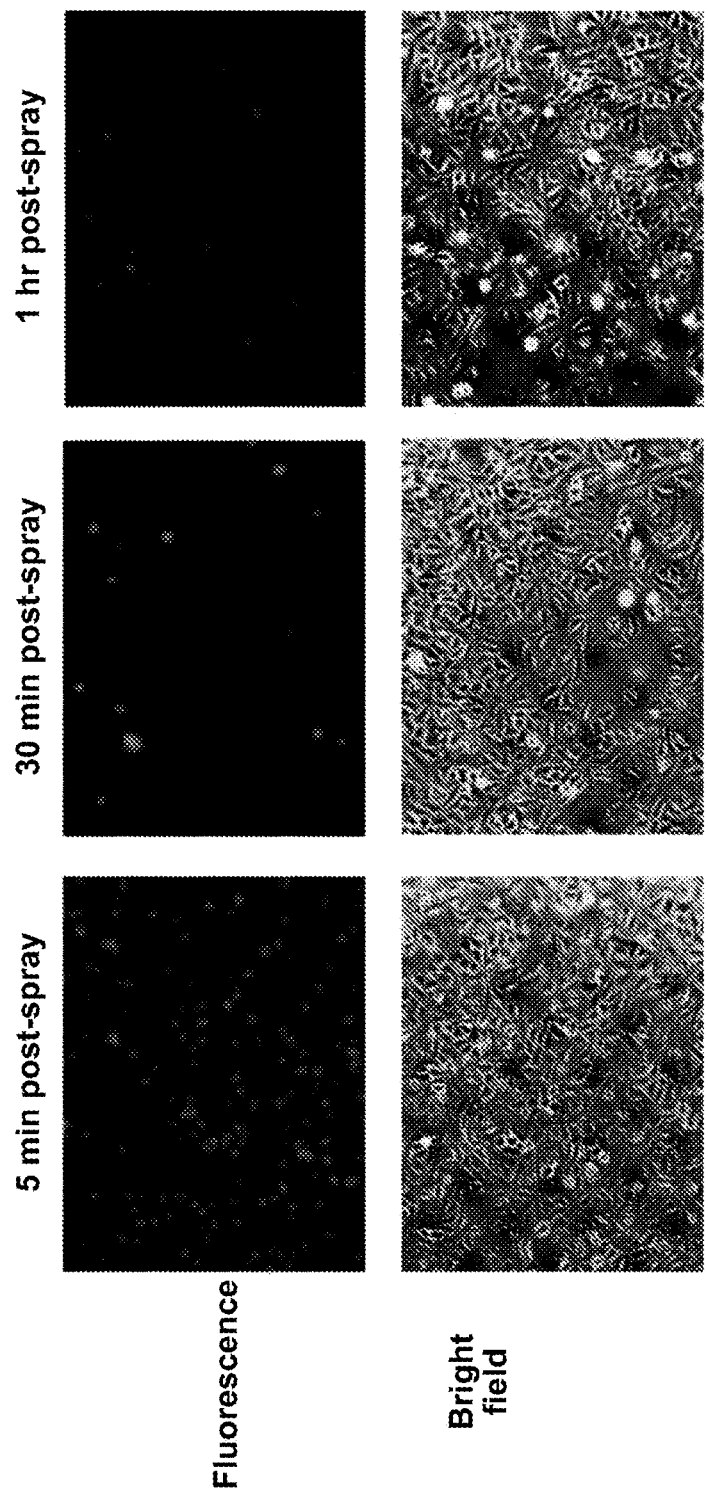
FIG. 23 is a photomicrograph showing the time course of permeabilisation in A549 cells. Delivery solution was sprayed in the absence of payload, and PI was subsequently added to the culture medium at time points up to 60 minutes post-spray to detect permeabilised cells. While PI uptake was visible at 5 min post-spray, the number of PI-positive cells was substantially reduced by 30 minutes and 60 minutes post-spray. A 10× magnification is shown in the photomicrograph.
Figure 24:
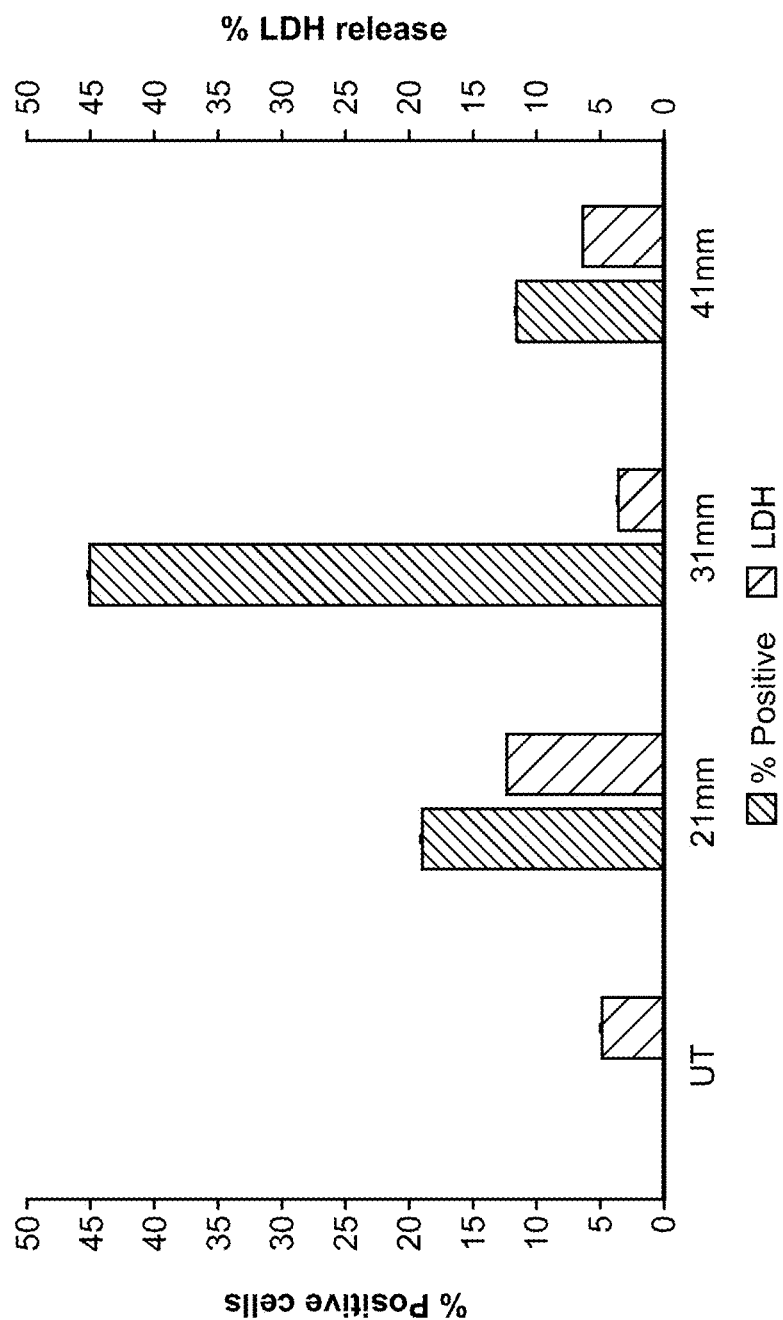
FIG. 24 is a graph illustrating the effect of the distance between the sprayhead and the cells on delivery efficiency and cell toxicity. 10-kDadextran-Alexa488 was delivered to A549 cells. The distance between the sprayhead and the cells was varied (including 21 mm, 31 mm and 41 mm). A distance of 31 mm was optimal for both efficiency and toxicity (n=3).
Figure 25:
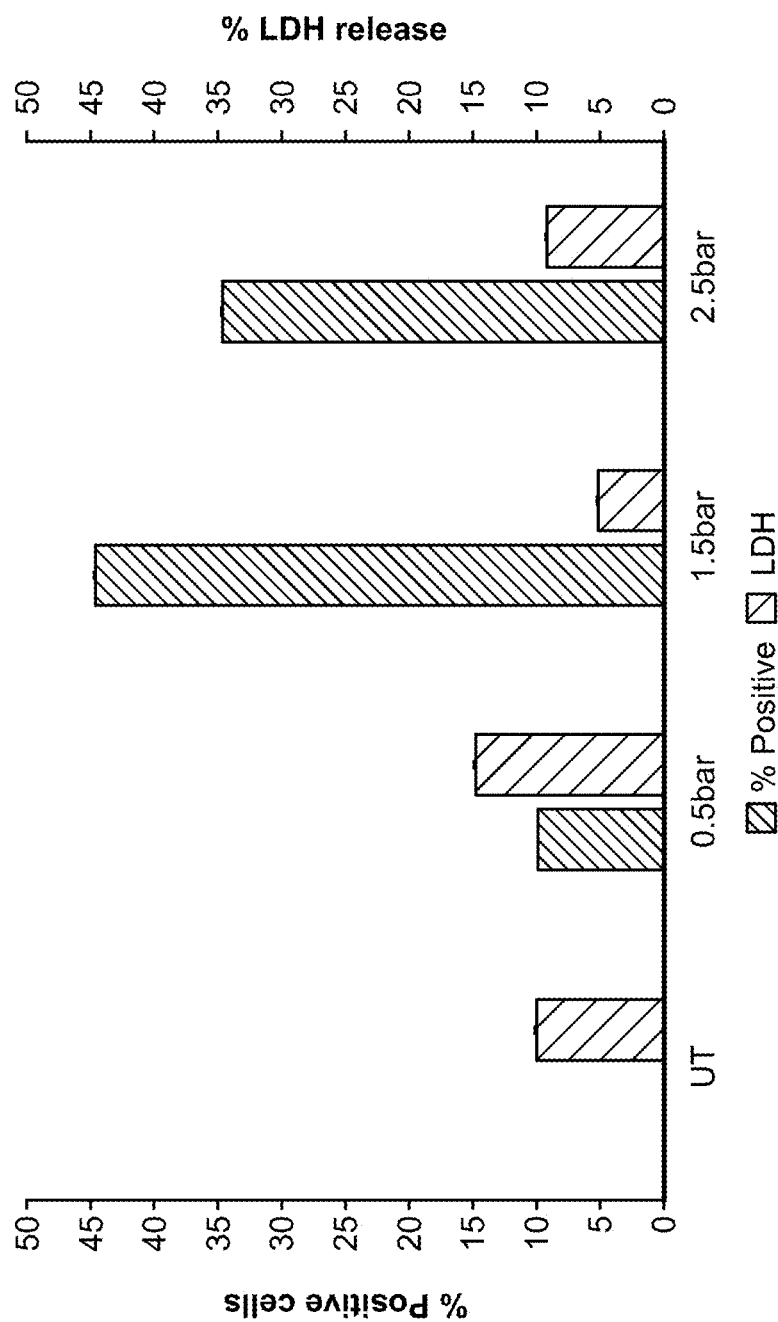
FIG. 25 is a graph illustrating the effect of spray pressure on delivery efficiency and cell toxicity. 10-kDadextran-Alexa488 was delivered to A549 cells, and the spray pressure was varied (including 0.5 bar, 1.5 bar and 2.5 bar). A pressure of 1.5 bar was optimal for both delivery efficiency and cell toxicity (n=3).
Figure 26:
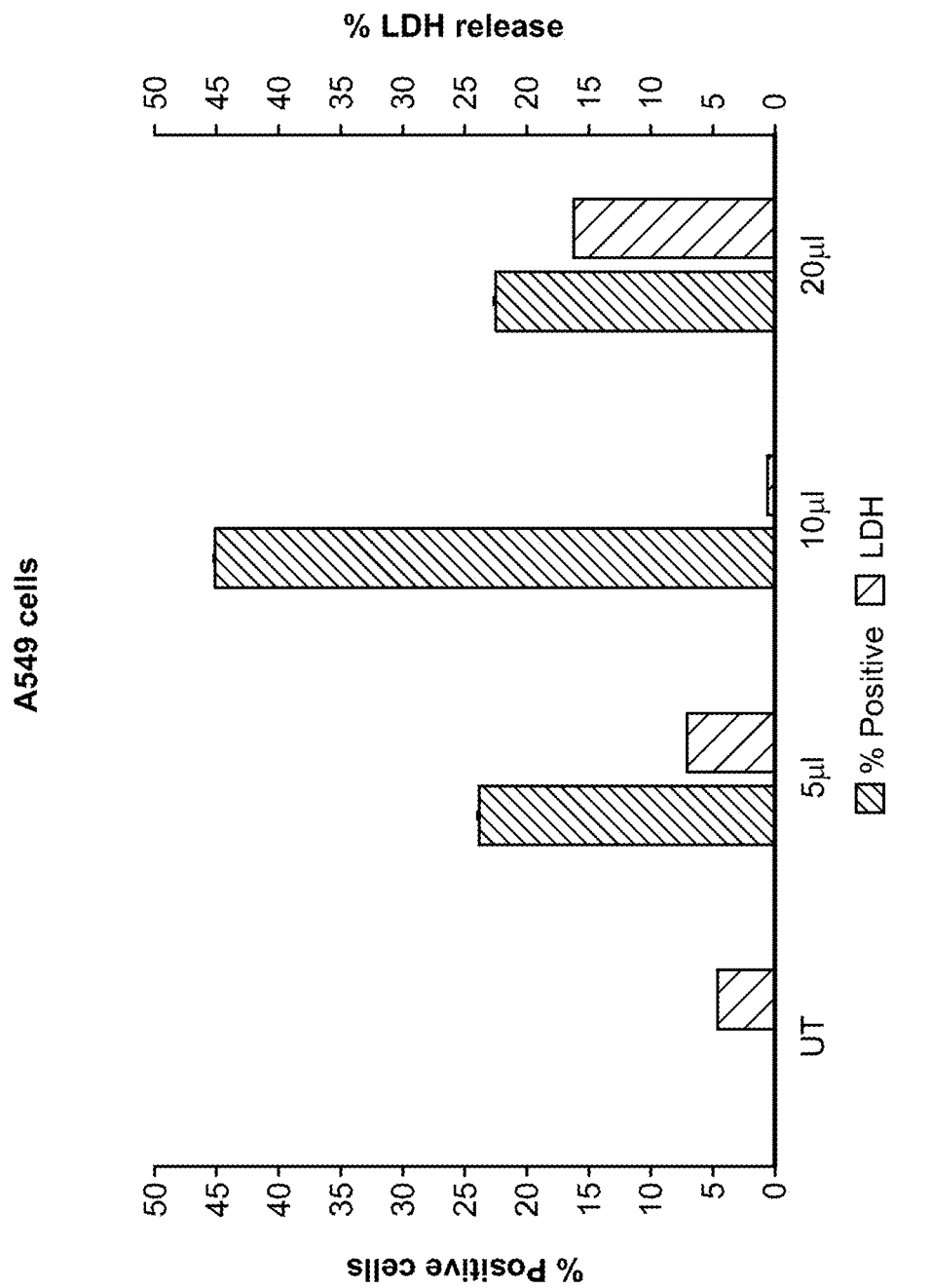
FIG. 26 is a graph illustrating the effect of the volume of delivery solution on delivery efficiency and cell toxicity. 10-kDadextran-Alexa488 was delivered to A549 cells at 80-90% confluency in 48-wellplates, and the volume of delivery solution was varied (including 5 μL, 10 μL and 20 μL). A volume of 10 μl was optimal for both delivery efficiency and cell toxicity (n=3).
Figure 27:
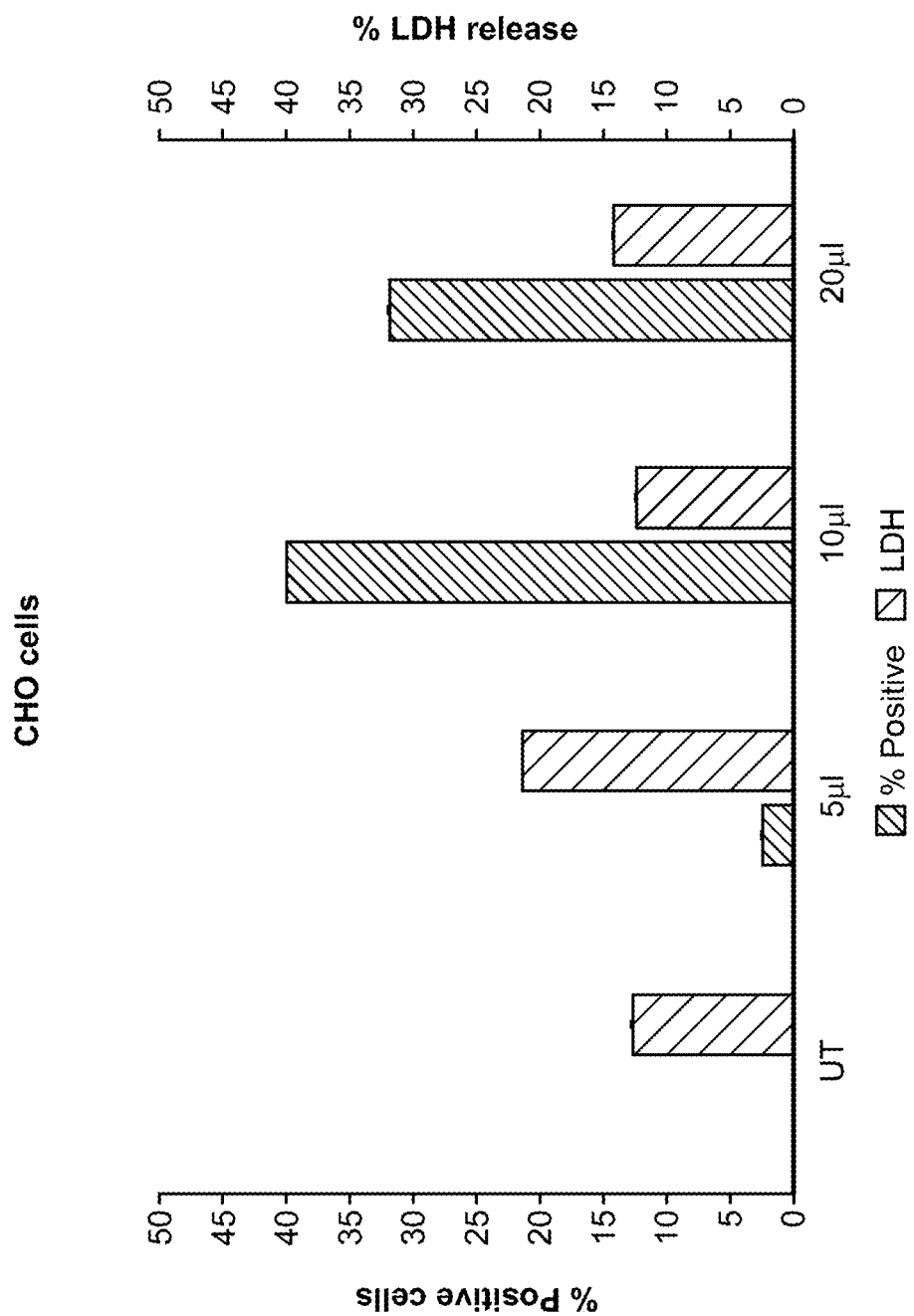
FIG. 27 is a graph illustrating the effect of the volume of delivery solution on delivery efficiency and cell toxicity. 10-kDadextran-Alexa488 was delivered to CHO cells at 80-90% confluency in 48-wellplates, and the volume of delivery solution was varied (including 5 μL, 10 μL and 20 μL). A volume of 10 μl was optimal for both delivery efficiency and cell toxicity (n=3).
Figure 28:
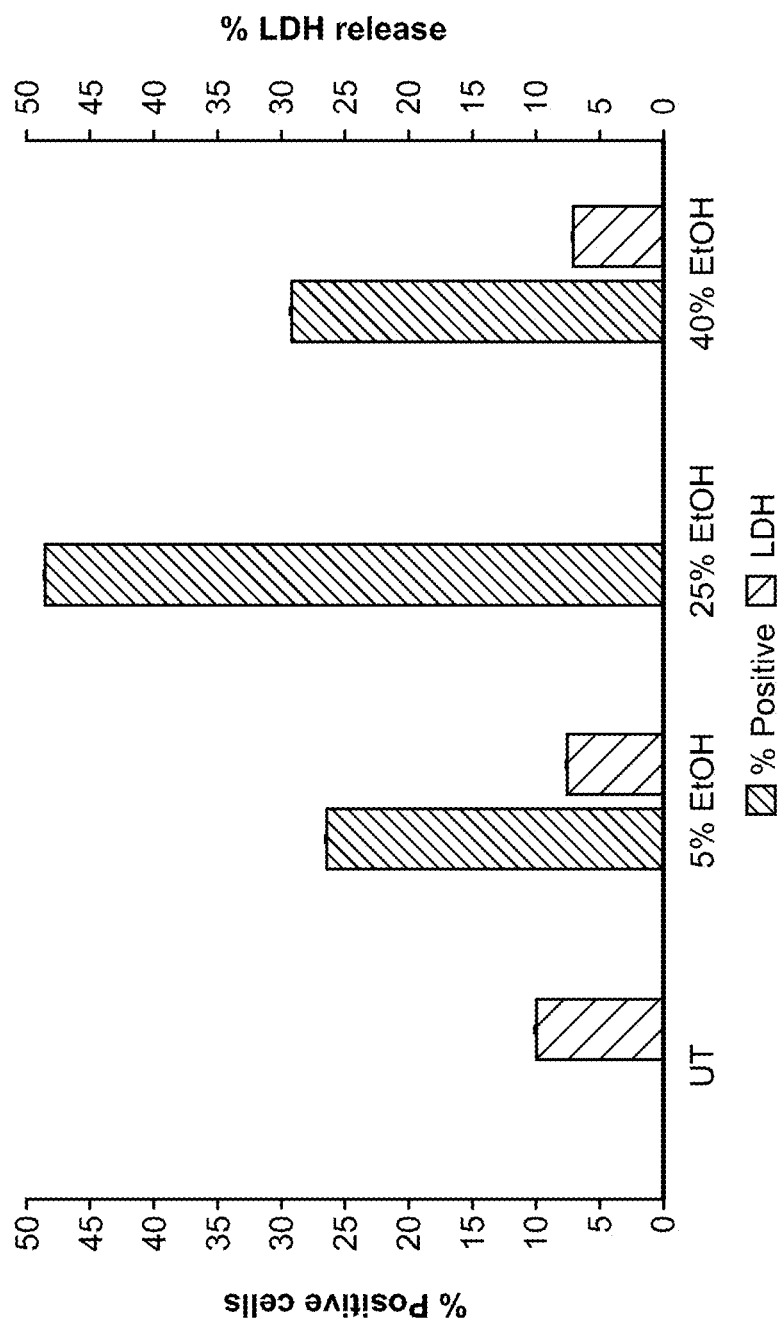
FIG. 28 is a graph illustrating the effect of ethanol concentration on delivery efficiency and cell toxicity. 10-kDadextran-Alexa488 was delivered to A549 cells, and the concentration of ethanol in the delivery solution was varied. A concentration of 25% was optimal for both efficiency and toxicity (n=3).

Having established a technique for reversibly permeabilising cells, the time taken for recovery of the cells was examined. Delivery solution was sprayed in the absence of payload and propidium iodide (PI) was subsequently added to the culture medium at time points up to 1 hour post-spray in order to detect permeabilised cells. While PI uptake was visible at 5 min post-spray, the number of PI-positive cells was substantially reduced by 30 min and 60 min post-spray, as illustrated in FIG. 23.

Example Optimal Parameters.

Several parameters were optimized in the course of developing the technique. The distance of the sprayhead from the cells, the pressure of the spray, the volume of delivery solution sprayed per well and the concentration of ethanol were fine tuned to maximize delivery efficiency while minimizing toxicity (FIGS. 25-29). A distance of 31 mm between the sprayhead and the cells, a spray pressure of 1.5 bar, a volume of 10 μl for 48-well plates and an ethanol concentration of 25% were the parameters that produced optimal delivery efficiencies and toxicity levels.

Example 2

Effect of Delivering a Molecule Having an Average Molecular Weight of Up to 15,000 Da Across a Plasma Membrane According to the Present Subject Matter.

In this example, a FITC-labelled siRNA molecule having an average molecular weight of 15,000 Da was delivered to cells using an apparatus according to the present subject matter. The siRNA molecules were introduced to a composition, which was an aqueous solution including 32 mM sucrose, 12 mM KCl, 12 mM ammonium acetate, 5 mM hepes, a pH of about 7.4, 20, 30, or 40% (v/v) of ethanol; and 6.6 μM molecules to be delivered; in order to form a matrix. 1 μL of matrix was delivered to an area of 0.065-0.085 $cm^2$, such that the matrix was contacted with the plasma membrane of the cells either directly using a micropipette or using an apparatus as described herein. The relative amount of molecules delivered (the amount of fluorescence) and the cell viability (amount of viable cells) was assessed and expressed as a percentage. The results are illustrated in FIG. 4.

As is illustrated in FIG. 4, delivery of a molecule having an average molecular weight of up to 15,000 Da using a method of the present subject matter (black bars) increases the delivery rate of the molecule (e.g., percent of cells showing successful delivery of the molecule) compared to delivery of the molecule by contacting with the plasma membrane of the cells directly using a micropipette (hashed lines). Indeed, in a composition including 30 or 40% (v/v) of ethanol, and delivery of the resultant matrix directly using a micropipette, no delivery of molecules was detected in viable cells.

Example 3

Effect of Delivering a Molecule Having an Average Molecular Weight of Up to 1,000 Da Across a Plasma Membrane According to the Current Subject Matter In this example, a propidium iodide molecule having an average molecular weight of 668 Da was delivered to cells using a method according to the present subject matter. The molecules were introduced to a composition, which was an aqueous solution including 32 mM sucrose, 12 mM KCl, 12 mM ammonium acetate, 5 mM hepes, a pH of about 7.4, 20 or 40% (v/v) of ethanol; and 150 μM molecules to be delivered; in order to form a matrix. 1 μL of matrix was delivered to an area of 0.065-0.085 $cm^2$, such that the matrix was contacted with the plasma membrane of the cells either directly using a micropipette or an apparatus as described above herein. The results are illustrated in FIG. 4.

As is illustrated in FIG. 5, delivery of a molecule having an average molecular weight of up to 668 Da in a matrix using a method according to the present subject matter (black bars) increases the delivery rate of the molecule (e.g., percent of cells showing successful delivery of the molecule), (y-axis shows percent delivered, and x-axis shows percent ethanol) compared to delivery of the molecule by contacting with the plasma membrane of the cells directly using a micropipette (hashed lines). Indeed, in a composition including 40% (v/v) of ethanol, and delivery of the resultant matrix directly using a micropipette, no delivery of molecules was detected in viable cells.

Example 4

Delivering molecules of more than one molecular weight across a plasma membrane. In this example, a first molecule of propidium iodide having an average molecular weight of 668 Da and a second molecule of FITC-labelled dextran having a molecular weight of 40,000 were both simultaneously delivered to cells using an apparatus of the present subject matter. The first and second molecules were simultaneously introduced to a composition, which was an aqueous solution including 32 mM sucrose, 12 mM KCl, 12 mM ammonium acetate, 5 mM hepes; a pH of about 7.4, 25% (v/v) of ethanol; and 150 μM molecules to be delivered; in order to form a matrix. 1 μL of matrix was delivered to an area of 0.065-0.085 $cm^2$, such that the matrix was contacted with the plasma membrane of the cells in the form of an aerosol using the method of the present subject matter. The results are illustrated in FIGS. 6A-6C.

As is illustrated in FIG. 6A, delivery of a first molecule having an average molecular weight of 668 Da in a matrix using the present subject matter results in delivery of the molecule into the cell. FIG. 6B illustrates simultaneous delivery of a second molecule having an average molecular weight of 40,000 Da in the same matrix using the present subject matter results in simultaneous delivery of the molecule into the cell. The simultaneous delivery is illustrated in FIG. 6C.

Example 5

Effect of Delivering a Molecule Having an Average Molecular Weight of Up to 500,000 Da Across a Plasma Membrane According to the Present Subject Matter In this example, a molecule of FITC-labelled dextran having an average molecular weight of 10,000 Da was delivered to cells using an apparatus according to the present subject matter. The molecules were introduced to a composition, which was an aqueous solution including 32 mM sucrose, 12 mM KCl, 12 mM ammonium acetate, 5 mM hepes; a pH of about 7.4; 25% (v/v) of ethanol; and 150 μM molecules to be delivered; in order to form a matrix. 1 μL of matrix was delivered to an area of 0.065-0.085 $cm^2$, such that the matrix was contacted with the plasma membrane of the cells either directly using a micropipette or an apparatus of the present subject matter. The results are illustrated in FIG. 7.

As is illustrated in FIG. 7, delivery of a molecule having an average molecular weight of up to 500,000 Da in a matrix using a method of the present subject matter (black bar) increases the delivery rate of the molecule (e.g., percent of cells showing successful delivery of the molecule), (the y-axis shows percent delivered, and x-axis indicates percent ethanol) compared to delivery of the molecule by contacting with the plasma membrane of the cells directly using a micropipette (hashed lines). Indeed, in a composition including 25% (v/v) of ethanol, and delivery of the resultant matrix directly using a micropipette, no delivery of molecules was detected in viable cells.

Example 6

Effect of Contacting Cells with a Second Composition Including 68 mM NaCl, 1.4 mM KCl, 5 mM $Na_2HPO4$, and 0.9 mM $KH_2PO_4$.

In this example, a FITC-labelled siRNA molecule having an average molecular weight of 15,000 Da was delivered to cells using an apparatus according to the present subject matter. Following delivery of molecules to cells, cells were contacted with 200 μL of a second composition including one of: Dulbecco's Modified Eagle's Medium (DMEM) with fetal bovine serum (FBS); DMEM without FBS; distilled water (H$_2$O); an aqueous solution of 137 mM NaCl, 2.7 mM KCl, 10 mM Na$_2$HPO$_4$, and 1.8 mM KH$_2$PO$_4$ (1×PBS); an aqueous solution of 68 mM NaCl, 1.4 mM KCl, 5 mM Na$_2$HPO$_4$, and 0.9 mM KH$_2$PO$_4$ (0.5×PBS); or an aqueous solution of 13.7 mM NaCl, 0.3 mM KCl, 1.0 mM Na$_2$HPO$_4$, and 0.18 mM KH$_2$PO$_4$ (1×PBS) for 30 seconds before addition of culture medium and assessment of delivery using fluorescence microscopy as described herein. The results are shown in FIG. 8, which illustrates.

Figure 8:
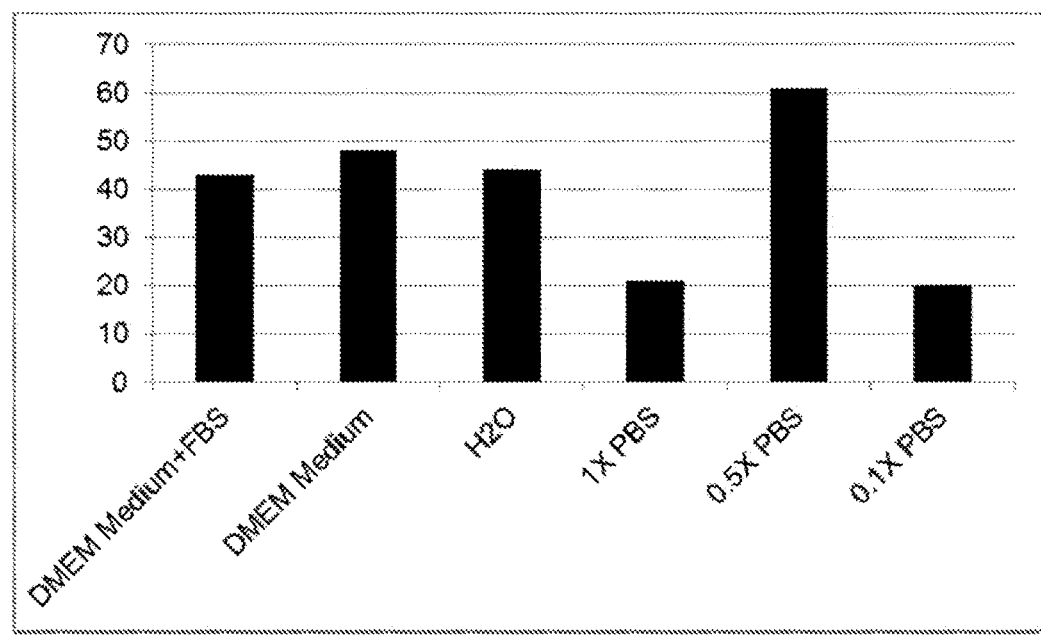
FIG. 8 is a graph illustrating the effect of contacting cells with a second composition including 68 mM NaCl, 1.4 mM KCl, 5 mM $Na_2HPO_4$, and 0.9 mM $KH_2PO_4$ according to the present subject matter.

As illustrated in FIG. 8, an aqueous solution of 68 mM NaCl, 1.4 mM KCl, 5 mM Na$_2$HPO$_4$, and 0.9 mM KH$_2$PO$_4$ (0.5×PBS) is preferred to maintain cell viability in a method according to the present subject matter (y-axis indicates percent delivered).

Example 7

Delivering Molecules of Different Molecular Weight Across a Plasma Membrane

In this example, molecules of propridium iodide (668 Da), FITC-labelled siRNA (15,000 Da), Dy547-labelled miRNA (15,000 Da), FITC-labelled dextran (40,000 Da), and FITC-labelled dextran (500,000 Da) were each delivered to cells using an apparatus according to the present subject matter. The molecules were each separately introduced to a composition, which was an aqueous solution including 32 mM sucrose, 12 mM KCl, 12 mM ammonium acetate, 5 mM hepes; a pH of about 7.4, wherein the composition included 25% (v/v) of ethanol; and 150 µM molecules to be delivered; in order to form a matrix. 1 µL of each matrix (each containing a different molecule to be delivered) was delivered to an area of 0.065-0.085 cm$^2$, such that the matrix was contacted with the plasma membrane of the cells either directly using a micropipette or by a method according to the present subject matter. Cells were visualized at 0 hour (propidium iodide) or at 24 hours post-delivery (siRNA-FITC, miRNA-Dy547 and dextran-FITC). Photomicrographs showing (A) fluorescence and (B) phase contrast were obtained using an Olympus IX71 Inverted Microscope. The results are illustrated in FIG. 9.

Figure 9:
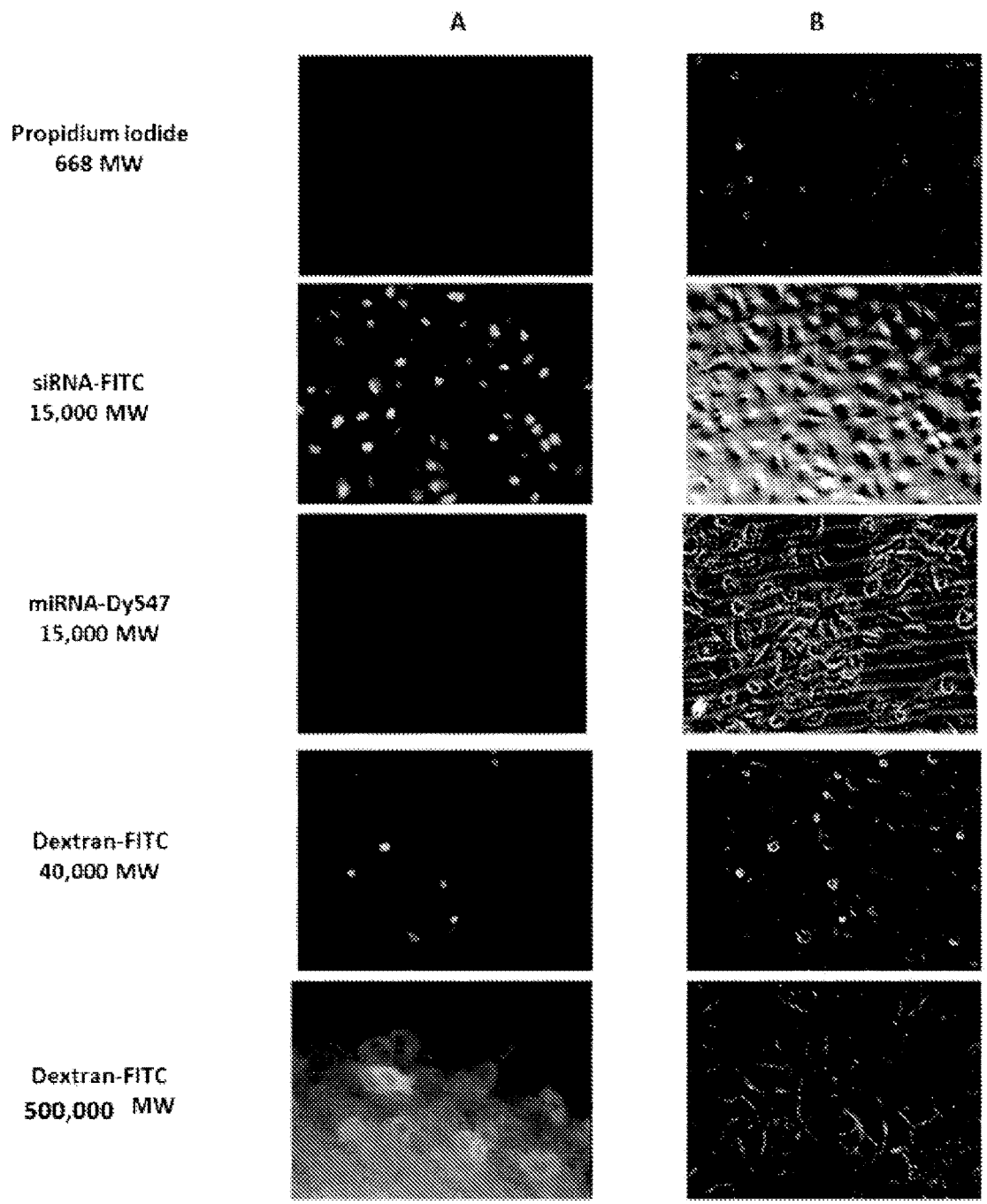
FIG. 9 is a photomicrograph illustrating delivering molecules of varying molecular weights using a method according to the present subject matter.
Figure 29:
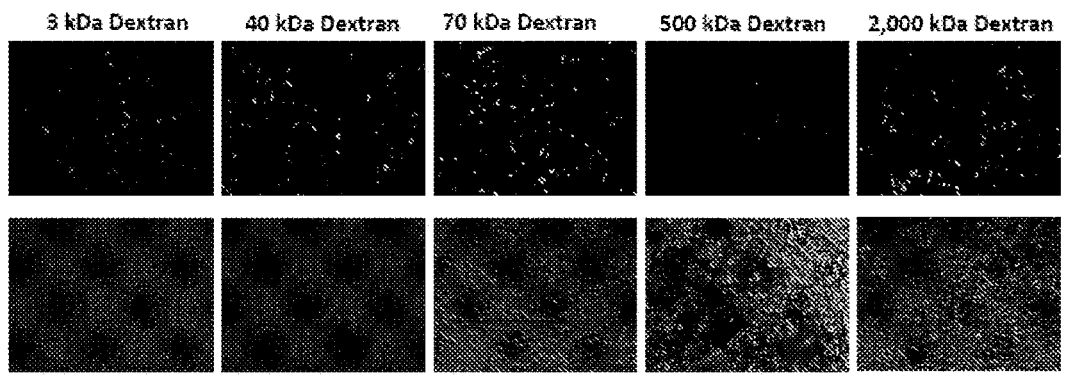
FIG. 29 is a photomicrograph illustrating the delivery of a wide range of molecular sizes of dextrans, including very high molecular weight dextran (2,000 kDa) that can be delivered by the method of the current subject matter. The photomicrograph shows a 10× magnification.
Figure 43:
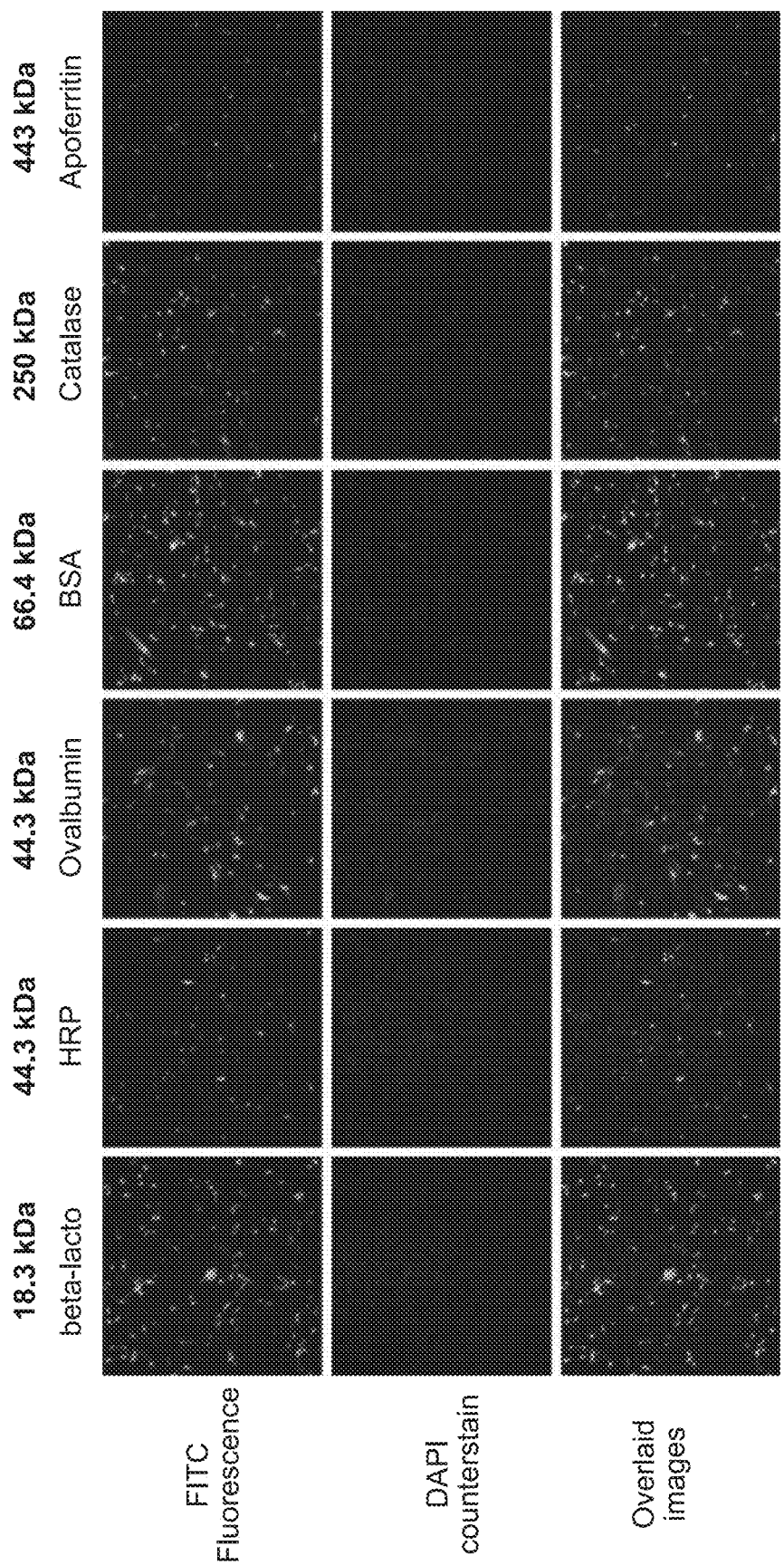
FIG. 43 is a photomicrograph showing the effects of delivery of proteins into Chinese hamster ovary (CHO) cells. A wide range of proteins were labeled with FITC and delivered into CHO cells, including β-lactoglobulin, horseradish peroxidase (HRP), ovalbumin, bovine serum albumin (BSA), catalase, and apoferritin.

As illustrated in FIG. 9, molecules of varying molecular weights can be successfully delivered to cells using an apparatus according to the present subject matter. Additionally, varying molecular weights of dextran (e.g., 3 kDa, 40 kDa, 70 kDa, 500 kDa, and 2,000 kDa), and proteins (e.g., beta-lactoglobulin, HRP, ovalbumin, BSA, catalase, and apoferritin) can be successfully delivered, as shown in FIGS. 29 and 43, respectively.

The present subject matter therefore can provide an apparatus for delivering a molecule across a plasma membrane, and which enables the delivery of molecules to living cells by reversible permeabilisation of the or each cell. Reversible permeabilisation allows each cell to be permeable, optionally temporarily permeable, thereby allowing uptake of molecules into the cell. Advantageously, permeability can be reversed before unacceptably high levels of cell death occur.

Example 8

Effect of Solute Content on the Delivery of a Molecule Having an Average Molecular Weight of Up to 15,000 Da.

Figure 10:
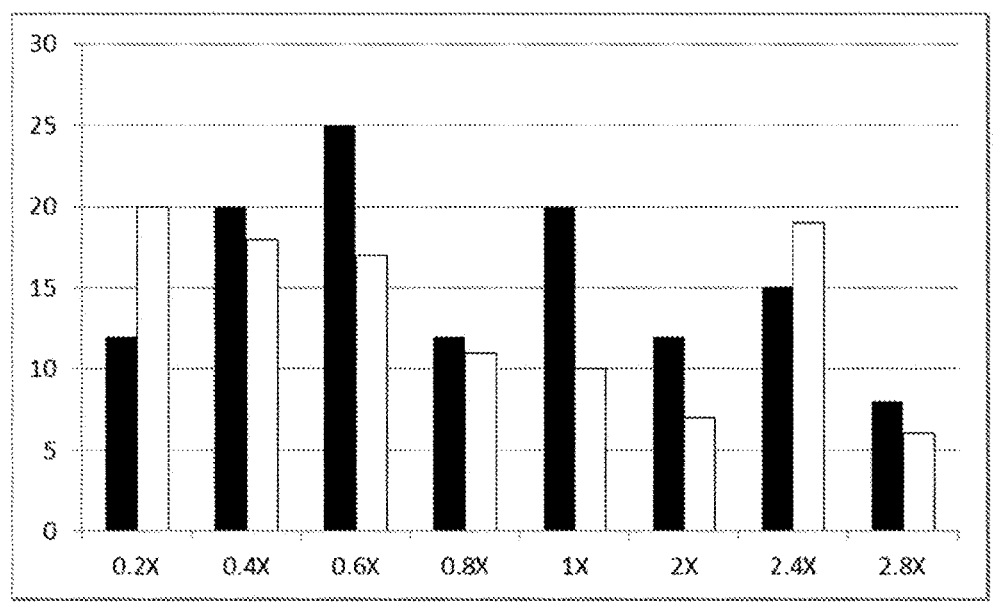
FIG. 10 is a graph illustrating the effect of solute content on the delivery of a molecule having an average molecular weight of up to 15,000 Da.

In this example, an siRNA molecule having an average molecular weight of 15,000 Da was delivered to cells as generally described herein above. The composition used was an aqueous solution having a pH of about 7.4, wherein the composition included 25% (v/v) of ethanol; and 3.3 µM molecules to be delivered. A 1× solution was prepared by adding sucrose, KCl, ammonium acetate, and hepes to a final concentration of 32 mM sucrose, 12 mM KCl, 12 mM ammonium acetate, and 5 mM hepes. Further test solutions were prepared with varying solute (sucrose, KCl, ammonium acetate, and hepes) concentrations of 0.2×, 0.4×, 0.6×, 0.8×, 2×, 2.4×, and 2.8×. The results are illustrated in FIG. 10.

As is illustrated in FIG. 9, for delivery of a molecule having an average molecular weight of up to 15,000 Da, a composition including a solute concentration of sucrose, KCl, ammonium acetate, and hepes of 1×-2×, optionally 1× is preferred (black bars), given that cell toxicity (white bars) is minimal at these concentrations. This equates to a solute concentration of 32-64 mM sucrose, 12-24 mM KCl, 12-24 mM ammonium acetate, and 5-10 mM hepes; further optionally 32 mM sucrose, 12 mM KCl, 12 mM ammonium acetate, and 5 mM hepes.

Example 9

Effect of Alcohol Concentration on the Delivery of a Molecule Having an Average Molecular Weight of Up to 15,000 Da In this example, an siRNA molecule having an average molecular weight of 15,000 Da was delivered to cells as generally described herein above. The composition used was an aqueous solution including 32 mM sucrose, 12 mM KCl, 12 mM ammonium acetate, and 5 mM hepes, a pH of about 7.4, 6.6 µM molecules to be delivered, and 5, 10, 20, 30, and 40% (v/v) of ethanol. The results are illustrated in FIG. 11.

Figure 11:
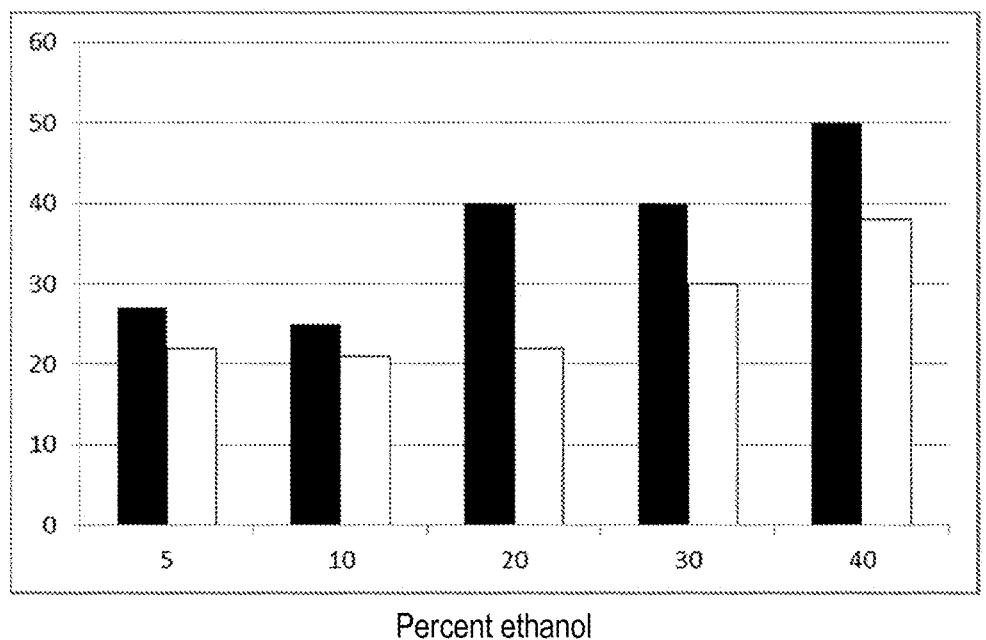
FIG. 11 is a graph illustrating the effect of alcohol concentration on the delivery of a molecule having an average molecular weight of up to 15,000 Da.

As is illustrated in FIG. 11, for delivery of a molecule having an average molecular weight of up to 15,000 Da, a composition including 2-45% (v/v) of the alcohol, optionally 20-30% (v/v) of the alcohol, further optionally 25% (v/v) of the alcohol is preferred (black bars) while minimizing cell toxicity (white bars).

As a comparative test, an siRNA molecule having an average molecular weight of 15,000 Da was delivered to cells as generally described herein above, wherein the composition used was an aqueous solution including 32 mM sucrose, 12 mM KCl, 12 mM ammonium acetate, 5 mM hepes, a pH of about 7.4, 6.6 µM molecules to be delivered, and 5, 10, 20, and 30% (v/v) of methanol. The results are illustrated in FIG. 12.

Figure 12:
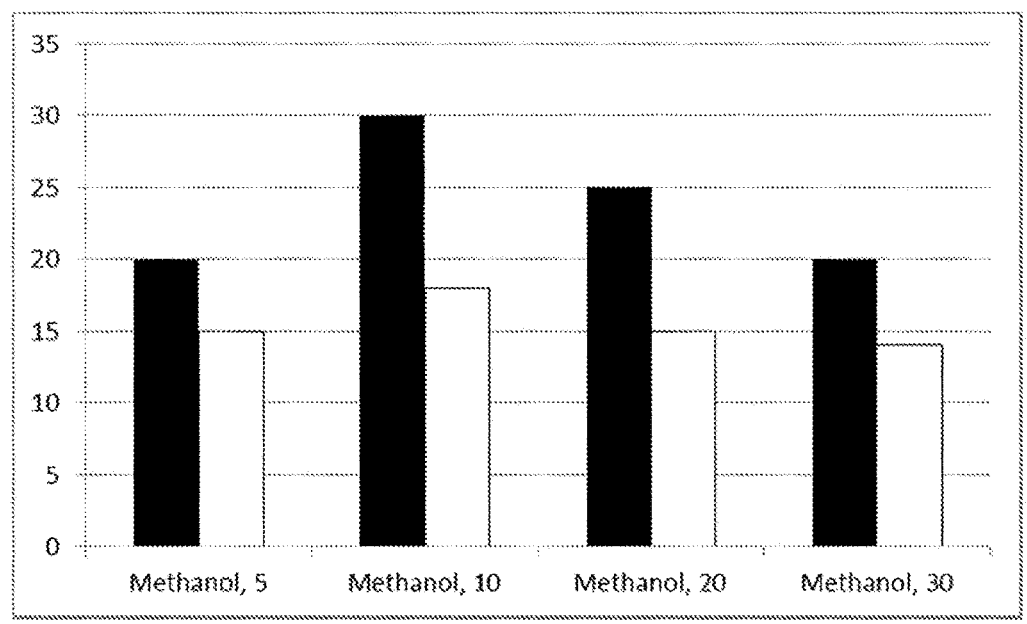
FIG. 12 is a graph illustrating the effect of alcohol concentration on the delivery of a molecule having an average molecular weight of up to 15,000 Da.
Figure 13:
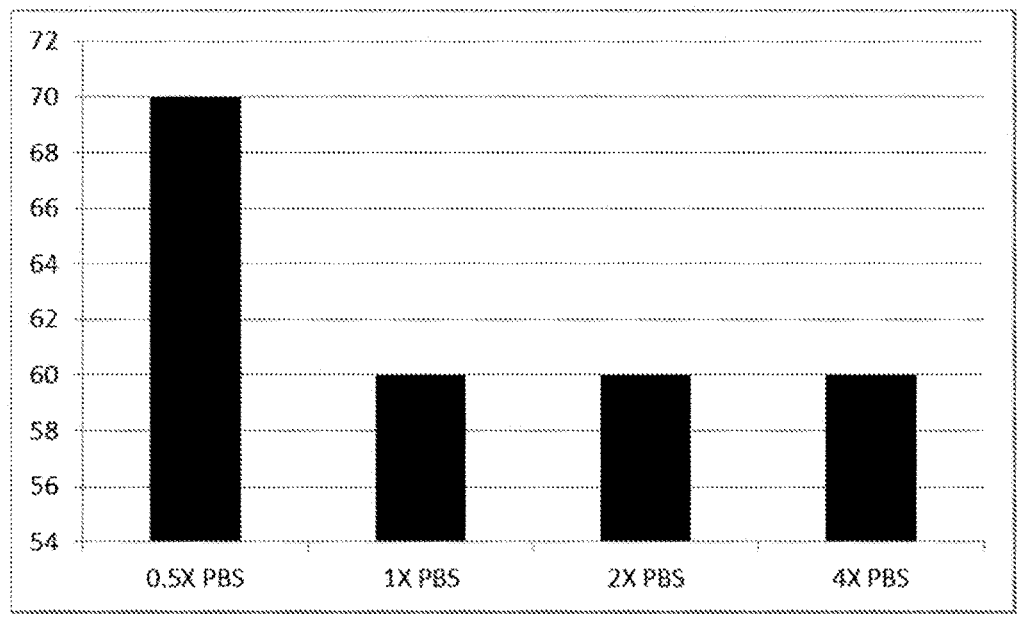
FIG. 13 is a graph illustrating the effect of salt concentration on the delivery of a molecule having an average molecular weight of up to 15,000 Da.

As is illustrated in FIG. 12, for delivery of a molecule having an average molecular weight of up to 15,000 Da, a composition including 2-45% (v/v) of the alcohol, optionally 10-20% (v/v) of the alcohol, further optionally 20% (v/v) of the alcohol is preferred (black bars) while minimizing cell viability (white bars).

Example 10

Effect of Salt Content on the Delivery of a Molecule Having an Average Molecular Weight of Up to 1,000 Da In this example, a propridium iodide molecule having an average molecular weight of 668 Da was delivered to cells as generally described herein above. The composition used was an aqueous solution having a pH of about 7.4, wherein the composition included 25% (v/v) of ethanol; 150 µM molecules to be delivered. The test solutions were prepared with 25% of 0.5×, 1×, 2×, and 4× phosphate buffered saline (PBS), which equates to a salt content of 19.0 mM, 37.9 mM, 75.8 mM, and 151.6 mM. The results are illustrated in FIG. 12.

Example 11

Effect of Alcohol Concentration on the Delivery of a Molecule Having an Average Molecular Weight of Up to 1,000 Da In this example, a propridium iodide molecule having an average molecular weight of 668 Da was delivered to cells as generally described herein above. The composition used was an aqueous solution including 32 mM sucrose, 12 mM KCl, 12 mM ammonium acetate, 5 mM hepes, a pH of about 7.4, 150 µM molecules to be delivered, and 5, 10, 20, 30, and 40% (v/v) of ethanol. The results are illustrated in FIG. 14.

Figure 14:
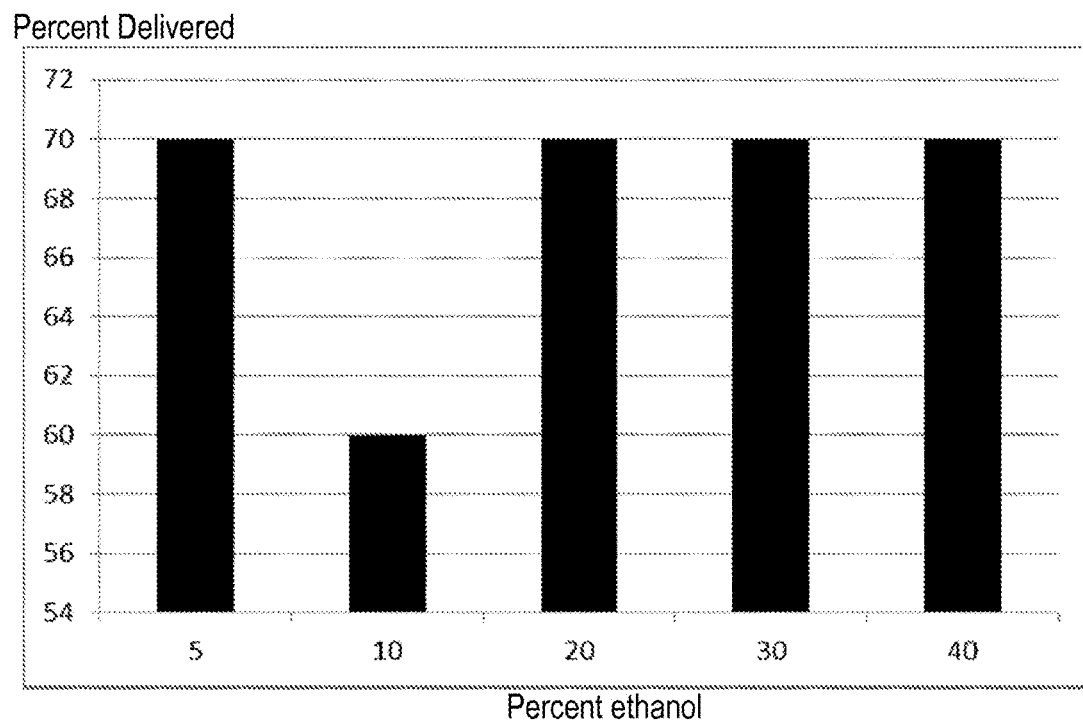
FIG. 14 is a graph illustrating the effect of alcohol concentration on the delivery of a molecule having an average molecular weight of up to 1,000 Da.

As is illustrated in FIG. 14, for delivery of a molecule having an average molecular weight of up to 1,000 Da, a composition including 2-45% (v/v) of the alcohol, optionally 20-30% (v/v) of the alcohol, further optionally 25% (v/v) of the alcohol is preferred.

As a comparative test, a propridium iodide molecule having an average molecular weight of 668 Da was delivered to cells as generally described herein above, wherein the composition used was an aqueous solution including 32 mM sucrose, 12 mM KCl, 12 mM ammonium acetate, 5 mM hepes, a pH of about 7.4, 150 µM molecules to be delivered, and 5, 10, 20, and 30% (v/v) of methanol. The results are illustrated in FIG. 14.

Figure 15:
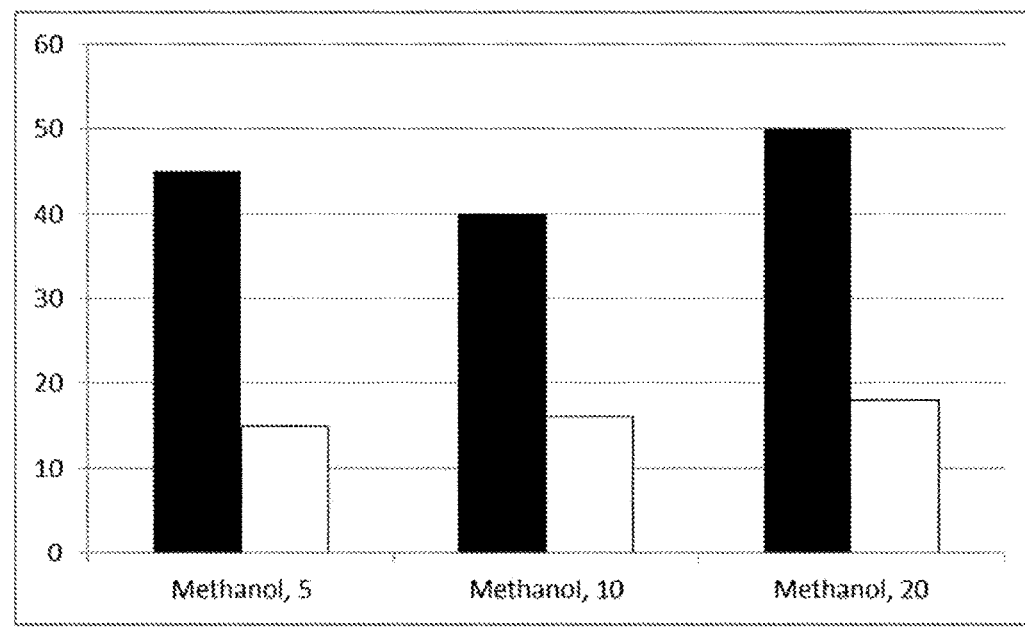
FIG. 15 is a graph illustrating the effect of alcohol concentration on the delivery of a molecule having an average molecular weight of up to 1,000 Da.

As is illustrated in FIG. 15, for delivery of a molecule having an average molecular weight of up to 1,000 Da, a composition including 5-20% (v/v) of the alcohol, optionally 5, 10, or 20% (v/v) of the alcohol is preferred (black bars) while minimising cell toxicity (white bars).

As a further comparative test, a propridium iodide molecule having an average molecular weight of 668 Da was delivered to cells as generally described herein above, wherein the composition used was an aqueous solution including 32 mM sucrose, 12 mM KCl, 12 mM ammonium acetate, 5 mM hepes, a pH of about 7.4, 150 µM molecules to be delivered, and 2% (v/v) of butanol. The results are illustrated in FIG. 16.

Figure 16:
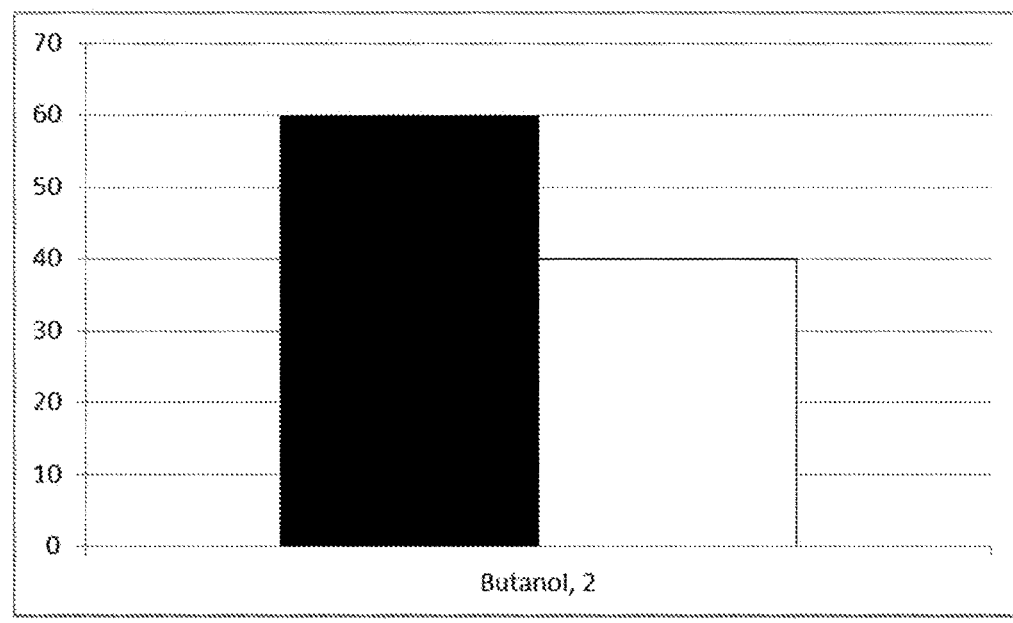
FIG. 16 is a graph illustrating the effect of alcohol concentration on the delivery of a molecule having an average molecular weight of up to 1,000 Da.

As is illustrated in FIG. 16, for delivery of a molecule having an average molecular weight of up to 5,000 Da, a composition including 2% (v/v) of butanol is preferred (black bars) while minimizing cell toxicity (white bars).

The present subject matter therefore provides a method for delivering a molecule across a plasma membrane, and which enables the delivery of molecules to living cells by reversible permeabilization of the cells or each cell. Reversible permeabilization allows the cells or each cell to be permeable, optionally temporarily permeable, thereby allowing uptake of molecules into the cell. Advantageously, permeability can be reversed before unacceptably high levels of cell death occur.

Example 12

Effect of delivering a molecule having an average molecular weight of up to 40,000 Da across a plasma membrane according to the current subject matter.

In this example, a molecule of FITC-labelled dextran having an average molecular weight of 40,000 Da was delivered to cells using an apparatus according to the current subject matter. The molecules were introduced to a composition, which was an aqueous solution including 32 mM sucrose, 12 mM KCl, 12 mM ammonium acetate, 5 mM hepes; a pH of about 7.4; 40% (v/v) of ethanol; and 10 µM molecules to be delivered; in order to form a matrix. 1 µL of matrix was delivered to an area of 0.065-0.085 $cm^2$, such that the matrix was contacted with the plasma membrane of the cells either directly using a micropipette or an apparatus of the current subject matter.

Figure 7:
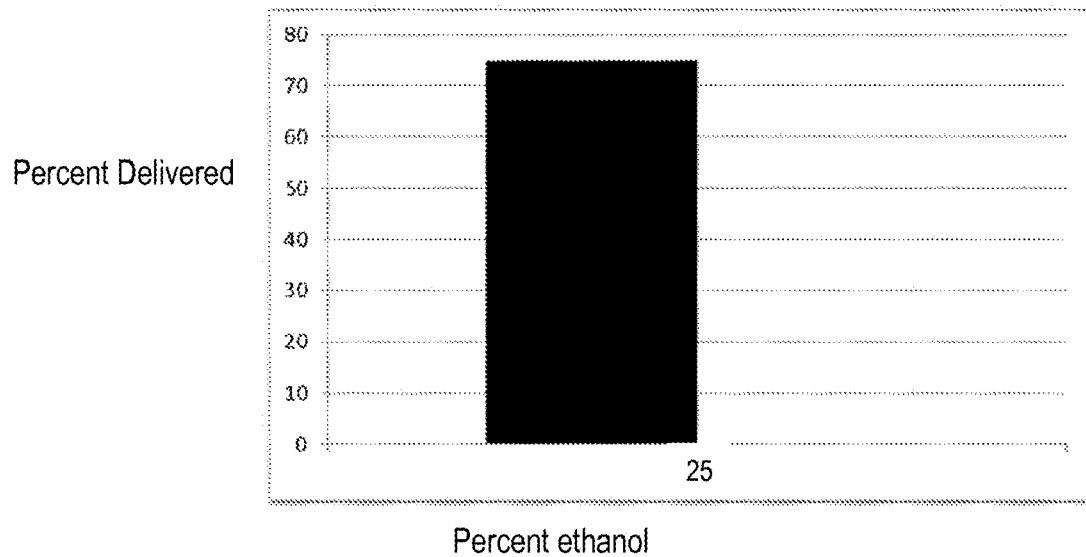
FIG. 7 is a graph illustrating the effect of delivering a molecule having an average molecular weight of up to 500,000 Da across a plasma membrane according to the present subject matter.

As is illustrated in FIG. 7, delivery of a molecule having an average molecular weight of up to 40,000 Da in a matrix using the present subject matter (black bars) increases the delivery rate of the molecule compared to delivery of the molecule by contacting with the plasma membrane of the cells directly using a micropipette (hashed lines). Indeed, in a composition including 40% (v/v) of ethanol, and delivery of the resultant matrix directly using a micropipette, no delivery of molecules was detected in viable cells.

Example 13

Effect of Delivering Molecules with a Range of Molecule Types and Sizes

Figure 30:
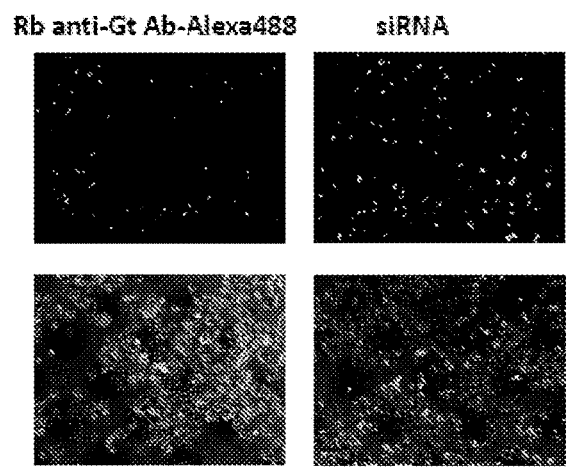
FIG. 30 is a photomicrograph illustrating the delivery of a wide range of molecular sizes of molecules, including full length antibodies that can be delivered by methods of the current subject matter. The photomicrograph shows a 10× magnification.
Figure 31:
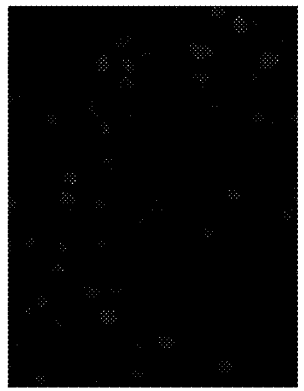
FIG. 31 is a photomicrograph illustrating the effect of co-delivery of 4',6-diamidino-2-phenylindole (DAPI), Mitotracker Red CMXRos and Phalloidin-Alexa488 to A549 cells.
Figure 31:
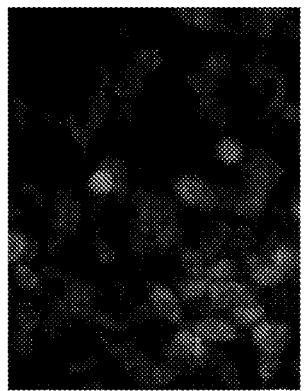
Figure 31:
Figure 31:
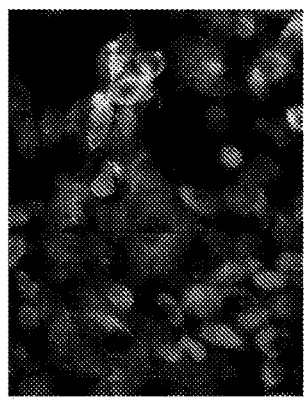
Figure 32:
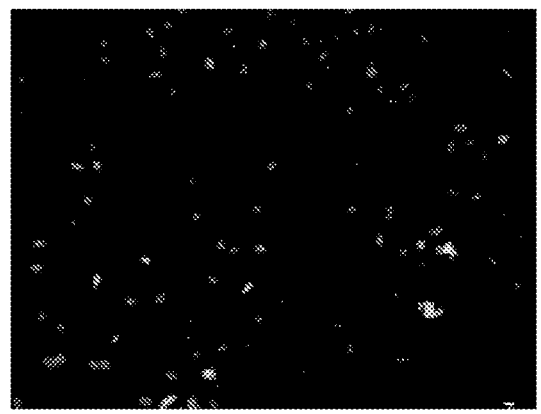
FIG. 32 is a photomicrograph illustrating the effect of co-delivery of both 10 kDa dextran-Alexa488 and DAPI to A549 cells. The photomicrograph shows a 10× magnification.

In this example, the ability of the spraying method to address challenges in delivery of a broad range of molecule types and sizes were examined. Dextrans of increasing sizes, including 3 kDa, 40 kDa, 70 kDa, 500 kDa and 2,000 kDa were successfully delivered into A549 cells, as illustrated in FIG. 29. Other types of molecules with various dimensions such as linear siRNA molecules (approximately 15 kDa) and large antibody molecules (150 kDa) were also delivered, as illustrated in FIG. 30. Moreover, different types of molecules were delivered in a wide variety of combinations. For example, DAPI, phallotoxin and MitoTracker Red were successfully co-delivered into A549 cells, as was the combination of 10-kDa dextran-Alexa488 and DAPI, as illustrated in FIG. 31.

Figure 33:
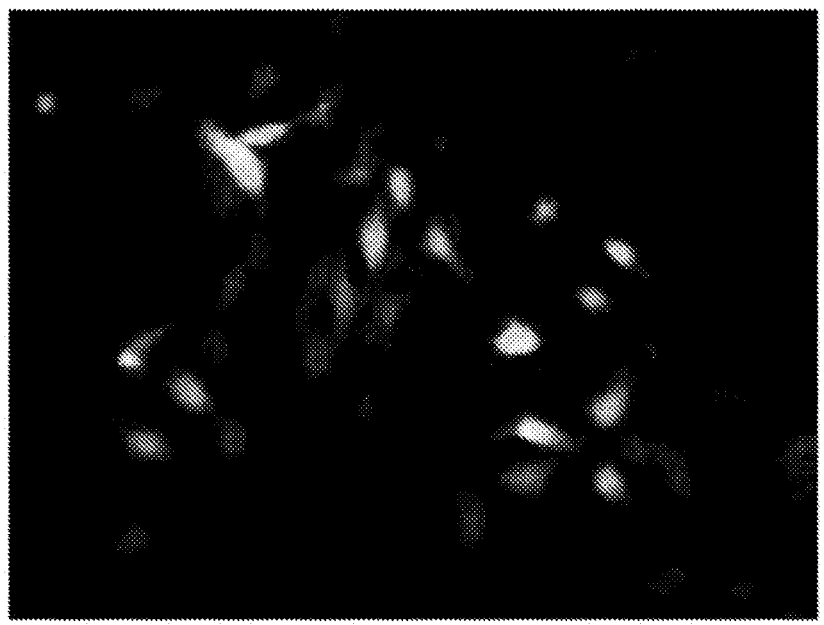
FIG. 33 is a photomicrograph illustrating the effect of delivery of GFP mRNA that was sprayfected into A549 cells. GFP protein expression was observed by fluorescence microscopy. The photomicrograph shows a 10× magnification.
Figure 34:
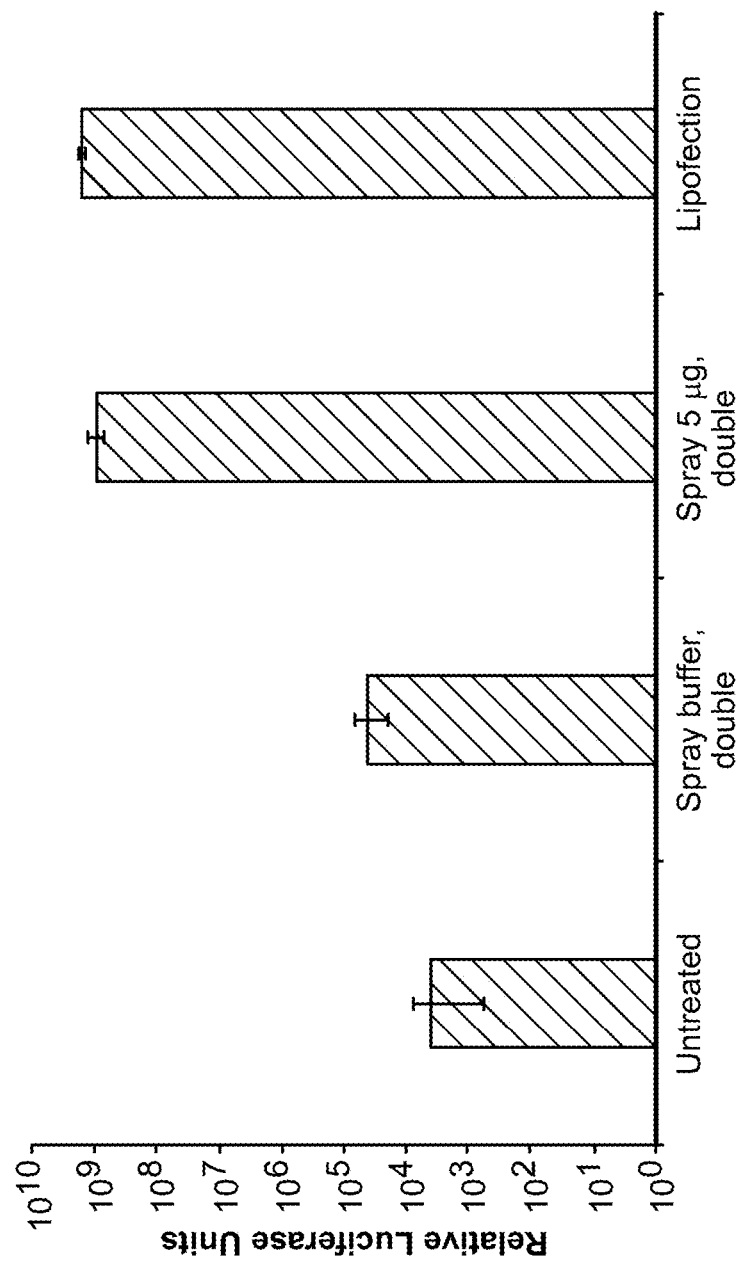
FIG. 34 is a bar graph showing the quantification (by luminometry) of the expression of luciferase when luciferase mRNA was delivered into A549 cells using exemplary methods of the current subject matter.
Figure 35:
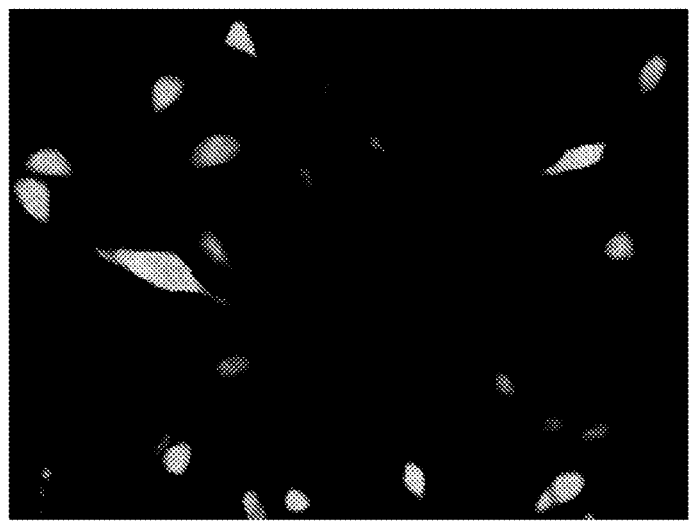
FIG. 35 is a photomicrograph illustrating the effect of delivery of delivery of pGFP plasmid DNA that was sprayfected into A549 cells. The expression of GFP protein was observed by fluorescence microcopy. The photomicrograph shows a 10× magnification.
Figure 36:
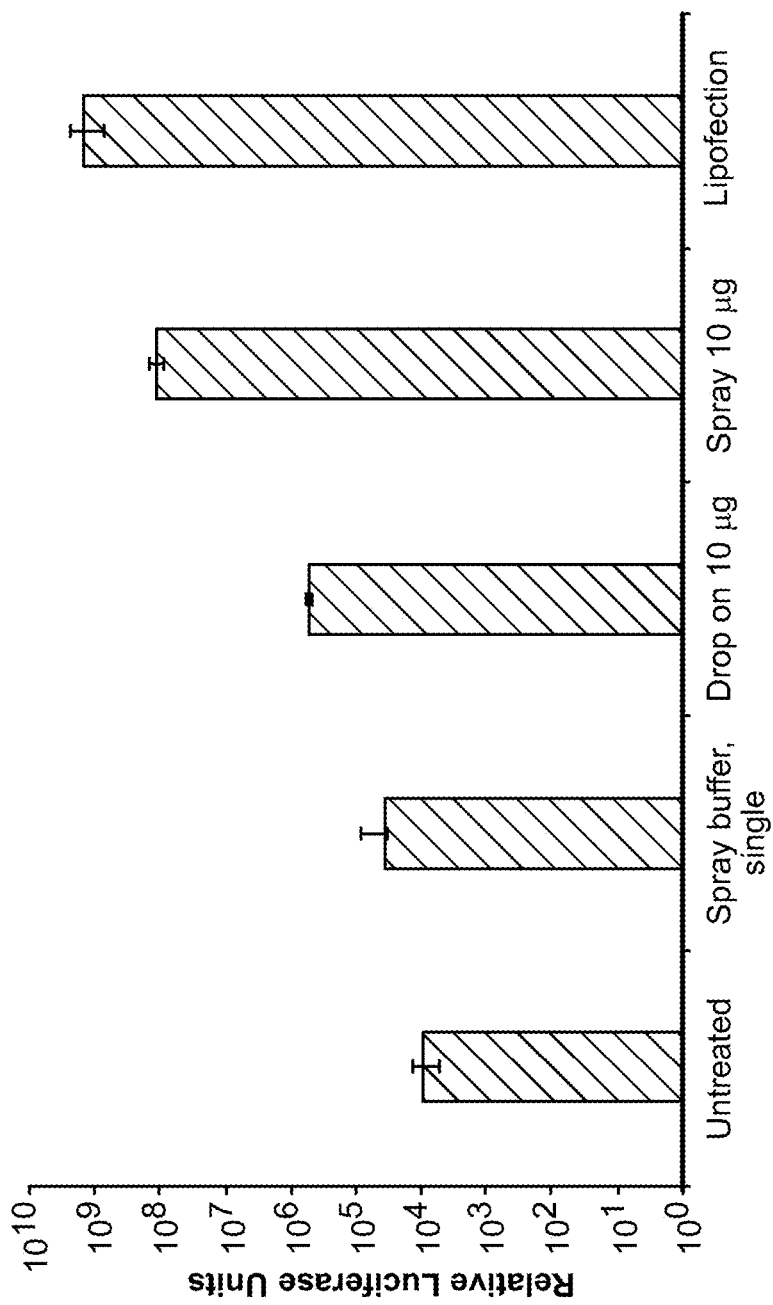
FIG. 36 is a bar graph showing the quantification (by luminometry) of the expression of luciferase when pGluc plasmid DNA was delivered into A549 cells using exemplary methods of the current subject matter.

Because spraying is a vectorless delivery method, of particular note is the ability to deliver mRNA and plasmid DNA with this approach. Reporter mRNAs encoding green fluorescent protein (GFP) and luciferase were sprayfected into CHO cells. GFP expression was observed by fluorescence microscopy and luciferase expression was detected by luminometry was comparable with Lipofectamine 2000 controls (FIG. 33 and FIG. 34). Similarly, DNA plasmids encoding GFP and luciferase were expressed when sprayfected into CHO cells (FIG. 35 and FIG. 36). These data demonstrate the functionality of nucleic acid payloads following delivery into cells. Furthermore, the ability to address adherent cells, and with very low toxicity, is important for primary and stem cell populations where large numbers of cells may not be available and minimal manipulation and passaging steps are desirable.

Example 14

Effect of Delivery Across Cell Types, Including Adherent Cell Lines, Primary Fibroblasts, Primary Stem Cells and Suspension Cells.

Figure 37:
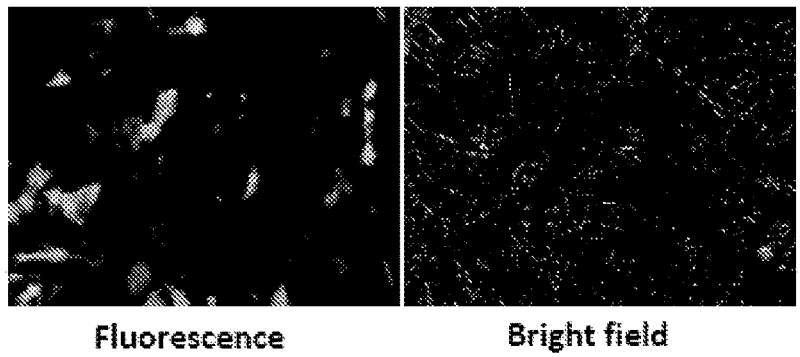
FIG. 37 is a photomicrograph illustrating the effect when 10 kDa dextran-Alexa488 was delivered into primary fibroblasts. Dextran was visible in fibroblasts by fluorescence microscopy. A 10× magnification is shown.
Figure 38:
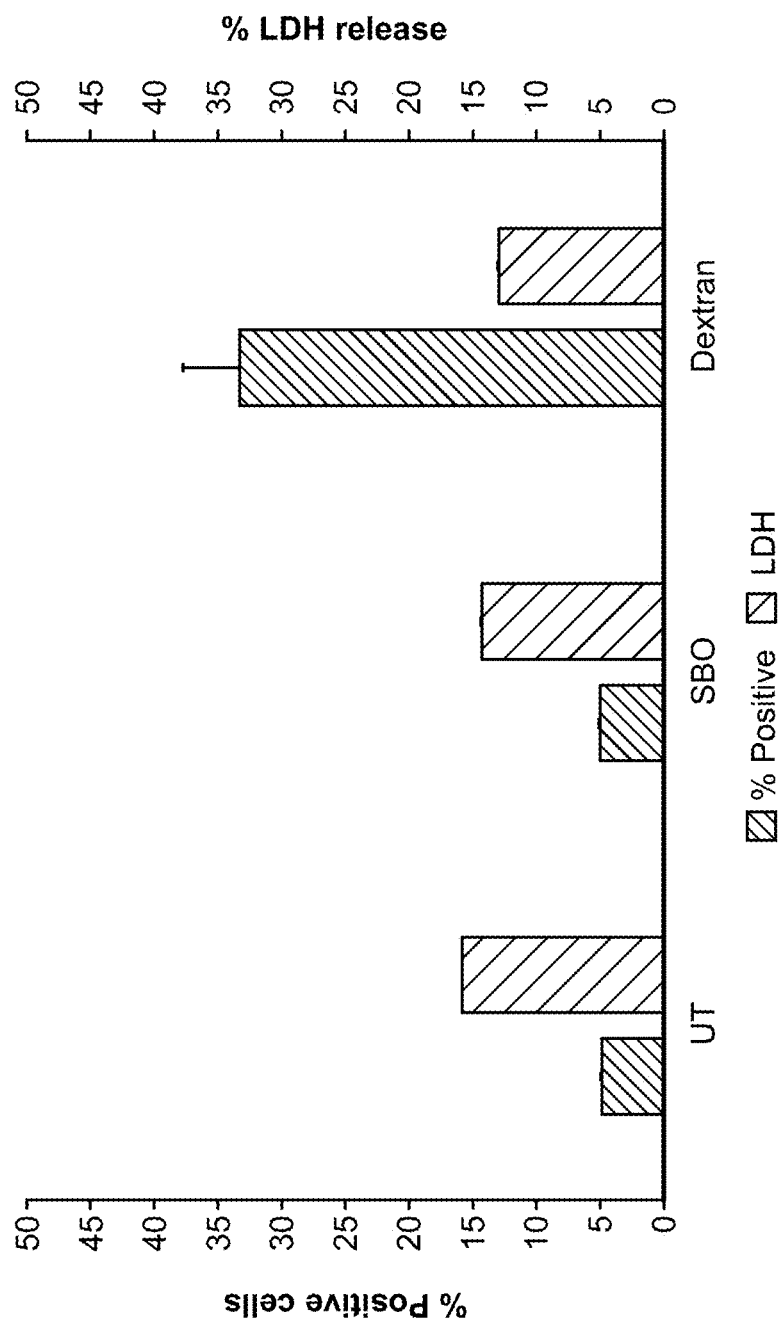
FIG. 38 is a bar graph showing the effect of efficiency and toxicity of delivery of 10 kDa dextran Alexa488 delivered into primary fibroblasts, as quantified by flow cytometry and an LDH assay, respectively.
Figure 39:
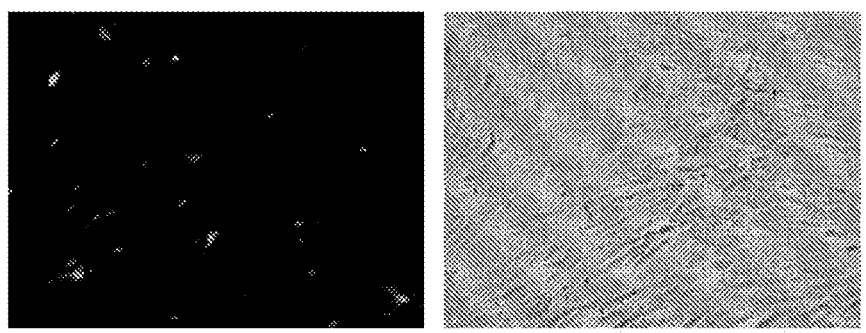
FIG. 39 is a photomicrograph illustrating the effect when 10 kDa dextran-Alexa488 was delivered into mesenchymal stem cells (MSC). Dextran was visible in MSCs by fluorescence microscopy, at 10× magnification.
Figure 40:
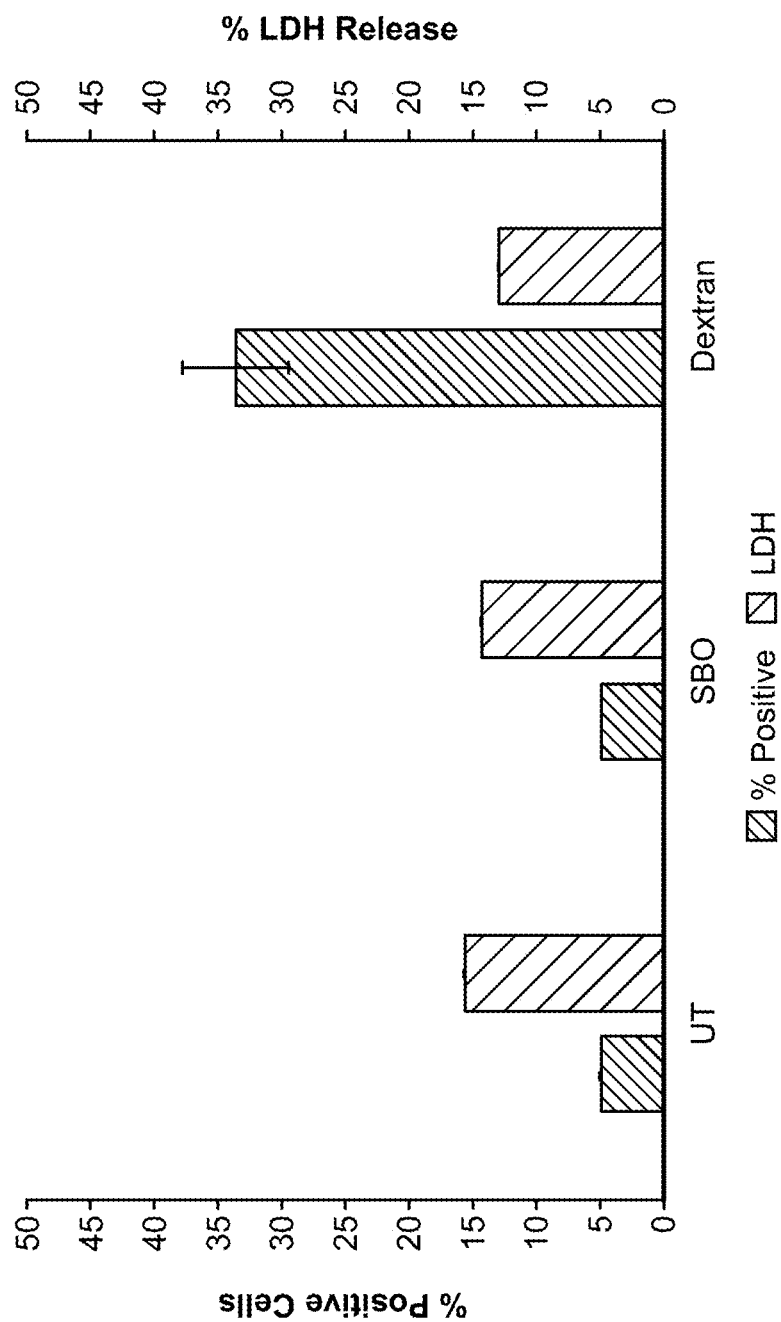
FIG. 40 is a bar graph showing the effect of efficiency and toxicity of delivery of 10 kDa dextran Alexa488 delivered into MSCs, as quantified by flow cytometry and an LDH assay, respectively.
Figure 41A:
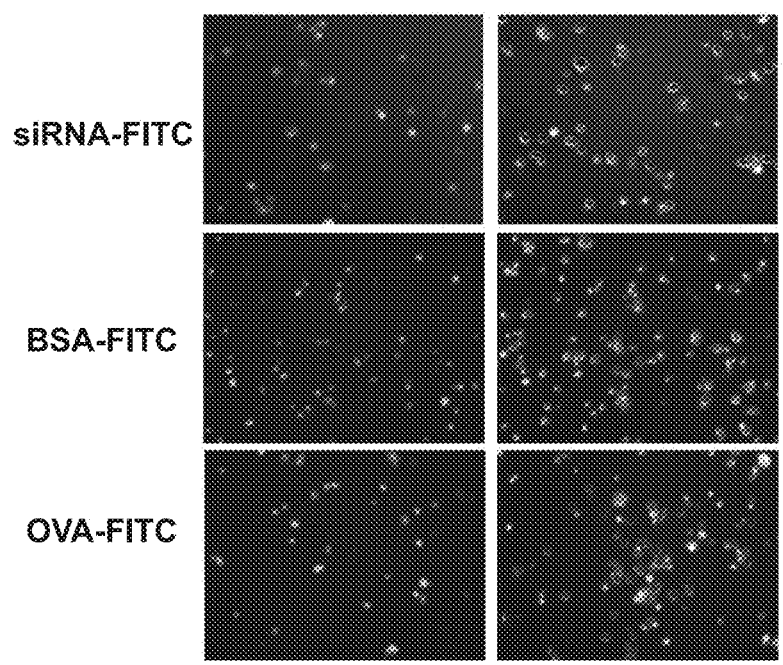
FIG. 41A is a photomicrograph illustrating the effect of delivery of siRNA (top panel), BSA (middle panel), and OVA (bottom panel) into U226 human multiple myeloma cells.
Figure 42:
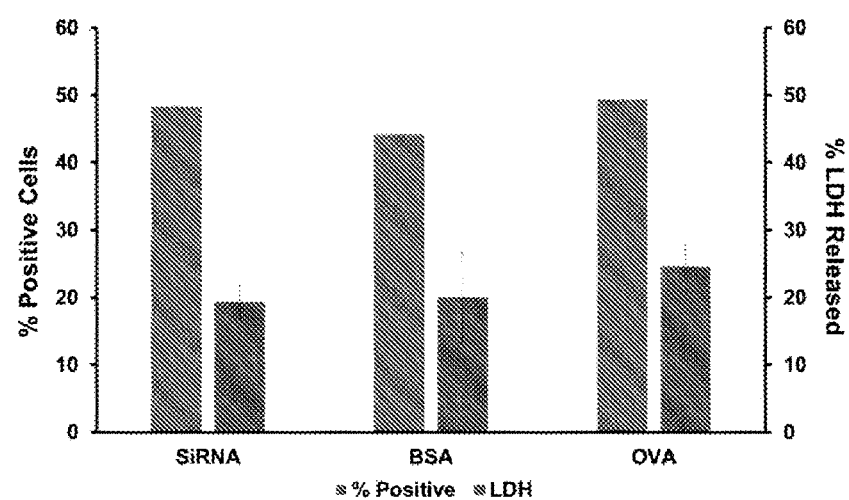
FIG. 42 is a bar graph illustrating the effect of delivery efficiency and cell toxicity of siRNA (top panel), BSA (middle panel), and OVA (bottom panel) into U226 human multiple myeloma cells, as quantified by flow cytometry and an LDH assay, respectively.

In this example, the delivery method across cell types was evaluated. The delivery technique was successfully deployed across a wide range of adherent cell types including A549 and CHO cell lines as well as primary fibroblasts, as shown in FIG. 37 and primary MSC, shown in FIG. 39. Furthermore, the protocol was successfully adapted to address suspension cells such as U226 human multiple myeloma cells, shown in FIG. 41A. The cell suspension was placed into a porous cell culture plate insert and a brief gentle vacuum of approximately −0.5 to −0.68 bar was applied for 20-45 sec to remove supernatant before the cells were sprayed (FIG. 41A and FIG. 42).

Figure 41B:
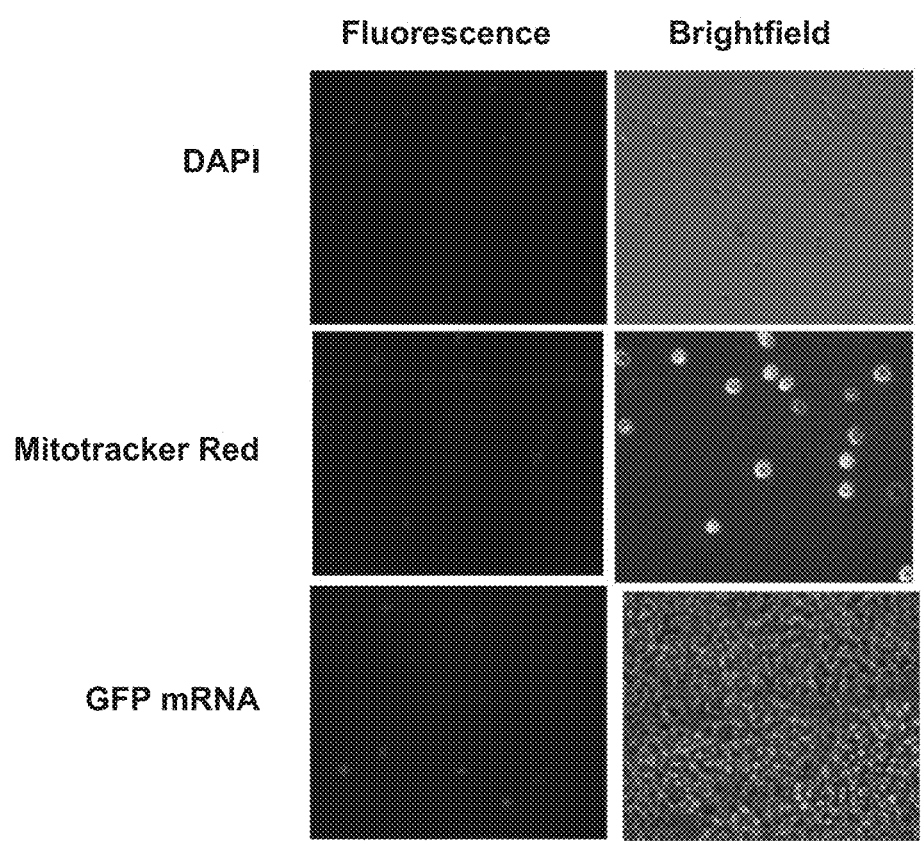
FIG. 41B is a photomicrograph illustrating the effect of delivery of DAPI (top panel) and MItotracker Red (middle panel) to Jurkat cells. Additionally, mRNA for green fluorescent protein (GFP) was delivered to Jurkat cells, and GFP expression was observed at 24 hours post-delivery.

Additionally, the protocol was successfully adapted to address suspension cells such as Jurkat cells, T-lymphocyte cells, shown in FIG. 41B. DAPI and Mitotracker Red were successfully delivered to the Jurkat cells (FIG. 41B top and middle panel, respectively). Furthermore, mRNA encoding for GFP was delivered to Jurkat cells, and GFP expression was observed at 24 hours post-delivery.

Example 15

Evaluation of the Delivery Technology on the Intracellular Delivery of Proteins.

Figure 44:
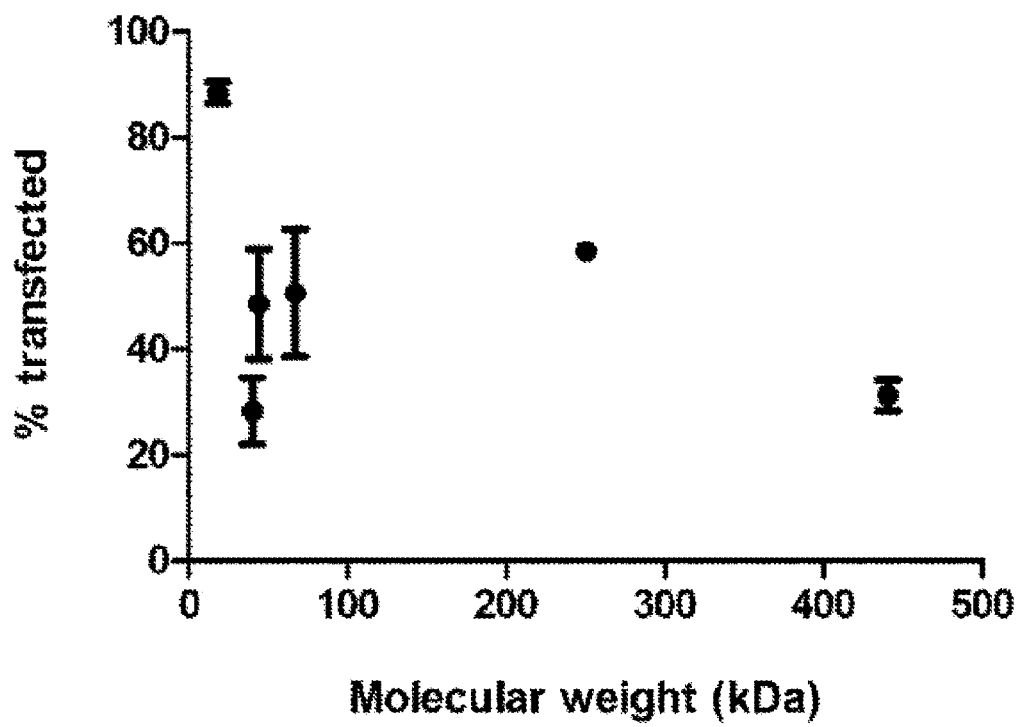
FIG. 44 is a graph showing the efficiencies of delivery of a wide range of proteins into CHO cells by the exemplary methods of the current subject matter. The Efficiencies were quantified by flow cytometry.
Figure 45:
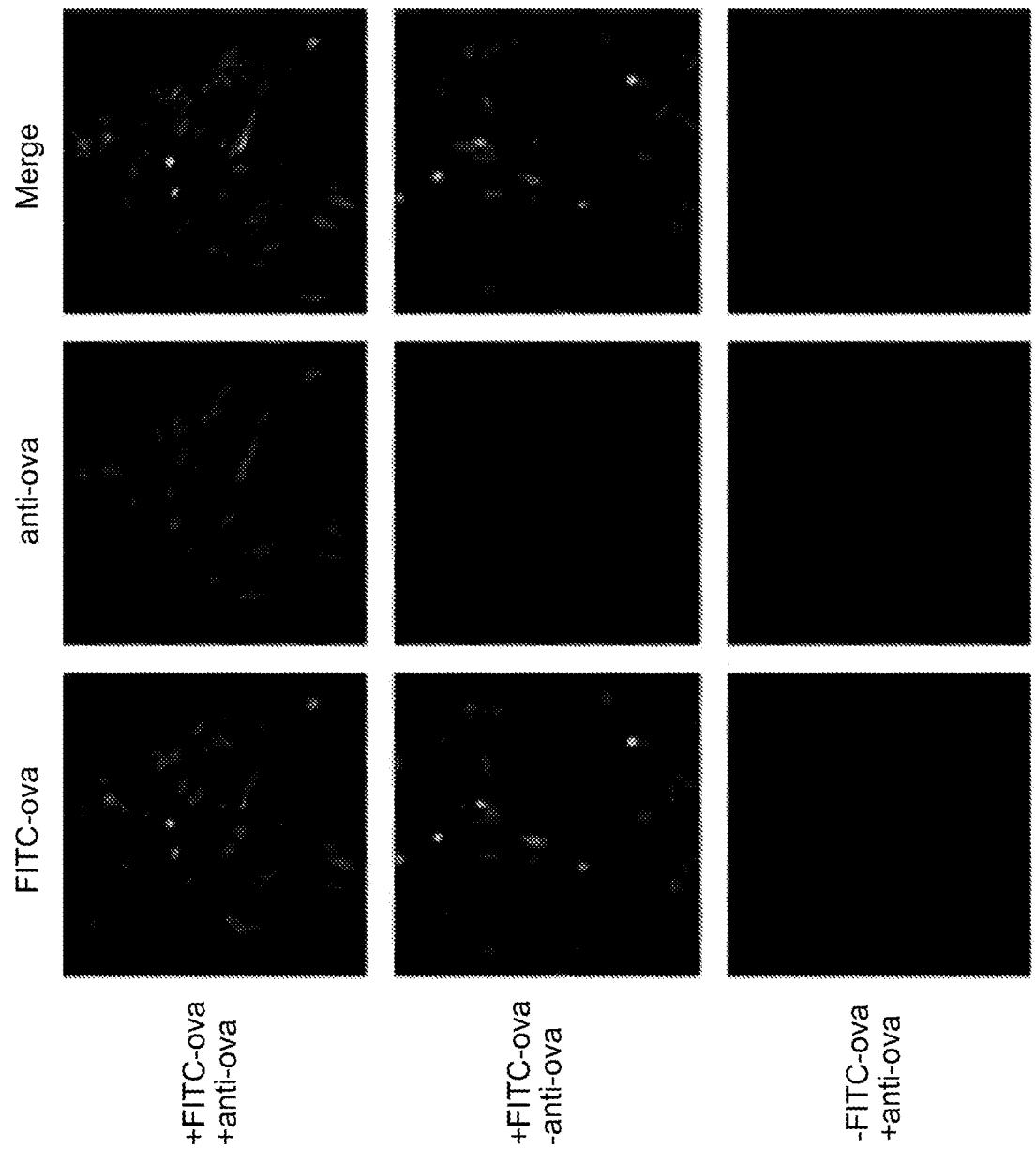
FIG. 45 is a photomicrograph showing the immunofluorescence detection of ovalbumin-FITC delivered into CHO cells. Delivery of ovalbumin-FITC into CHO cells was validated by immunofluorescence using an anti-ovalbumin antibody.
Figure 46:
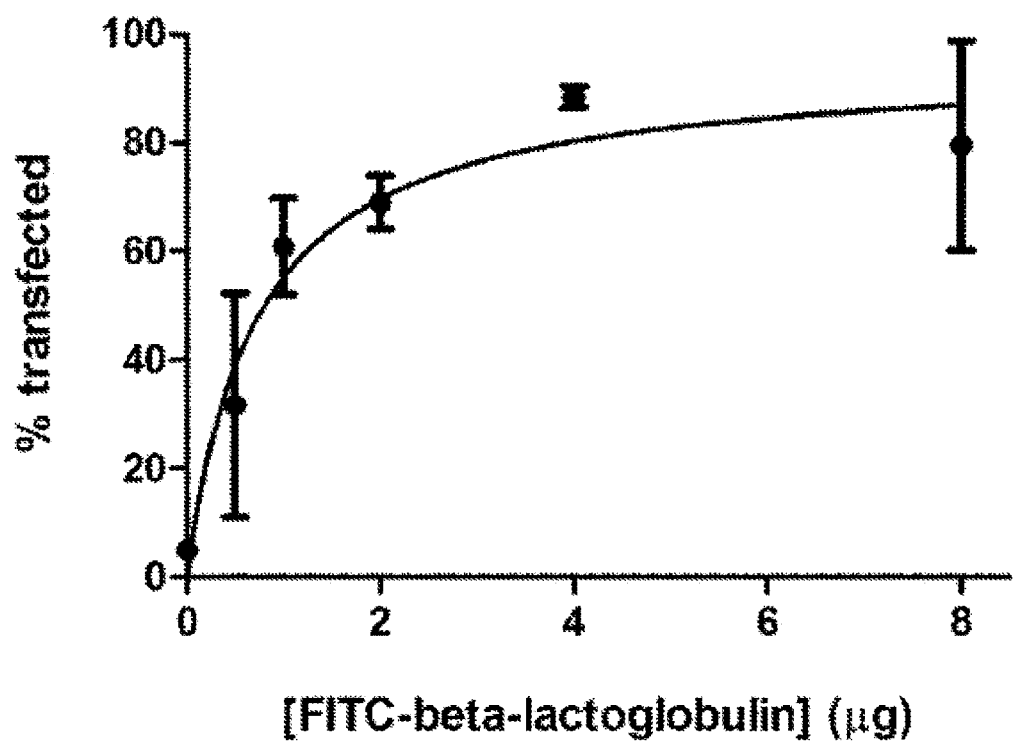
FIG. 46 is a graph showing the dose response for delivery of beta-lactoglobulin into CHO cells. Increasing efficiency of delivery was seen with increasing concentrations of beta-lactoglobulin-FITC delivered to CHO cells by methods of the current subject matter (n=3).

A notable application of delivery technology is the intracellular delivery of proteins. Proteins are a very diverse group in terms of their size, shape and chemistry and few methods are currently available for efficient delivery of these molecules. A broad range of proteins of increasing sizes from 18.3 kDa to 443 kDa were labeled with either FITC or Alexa-488 and their delivery by spraying was examined. All proteins were successfully delivered (FIG. 43 and FIG. 44) into CHO cells. A general trend towards declining delivery efficiencies with increasing size of protein (FIG. 44) was observed. To further confirm that proteins were delivered into cells, ovalbumin-FITC was delivered and subsequently detected by immunofluorescence using an anti-ovalbumin antibody (FIG. 45). For a given protein, in this case beta-lactoglobulin, a dose response was evident with increasing efficiency of delivery evident with increasing concentration of protein sprayed (FIG. 46).

Example 16

Evaluation of the Functionality of Proteins Post-Delivery into Cells.

Figure 47:
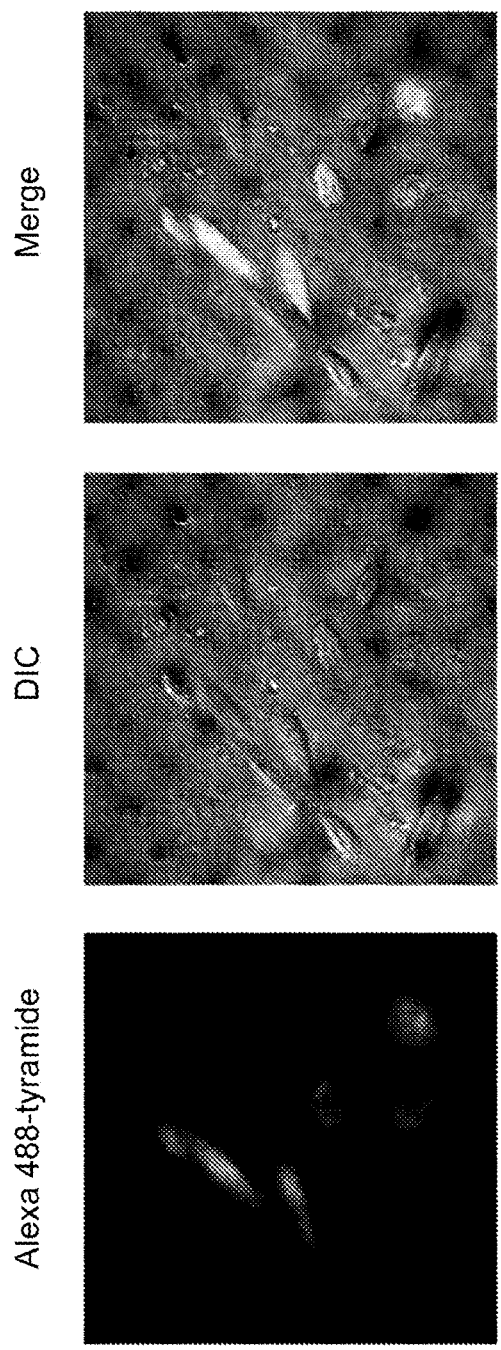
FIG. 47 is a photomicrograph illustrating the activity and localization of HRP delivered to cells. Alexa488-labeled tyramide substrate was used to demonstrate activity and localization of HRP in CHO cells following delivery of HRP by methods of the current subject matter.
Figure 48:
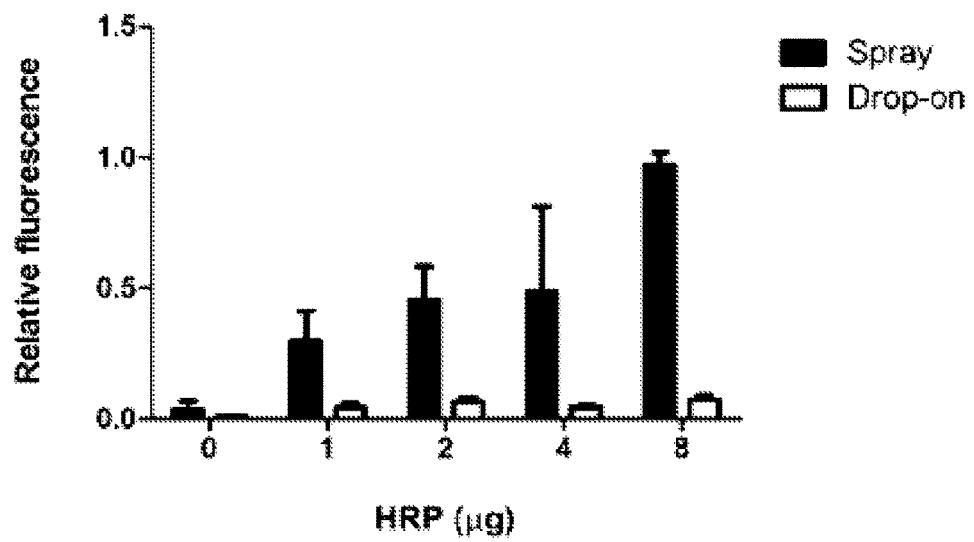
FIG. 48 is a bar graph illustrating the increased production of fluorescent DCF product detected with increased dose of HRP delivered into CHO cells.
Figure 49:
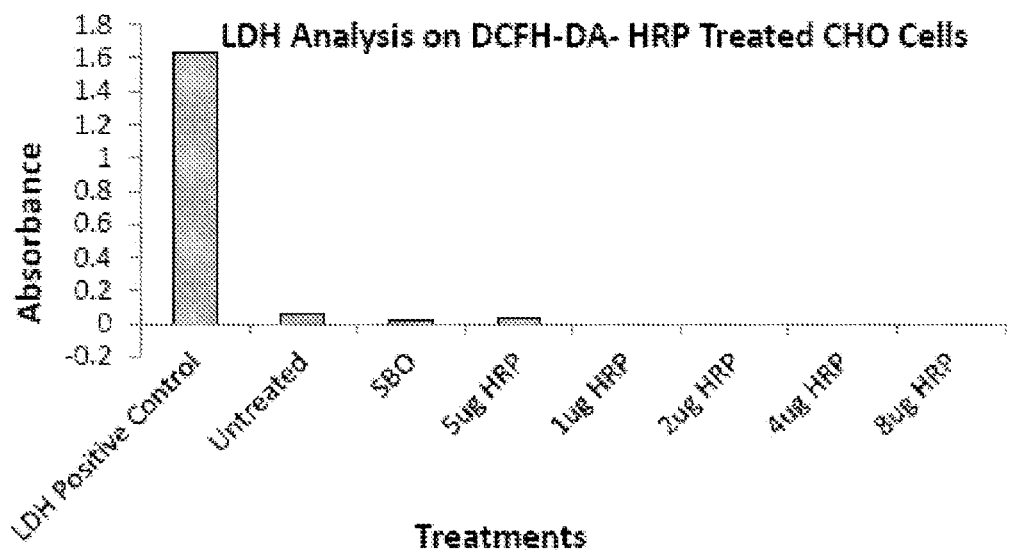
FIG. 49 is a bar graph indicating that the LDH analysis demonstrated that the assay was not toxic to cells.

The functionality of proteins post-delivery into cells was examined. Various assays are available for the detection of horse radish peroxidase (HRP) activity and two assays were used to detect HRP activity following spraying into CHO cells. Firstly, the Tyramide Signal Amplification (TSA™) assay was adapted, which normally uses the catalytic activity of HRP to generate high density labelling of a target protein or nucleic acid sequence in situ. The Alexa Fluor® 488-labelled tyramide substrate was used to demonstrate activity and localization of HRP in CHO cells following delivery by spraying (FIG. 47). Secondly, a DCFH-DA assay was used to quantify HRP activity. 2',7' dichlorofluorescin diacetate (DCFH-DA) is a hydrophobic non-fluorescent molecule that penetrates rapidly into cells and is hydrolyzed by intracellular esterases to give the DCFH molecule which can be oxidized to its fluorescent product 2',7'dichlorofluorescein (DCF) which can be measured. HRP was sprayfected into CHO cells and the cells were incubated with DCFH-DA. Increasing production of DCF was observed with increasing dose of HRP delivered (FIG. 48). No toxicity was observed with this assay (FIG. 49).

Example 17

Labeling Primary MSC by Spraying for Tracking to Target Organs was Evaluated.

Several cell types, including MSC, are used for in vivo cell therapy applications. However, success with many of these strategies has been hampered by lack of understanding about cell trafficking in the body. The efficiency of trafficking to target organs versus sequestration in non-target organs is difficult to investigate and delivery of labeled cells in animal studies is often used to understand these processes. Efficient and rapid labeling of cells is not currently achievable. Standard fluorescent labels such as FITC and other fluorophores are usually not bright enough to be detected in situ in tissues and animals. Brighter labels such as quantum-dots (Q-dots) have been more recently developed but these require extended periods of incubation with cells, usually overnight, in order to achieve satisfactory levels of labelling. The method of the current subject matter is a rapid delivery method whereby payloads are delivered within minutes to target cells. The ability of the method to deliver Q-dots to primary MSC was examined, and whether these could be detected in situ following ex vivo injection in mouse spleens.

Figure 50:
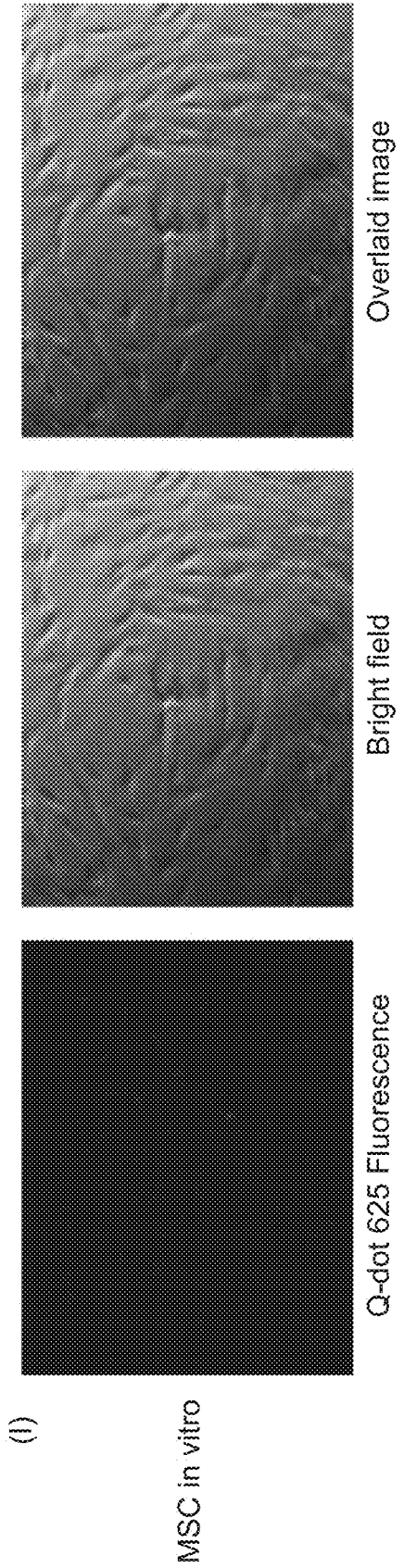
FIG. 50 is a photomicrograph illustrating the labeling of MSC with Q-dots for tracking studies. Primary MSCs were delivered with Q-dot 625 in vitro.
Figure 51:
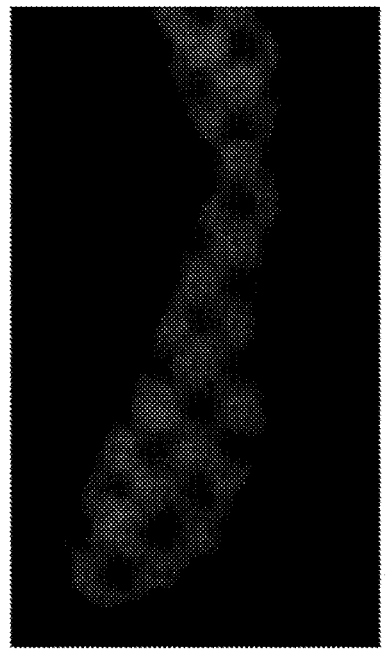
FIG. 51 is a photomicrograph illustrating the labeling of MSC with Q-dots for tracking studies. MSCs were injected into mouse spleens ex vivo. Q-dot fluorescence was analyzed using the Cryovis instrument.
Figure 51:
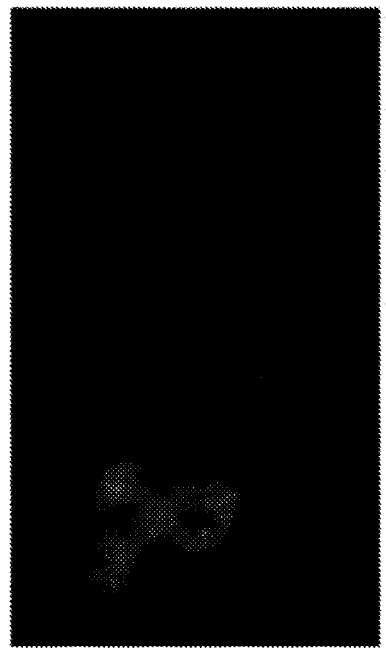

Q-dots were sprayfected into cultured primary mouse MSC, as illustrated in FIG. 50. Spleens were dissected from mice and $2\times10^5$ sprayfected MSC in 100 µl culture medium were injected into the spleens. Fluorescence in the spleens was examined by 3-dimensional cryoimaging using the Cryovis instrument. Q-dots were detected in the spleens as shown in FIG. 51.

Example 18

Experimentally Measured Volume Delivered Per Cell in A549 Cells, CHO Cells, and MSCs.

The areas of three different cell lines (A549, CHO, and MCSs) were experimentally calculated and measured (FIG. 55). The average area for each of the cell lines was measured to be 932 µm$^2$, 372 µm$^2$, and 2054 µm$^2$ for A549, CHO, and MCSs, respectively. Thus, the calculated number of cells per well (based on the size of a 48-well cell culture plate), was calculated to be 102,500, 255,000, and 46200 for A549, CHO, and MCSs, respectively. Upon delivery of 10 µL, approximately $9.8\times10^{-5}$ µL per cell were delivered to A549 cells, $3.9\times10^{-5}$ µL per cell were delivered to CHO cells, and $2.2\times10^{-4}$ µL per cell were delivered to MSCs. The experimentally measured volume delivered per cell of these three examples fall within the range of the theoretical calculations (e.g., $6.0\times10^{-7}$ microliter per cell and $7.4\times10^{-4}$ microliter per cell) utilizing cell diameter estimations from the ATCC, Celeromics Technologies, and other cell culture references known by one skilled in the art.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method for delivering a payload across a plasma membrane of a cell, comprising:
   providing a population of cells; and
   contacting the population of cells with a volume of aqueous solution, whereby the payload is subsequently delivered across the plasma membrane of the cell, the aqueous solution including the payload and an alcohol at a concentration greater than 2 percent (v/v); wherein the population of cells is in contact with the aqueous solution for 2 seconds to 2 minutes prior to adding a second volume of buffer or culture medium to submerse or suspend the population of cells,
   wherein the population of cells comprises non-adherent cells, and the non-adherent cells include at least one of primary or immortalized hematopoietic stem cell (HSC), T cells, natural killer (NK) cells, cytokine-induced killer (CIK) cells, human cord blood CD34+ cells, B cells, or induced pluripotent stem cells;
   wherein contacting the population of cells with the volume of aqueous solution is performed by gas propelling the aqueous solution to form a spray.

2. The method of claim 1, wherein the volume of aqueous solution including the payload is between $6.0\times10^{-7}$ microliter per cell and $7.4\times10^{-4}$ microliter per cell.

3. The method of claim 1, further comprising creating a cell occupied area by at least removing media from the population of cells such that the non-adherent cells rest on the cell occupied area, wherein a total volume of aqueous solution is delivered to the cell-occupied area, wherein (a) the total volume of aqueous solution is 20 µl and the cell-occupied area is about 1.9 cm², wherein about is within 10 percent; or (b) the total volume of aqueous solution is 10 µl and the cell-occupied area is about 0.95 cm², wherein about is within 10 percent.

4. The method of claim 1, wherein said aqueous solution comprises an ethanol concentration of 5 to 30% (v/v).

5. The method of claim 1, wherein said aqueous solution comprises one or more of 75 to 98% $H_2O$, 2 to 45% ethanol, 6 to 91 mM sucrose, 2 to 35 mM potassium chloride, 2 to 35 mM ammonium acetate, and 1 to 14 mM (4-(2-hydroxyethyl)-1-piperazineethanesulfonic acid) (HEPES).

6. The method of claim 1, wherein the payload comprises a small chemical molecule, a peptide or protein, or a nucleic acid.

7. The method of claim 6, wherein
   (a) the small chemical molecule comprises a molecular mass of less than 1,000 Da;
   (b) wherein the small chemical molecule comprises MitoTracker® Red CMXRos, propidium iodide, methotrexate, or DAPI (4',6-diamidino-2-phenylindole);
   (c) the peptide comprises ecallantide, liraglutide, or icatibant;
   (d) the nucleic acid comprises a small-interfering RNA (siRNA), and wherein the siRNA molecule comprises a molecular mass of about 15,000 Da;
   (e) the protein comprises a molecular mass about 1,000-150,000 Da;
   (f) the protein comprises an antibody, or fragment thereof, and wherein the antibody or fragment thereof comprises an anti-actin antibody, an anti-GAPDH antibody, an anti-Src antibody, an anti-Myc ab, and an anti-Raf antibody; or
   (g) the nucleic acid molecule comprises greater than 5,000,000 Da.

8. The method of claim 1, wherein the payload comprises a therapeutic agent, a diagnostic agent, a fluorescent molecule, or a detectable nanoparticle.

9. The method of claim 8, wherein (a) the therapeutic agent includes at least one of cisplatin, aspirin, a statin, and fluoxetine; (b) the diagnostic agent includes at least one of methylene blue, patent blue V, and indocyanine green; or (c) the nanoparticle comprises a quantum dot.

10. The method of claim 1, further comprising creating a cell occupied area by at least removing media from the population of cells such that the non-adherent cells rest on the cell occupied area, wherein the population of cells at rest on the cell occupied area is substantially confluent, wherein substantially is greater than 75 percent confluent.

11. The method of claim 1, further comprising creating a cell occupied area by at least removing media from the population of cells such that the non-adherent cells rest on the cell occupied area, wherein the population of cells at rest on the cell occupied area form a monolayer of cells.

12. The method of claim 1, wherein the population of cells comprises macrophages.

13. The method of claim 1, wherein the population of cells comprises mesenchymal stem cells.

14. The method of claim 1, wherein the payload comprises nucleic acid.

15. The method of claim 1, wherein the payload comprises mRNA.

16. The method of claim 1, wherein the aqueous solution includes the alcohol at a concentration greater than 5 percent (v/v).

17. The method of claim 1, wherein said aqueous solution comprises an ethanol at a concentration of 2 to 30% (v/v).

18. The method of claim 1, wherein the volume of aqueous solution is delivered to the population of cells in the form of the spray.

19. The method of claim 18, wherein the spray comprises a colloidal suspension comprising a diameter of 1 nm to 100 µm.

20. The method of claim 1, wherein the buffer or culture medium comprises a second aqueous solution.

21. The method of claim 20, wherein the second aqueous solution comprises saline.

22. The method of claim 21, wherein the saline comprises phosphate buffered saline (PBS).

23. A method for delivering a payload across a plasma membrane of a cell, comprising:
   providing a population of cells; and
   contacting the population of cells with a volume of aqueous solution, whereby the payload is subsequently delivered across the plasma membrane of the cell, the aqueous solution including the payload and an alcohol at a concentration greater than 2 percent (v/v), wherein the population of cells is in contact with the aqueous solution for 2 seconds to 2 minutes prior to adding a second volume of buffer or culture medium to submerse or suspend the population of cells, wherein the population of cells comprises adherent cells, and the adherent cells include at least one of primary or immortalized mesenchymal stem cells, lung cells, neuronal cells, fibroblasts, human umbilical vein (HUVEC) cells, and human embryonic kidney (HEK) cells, wherein contacting the population of cells with the volume of aqueous solution is performed by gas propelling the aqueous solution to form a spray.

24. The method of claim 23, wherein said aqueous solution comprises an ethanol concentration of 5 to 30% (v/v).

25. A method for delivering a payload across a plasma membrane of a cell, comprising:

providing a population of cells; and contacting the population of cells with a volume of aqueous solution, whereby the payload is subsequently delivered across the plasma membrane of the cell, the aqueous solution including the payload and an alcohol at a concentration greater than 2 percent (v/v), wherein the population of cells is in contact with the aqueous solution for 2 seconds to 2 minutes prior to adding a second volume of buffer or culture medium to submerse or suspend the population of cells, wherein contacting the population of cells with the volume of aqueous solution is performed by gas propelling the aqueous solution to form a spray, and wherein the buffer or culture medium comprises a second aqueous solution.

26. The method of claim 25, wherein the population of cells comprises adherent cells, and the adherent cells include at least one of primary or immortalized mesenchymal stem cells, lung cells, neuronal cells, fibroblasts, human umbilical vein (HUVEC) cells, or human embryonic kidney (HEK) cells.

27. The method of claim 25, wherein the population of cells comprises non-adherent cells, and the non-adherent cells include at least one of primary or immortalized hematopoietic stem cell (HSC), T cells, natural killer (NK) cells, cytokine-induced killer (CIK) cells, human cord blood CD34+ cells, or B cells.

28. The method of claim 25, wherein said aqueous solution comprises an ethanol concentration of 5 to 30% (v/v).

* * * * *